US008642073B2

(12) United States Patent
Mannino et al.

(10) Patent No.: US 8,642,073 B2
(45) Date of Patent: Feb. 4, 2014

(54) ENCOCHLEATION METHODS, COCHLEATES AND METHODS OF USE

(75) Inventors: Raphael J. Mannino, Annandale, NJ (US); Susan Gould-Fogerite, Annandale, NJ (US); Sara L. Krause-Elsmore, Kearny, NJ (US); David Delmarre, Jersey City, NJ (US); Ruying Lu, New Providence, NJ (US)

(73) Assignees: BioDelivery Sciences International, Inc., Raleigh, NC (US); University of Medicine and Dentistry of New Jersey, Somerset, NJ (US)

(*) Notice: Subject to any disclaimer, the term of this patent is extended or adjusted under 35 U.S.C. 154(b) by 1697 days.

(21) Appl. No.: 11/653,434

(22) Filed: Jan. 11, 2007

(65) Prior Publication Data

US 2007/0237814 A1 Oct. 11, 2007

Related U.S. Application Data

(63) Continuation of application No. 10/822,230, filed on Apr. 9, 2004, now abandoned.

(60) Provisional application No. 60/461,483, filed on Apr. 9, 2003, provisional application No. 60/463,076, filed on Apr. 15, 2003, provisional application No. 60/502,557, filed on Sep. 11, 2003, provisional application No. 60/537,252, filed on Jan. 15, 2004, provisional application No. 60/499,247, filed on Aug. 28, 2003, provisional application No. 60/532,755, filed on Dec. 24, 2003, provisional application No. 60/556,192, filed on Mar. 24, 2004.

(51) Int. Cl.
*A61K 9/127* (2006.01)

(52) U.S. Cl.
USPC ........................................................ 424/450

(58) Field of Classification Search
None
See application file for complete search history.

(56) References Cited

U.S. PATENT DOCUMENTS

| 4,078,052 A | 3/1978 | Papahadjopoulos |
| 4,698,327 A | 10/1987 | Nagarajan et al. |
| 4,725,442 A | 2/1988 | Haynes |
| 4,871,488 A | 10/1989 | Mannino et al. |
| 4,874,795 A | 10/1989 | Yesair |
| 4,906,476 A | 3/1990 | Radhakrishnan |
| 4,990,291 A | 2/1991 | Schoen et al. |
| 5,026,557 A | 6/1991 | Estis et al. |
| 5,100,591 A | 3/1992 | Leclef et al. |
| 5,269,979 A | 12/1993 | Fountain |
| 5,409,698 A | 4/1995 | Anderson et al. |
| 5,484,589 A | 1/1996 | Saiganik |
| 5,571,517 A | 11/1996 | Yesair |
| 5,580,859 A | 12/1996 | Feigner et al. |
| 5,589,466 A | 12/1996 | Feigner et al. |
| 5,643,574 A | 7/1997 | Gould-Fogerite et al. |
| 5,834,015 A | 11/1998 | Oleske et al. |
| 5,840,707 A | 11/1998 | Mannino et al. |
| 5,851,536 A | 12/1998 | Yager et al. |
| 5,994,318 A | 11/1999 | Gould-Fogerite et al. |
| 6,120,751 A * | 9/2000 | Unger .......................... 424/9.51 |
| 6,153,217 A | 11/2000 | Jin et al. |
| 6,340,591 B1 | 1/2002 | Margolis et al. |
| 6,403,056 B1 | 6/2002 | Unger |
| 6,406,713 B1 | 6/2002 | Janoff et al. |
| 6,447,800 B2 | 9/2002 | Hope |
| 6,592,894 B1 | 7/2003 | Zarif et al. |
| 6,808,720 B2 | 10/2004 | Unger |
| 2004/0092727 A1 | 5/2004 | Jin |

FOREIGN PATENT DOCUMENTS

| EP | 435 503 A1 | 7/1991 |
| EP | 667 353 A1 | 8/1995 |
| FR | 2 221 122 A | 10/1974 |
| WO | WO 96 25942 | 8/1996 |
| WO | WO 97 30725 | 8/1997 |
| WO | WO 00 42989 | 7/2000 |
| WO | WO 01 52817 | 7/2001 |
| WO | WO 2004 012709 | 2/2004 |

OTHER PUBLICATIONS

Anderson, et al. Formulation and evaluation of a folic acid receptor-targeted oral vancomycin liposomal dosage form. *Pharm Res* 18(3): 316-22, 2001.
Arndt, et al. Liposomal bleomycin: increased therapeutic activity and decreased pulmonary toxicity in mice. *Drug Deliv* 8(1): 1-7, 2001.
Asai, "Formation of the dispersed particles composed of retinol and phosphatidylserine," *Int J Pharm*, 253: 89-95, 2003.
Aviles, et al. Pegylated liposomal doxorubicin in combination chemotherapy in the treatment of previously untreated aggressive diffuse large-B-cell lymphoma. *Med Oncol* 19(1): 55-58, 2002.
Booser, et al. Anthracycline antibiotics in cancer therapy. Focus on drug resistance. *Drugs*, 47(2):223-58, 1994.
Couvreur, et al. Nano- and microparticles for the delivery of polypeptides and proteins. *Adv. Drug Delivery Rev*, 10: 141-162, 1993.
Creuzenet, et al. Interaction of alpha s2- and beta-casein signal peptides with DMPC and DMPG liposomes. *Peptides*, 18(4): 463-472, 1997.
Deres, et al. In vivo priming of virus-specific cytotoxic T lymphocytes with synthetic lipopeptide vaccine. *Nature*. 342(6249):561-4, 1989.

(Continued)

*Primary Examiner* — Brian Gulledge
*Assistant Examiner* — Snigdha Maewall
(74) *Attorney, Agent, or Firm* — McCarter & English, LLP; Danielle L. Herritt; Wei Song

(57) ABSTRACT

Disclosed are novel methods for making cochleates and cochleate compositions that include introducing a cargo moiety to a liposome in the presence of a solvent. Also disclosed are cochleates and cochleate compositions that include an aggregation inhibitor, and optionally, a cargo moiety. Additionally, anhydrous cochleates that include a protonized cargo moiety, a divalent metal cation and a negatively charge lipid are disclosed. Methods of using the cochleate compositions of the invention, including methods of administration, are also disclosed.

17 Claims, 61 Drawing Sheets

(56) References Cited

OTHER PUBLICATIONS

Finberg, et al. The induction of virus-specific cytotoxic T lymphocytes with solubilized viral and membrane proteins. *J Exp Med.* 148(6):1620-7, 1978.
Gemmell, et al. Comparative effects of drugs on four paw oedema models in the rat. *Agents Actions.* 9(1): 107-116, 1979.
Goodman-Snitkoff, et al. The glycoprotein isolated from vesicular stomatitis virus is mitogenic for mouse B lymphocytes. *J Exp Med* 153: 1489-1502, 1981.
Goodman-Snitkoff, et al. Defining minimal requirements for antibody production to peptide antigens. *Vaccine.* 8(3):257-62, 1990.
Goodman-Snitkoff, et al. Role of intrastructural/intermolecular help in immunization with peptide-phospholipid complexes. *J Immunol.* 147(2):410-5, 1991.
Gould-Fogerite, et al. Chimerasome-mediated gene transfer in vitro and in vivo. *Gene.* 84(2):429-38, 1989.
Gould-Fogerite, et al., Rotary dialysis: its application to the preparation of large liposomes and large proteoliposomes (protein-lipid vesicles) with high encapsulation efficiency and efficient reconstitution of membrane proteins. *Anal Biochem.* 148(1):15-25, 1985.
Gould-Fogerite, et al. The reconstitution of biologically active glycoproteins into large liposomes: use as a delivery vehicle to animal cells. *Adv Memb Biochem Bioener.* 569-586, 1988.
Gould-Fogerite, et al. Liposome preparation and related techniques. *Liposome Technology,* $2^{nd}$ Edition. 1:67-80, 1993.
Gould-Fogerite, et al. Interaction of liposomes with the biological milieu. *Liposome Technology,* $2^{nd}$ Edition. 3:261-276, 1993.
Gould-Fogerite, et al. "Mucosal and systemic immunization using cochleate and liposome vaccines" *J. Liposome Res,* 6(2): 357-79, 1996.
Gould-Fogerite et al., "Targeting immune response induction with cochleate and liposome-based vaccines" *Adv Drug Delivery Rev,* 32(3), pp. 273-287, 1998.
Gould-Fogerite, et al. Cochleates for induction of mucosal and systemic immune responses. *Meth Molec Med* 42: 179-196, 1999.
Gould-Fogerite, et al., Cochleate Delivery Vehicles: Applications in Vaccine Delivery. *J Liposome Res,* 10(4): 339-358, 2000.
Hale, et al. Elicitation of anti-Sendai virus cytotoxic T lymphocytes by viral and H-2 antigens incorporated into the same lipid bilayer by membrane fusion and by reconstitution into liposomes. *J Immunol.* 124(2):724-31, 1980.
Lavelle, et al. Improved methods for the delivery of liposome-sequestered RNA into eucaryotic cells. *Arch Biochem Biophys.* 215(2):486-97, 1982.
Lichtenberg, et al. Liposomes: Preparation, Characterization and Preservation. *Meth Biochem Anal.* 33:337-462, 1988.
Longenecker, et al. Three dimensional structure of mammalian casein kinase I: Molecular basis for phosphate recognition. *J Mol Biol,* 257: 618-631, 1996.
Mannino, et al. Liposome mediated gene transfer. *Biotechniques.* 6(7):682-90, 1988.

Mannino, et al. Liposomes as adjuvants for peptides: Preparation and use of immunogenic peptide-phospholipid complexes. *Liposome Technology,* $2^{nd}$ Edition. 2:167-184, 1993.
Mannino, et al. Lipid matrix-based vaccines for mucosal and systemic immunization. *Pharm Biotechnol.* 6:363-87, 1995.
Mannino, et al. Antigen cochleate preparations for oral and systemic vaccinations. *New Gen Vaccines* $2^{nd}$ ed., Ch 18, pp. 229-239, 1997.
Miller, et al. Vaccination of rhesus monkeys with synthetic peptide in a fusogenic proteoliposome elicits simian immunodeficiency virus-specific CD8+ cytotoxic T lymphocytes. *J Exp Med.* 176(6):1739-44, 1992.
Mori, et al. Immunotargeting of liposomes containing lipophilic antitumor prodrugs. *Pharm Res.* 10(4):507-14, 1993.
Morilla, et al. Development and in vitro characterization of a benznidazole liposomal formulation, *Int J Pharm* 249(1-2): 89-99, 2002.
Osoba, et al. Effect of treatment on health-related quality of life in acquired immunodeficiency syndrome (AIDS)-related *Kaposi's sarcoma*: a randomized trial of pegylated-liposomal doxorubicin versus doxorubicin, bleomycin, and vincristine. *Cancer Invest* 19(6): 573-80, 2001.
Papahadjopolous, et al. Cochleate lipid cylinders formation by fusion of unilamellar vesicles. *Biochim Biophys Acta.* 394(3): 483-491, 1975.
Papahadjopoulos, et al. The use of lipid vesicles for introducing macromolecules into cells. *Prot Turnover Lysosome Funct.* 543-60, 1978.
Parker, et al. In vivo and in vitro antiproliferative effects of antisense interleukin 10 oligonucleotides. *Meth Enzym: Antisense Tech,* Part B 314: 411-29, 1999.
Sanderson, et al. Encapsulation of vancomycin and gentamycin with cationic liposomes for inhibition of growth of *Staphylococcus epidermidis. J Drug Target* 4(3): 181-89, 1996.
Santangelo, et al. Efficacy of oral cochleate-amphotericin B in a mouse model of systemic candidiasis. *Antimicrob. Agents Chemother,* pp. 2356-2360, 2000.
Sundram, et al. General and effecient method for the solution- and solid-phase synthesis of vancomycin carboxaminde derivatives. *J Org Chem* 60:1102-03, 1995.
Wassef, et al. Liposomes as carriers for vaccines. *Immunomethods.* 4(3):217-22, 1994.
Zarif, et al., Amphotericin B cochleates as a novel oral delivery system for the treatment of fungal infection. *Proceedings of the International Symposium on Controlled Release of Bioactive Materials,* Illinois: Controlled Release Society, pp. 964-965, 1999.
Zarif, et al. Antifungal activity of amphotericin B cochleates against *Candida albicans* infection in a mouse model. *Antimicrob. Agents Chemother* 1463-1469, 2000.
Zarif, et al. Cochleates: New lipid based drug delivery system. *J. Liposome Res* 10(4): 523-538, 2000.
Zarif, et al. Elongated supramolecular assemblies in drug delivery. *J. Controlled Rel* 81: 7-23, 2002.
International Search Report for Application No. PCT/US2004/011026.

\* cited by examiner

Formulation of Hydrosoluble Cargo Moieties Into Cochleates:
Trapping method with preformed liposome Soy-PS powder → (Addition of water) → Liposomes → (Addition of the cargo moiety) → Cargo moiety in liposome → (Addition of cation) → Cochleates Survival Data Cochleates using regular trapping method ZnTPP in cochleates Cochleates containing Pyrene DOPE

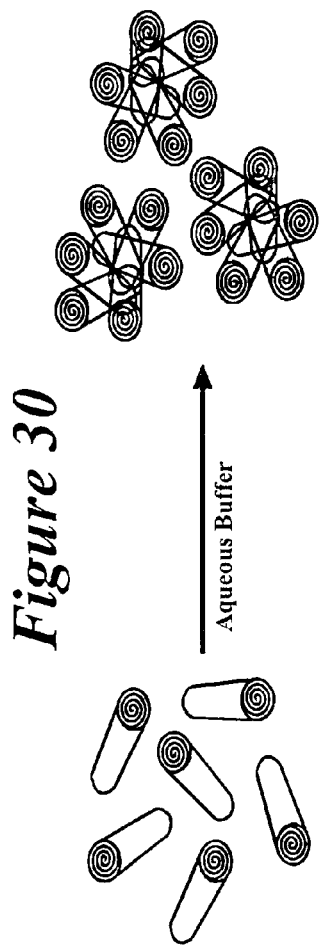
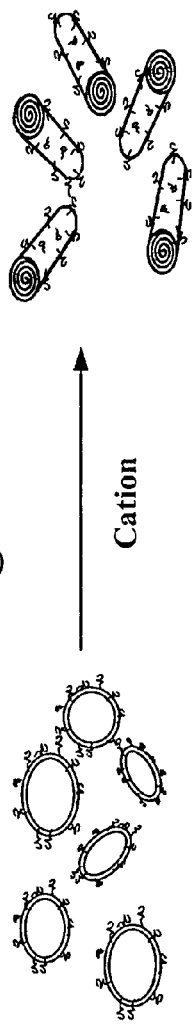
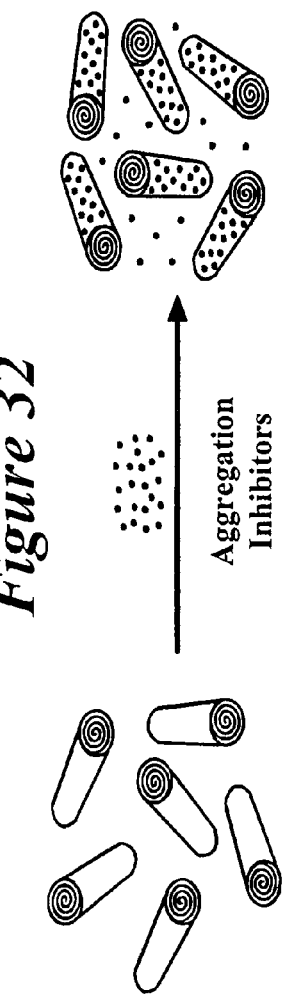

In vitro uptake of Rho-pE-lipid precipitates
Lipid Precipitates Without Aggregation Inhibitor In vitro uptake of Rho-pE-lipid precipitates
Lipid Precipitates With Aggregation Inhibitor

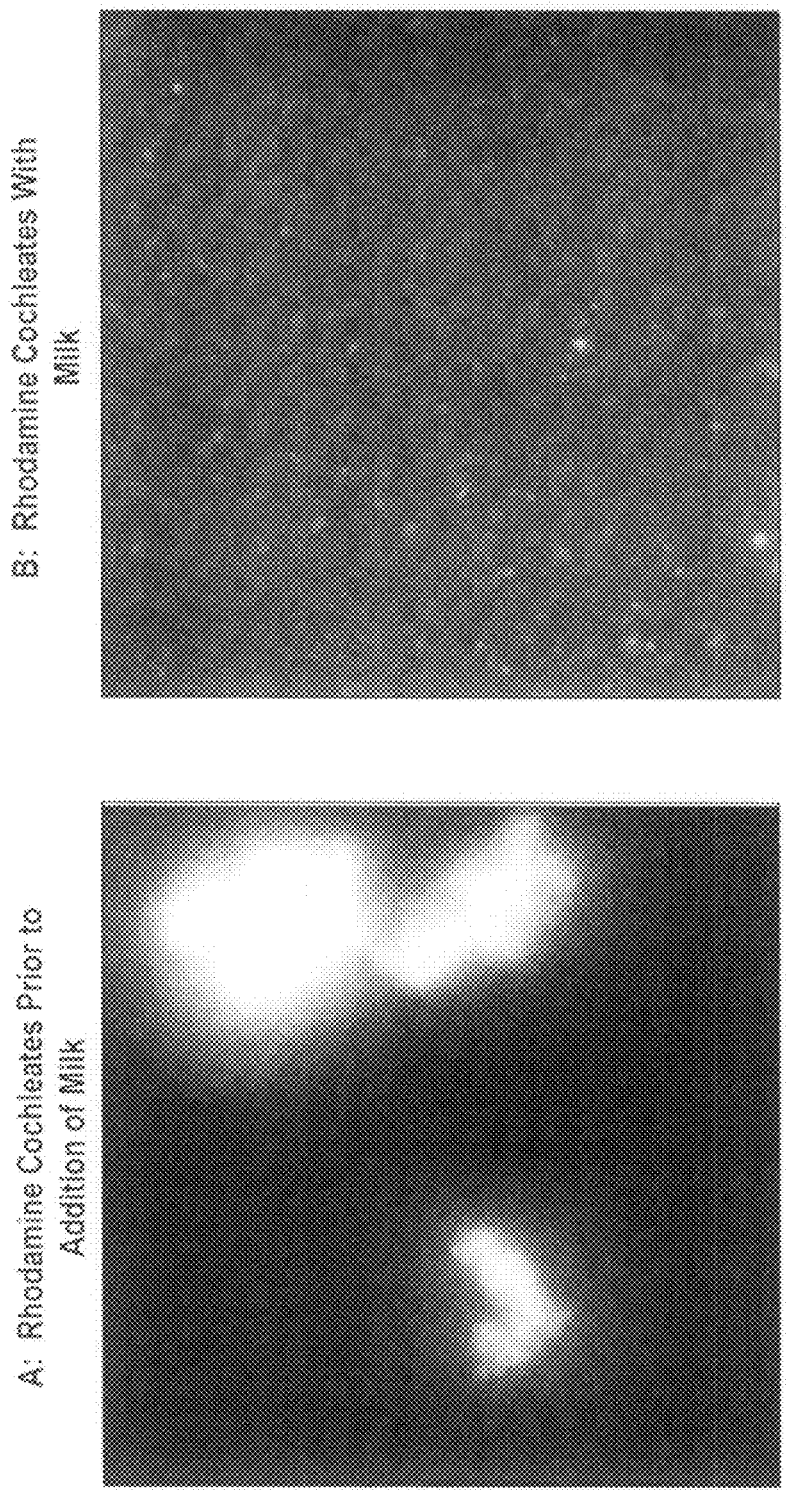

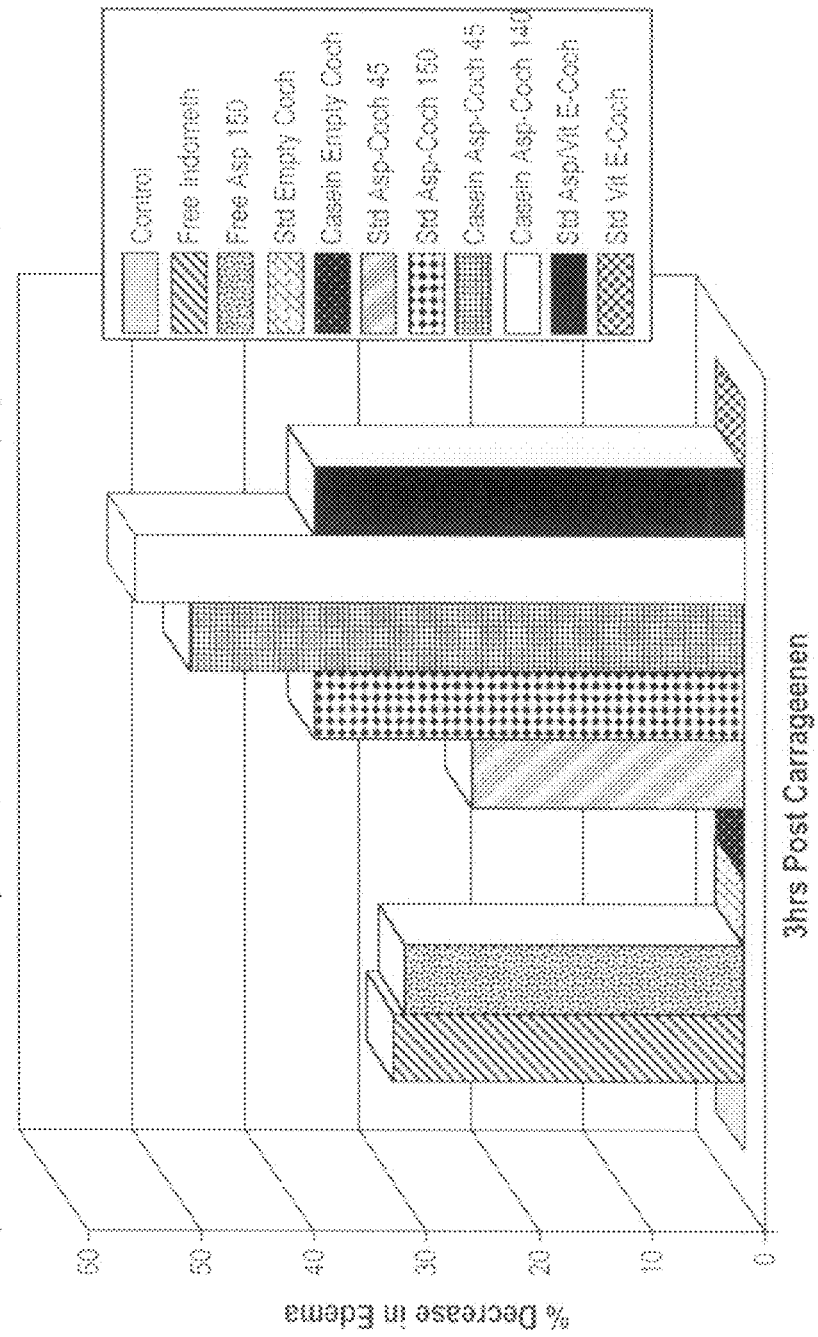

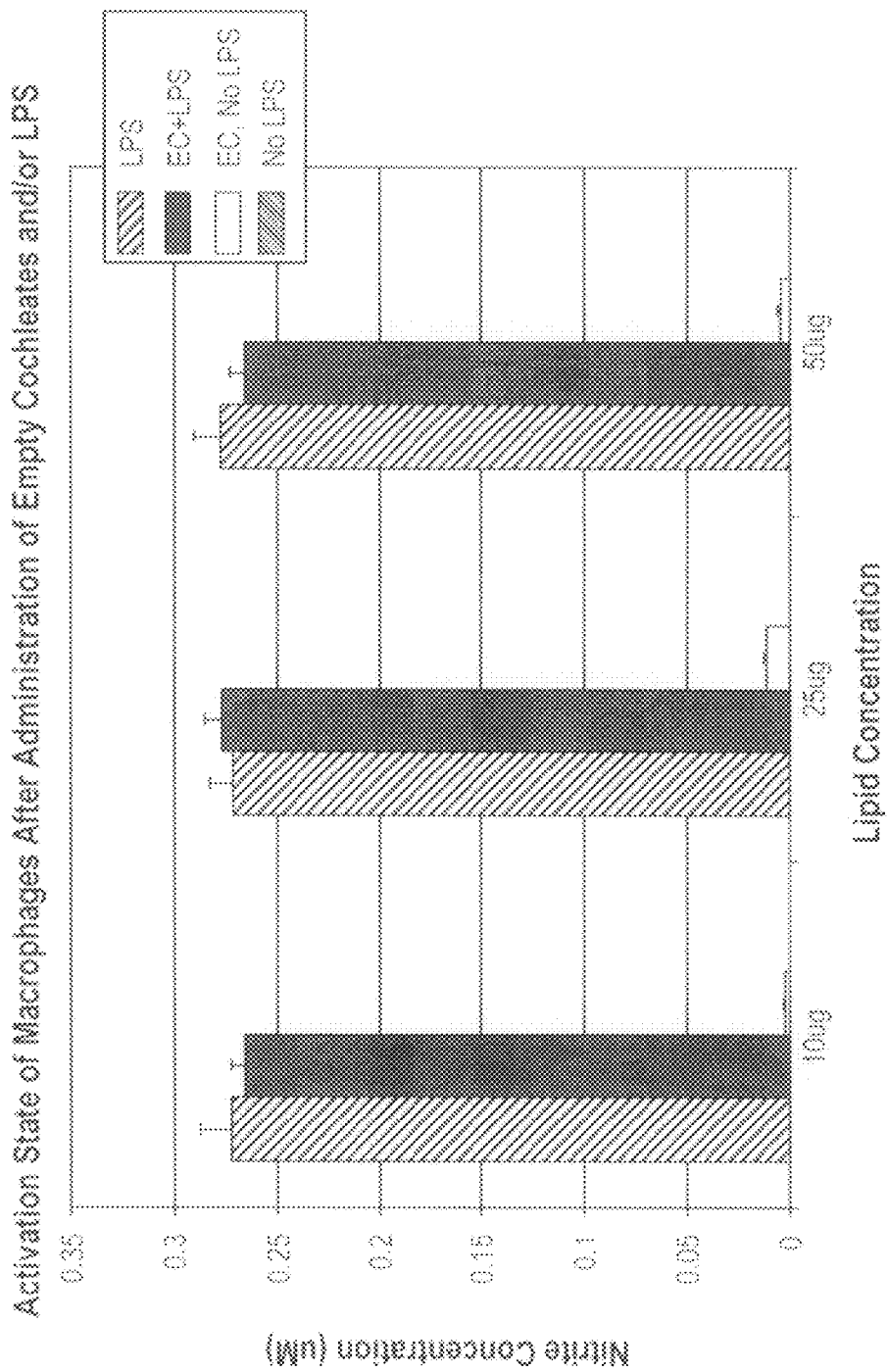

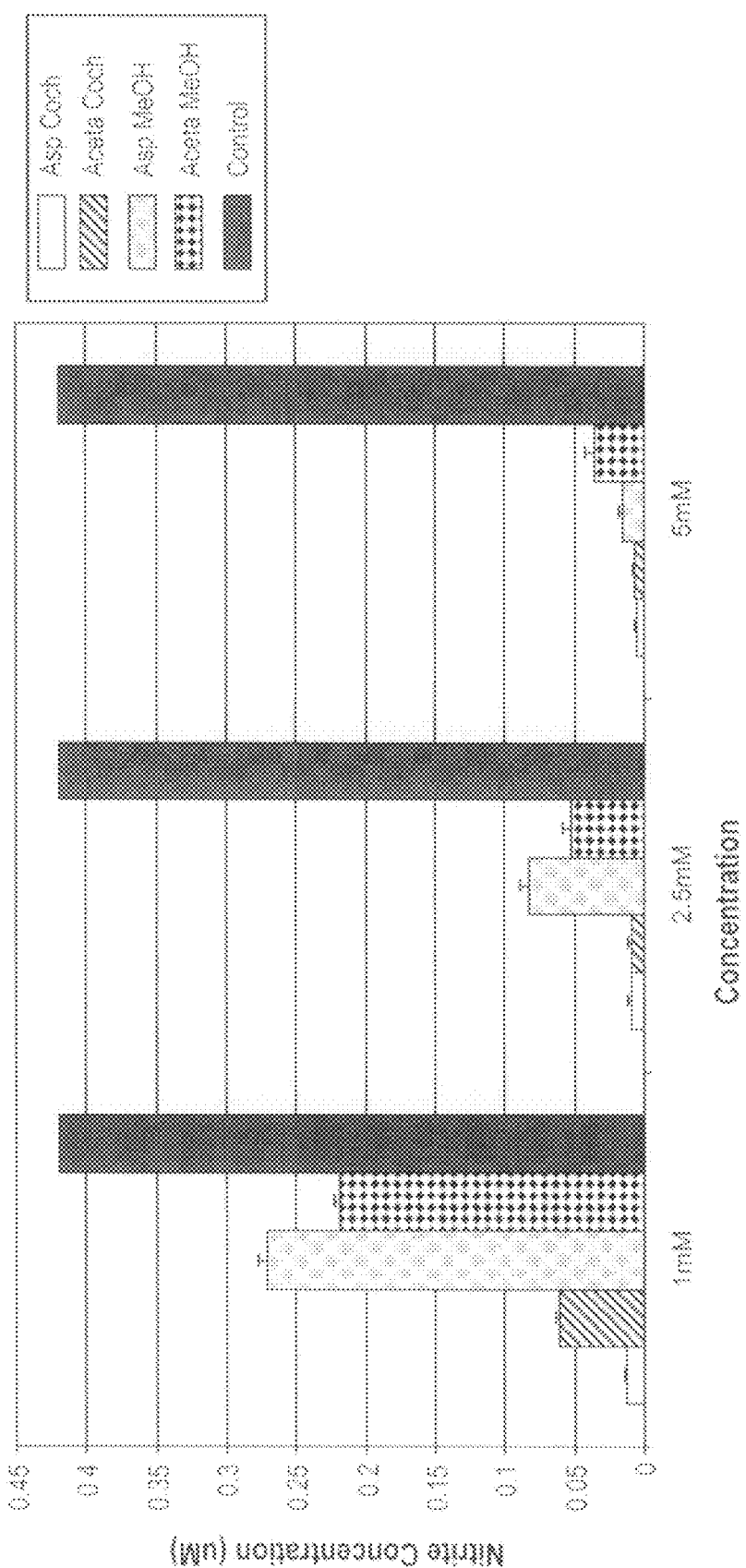

ENCOCHLEATION METHODS, COCHLEATES AND METHODS OF USE

RELATED APPLICATIONS

This application is a continuation of U.S. Ser. No. 10/822,230 filed Apr. 9, 2004, which claims the benefit of and priority to U.S. Provisional Application No. 60/461,483 filed Apr. 9, 2003; U.S. Provisional Application Ser. No. 60/463,076, filed Apr. 15, 2003; U.S. Provisional Application Ser. No. 60/502,557, filed Sep. 11, 2003; U.S. Provisional Application Ser. No. 60/537,252, filed Jan. 15, 2004; U.S. Provisional Application No. 60/499,247 filed Aug. 28, 2003; U.S. Provisional Application No. 60/532,755, filed Dec. 24, 2003; and U.S. Provisional Application No. 60/556,192, filed Mar. 24, 2004. The entire contents of each of the aforementioned applications are hereby expressly incorporated herein by reference in their entireties.

GOVERNMENT SUPPORT

Portions of the subject matter disclosed herein were supported by Federal Grant No. NIAID SBIR PI R43 AI46040-01, awarded by the National Institutes of Health. The U.S. Government may have certain rights in the invention.

TECHNICAL FIELD

The invention generally relates to cochleate delivery vehicles. More specifically, the invention relates to novel methods of making and using cochleates employing a solvent to encochleate a cargo moiety, to cochleates including one or more aggregation inhibitors, and to cochleates including a protonized cargo moiety, divalent cation and negatively charged lipid.

BACKGROUND

The advantages of cochleates are numerous. For example, cochleates are more stable than aqueous structures such as liposomes, they can be stored lyophilized which provides the potential to be stored for long periods of time at room temperatures, they maintain their structure even after lyophilization (whereas liposome structures are destroyed by lyophilization), and they are non-toxic.

Cochleate structures have been prepared first by D. Papahadjopoulos as an intermediate in the preparation of large unilamellar vesicles. U.S. Pat. No. 4,078,052. Methods of making and using cochleates to deliver a variety of molecules have been disclosed, e.g., in U.S. Pat. Nos. 5,994,318 and 6,153,217.

In these methods, prior to precipitation of the cochleates, the material to be encochleated is introduced into liposomes by solubilization of the lipid and material in solvent, removal of the solvent to form a dry lipid film, then by hydration of the lipid and components to be encochleated. Alternatively, material and lipid may be solublized in detergent which may be removed by dialysis or other methods. These steps are time consuming, represent added expense in manufacturing and product costs, and can in some instances affect the activity and/or stability of the encochleated material.

Additionally, cochleates are highly susceptible to aggregation, and thus particle size and particle size distribution can be highly variable and unstable after preparation and removal from the two-phase polymer system. The ability of drugs to be administered via the oral route depends on several factors. The drug typically must be sufficiently soluble in the gastrointestinal fluids in order for the drug to be transported across biological membranes for an active transport mechanism or have a sufficiently small particle size, such that it can be absorbed through the Peyer's Patches in the small intestine and through the lymphatic system. Particle size is an important parameter when oral delivery is to be achieved (see Couvreur P. et al, Adv. Drug Delivery Reviews 10:141-162, 1993). Thus, it would be advantageous to be able to control and stabilize the particle size and particle size distribution of encochleated materials.

There also exists a need for delivery vehicles that can safely and effectively deliver cargo moieties that are poorly absorbed by the body (e.g., weakly basic drugs). For example, aminoglycopeptides (e.g., vancomycin), are poorly absorbed through the GI tract and are difficult to deliver to cells harboring bacteria. Accordingly, in order to administer an effective amount of drug against a bacterial infection, large amounts of drug are ingested to not only account for poor absorption through the GI tract, but also poor delivery to the site of infection. Consequently, a toxic level of drug can accumulate in the GI tract (e.g., in the kidneys) or the blood stream and can lead to serious illness, such as erythematous or urticarial reactions, flushing, tachycardia, and hypotension. Aminoglycosides (e.g., streptomycin and tobramycin) are similarly problematic because of the risk of nephrotoxicity and ototoxicity due to poor absorption, which can lead to acute, renal, vestibular and auditory toxicity. While these drugs can be delivered intravenously to bypass the issue of poor GI tract absorption, uptake by the cells is still problematic. That is, even at high concentrations, aminoglycopeptides and aminoglycosides can not penetrate the cell membrane in order to contact the bacteria. Additionally, echinocandins (e.g., caspofungin), a new, less toxic class of antifungal drugs, still have unwanted side effects and poor oral bioavailability. As such, they are generally administered intravenously.

The present invention addresses each of these drawbacks.

SUMMARY OF THE INVENTION

The present invention provides novel methods of forming cochleates, which methods can be efficiently and easily scaled up. Additionally, the present invention provides an anhydrous cochleate including a protonized cargo moiety, e.g., an aminoglycoside, and methods for making and administering the same. The present invention also provides a cochleate composition which includes an aggregation inhibitor, and methods for making an administering the same.

In one aspect, the present invention provides a method for forming a cargo moiety-cochleate, which includes introducing a cargo moiety to a liposome in the presence of a solvent such that the cargo moiety associates with the liposome and precipitating the liposome to form a cargo moiety-cochleate. The cargo moiety can be any cargo moiety described herein, including protonized cargo moieties. In certain embodiments, the cargo moiety is hydrophobic, hydrophilic, hydrosoluble or amphipathic. In other embodiments, the cargo moiety is an antifungal agent.

In preferred embodiments, the solvent is a water miscible solvent, more preferably the solvent is dimethylsulfoxide (DMSO), a methylpyrrolidone, N-methylpyrrolidone (NMP), acetonitrile, alcohol, ethanol, dimethylformamide (DMF), ethanol (EtOH), tetrahydrofuran (THF), or combinations thereof. In certain embodiments, the method can further involve introducing a solution of the solvent and the cargo moiety to an aqueous liposomal suspension. In preferred embodiments, the solution is introduced dropwise, by continuous flow addition, or in a bolus. Additionally or alternatively, the method can further involve introducing the cargo moiety to a liposomal suspension comprising the solvent. In preferred embodiments, the cargo moiety is introduced as a powder or a liquid. In other embodiments, an antioxidant can be introduced to the liposomal suspension.

In yet other embodiments, the liposomal suspension comprises a plurality of unilamellar and multilamellar liposomes. In preferred embodiments, the method additionally includes the step of filtering or mechanically extruding through a small aperture the liposomal suspension such that a majority of the liposomes are unilamellar.

In still other embodiments, the method further involves precipitating the liposome with a multivalent cation to form a cargo moiety-cochleate. In yet other embodiments, the solvent can be removed from the liposome by dialysis and/or washing.

In some embodiments, the ratio of the lipid to the cargo moiety is between about 0.5:1 and about 20:1. In other embodiments, the ratio of the lipid to the cargo moiety is between about 20:1 and about 20,000:1.

In other embodiments, the method also includes introducing an aggregation inhibitor to the liposomes or the cochleates. The aggregation inhibitor can be any aggregation inhibitor described herein.

In another aspect, the instant invention provides composition which includes one or more cochleates made by any one of the methods described herein.

In yet another aspect, the instant invention provides a composition including an anhydrous cochleate. In one embodiment, the anhydrous cochleate includes a negatively charged lipid, a protonized cargo moiety, and a divalent metal cation. In some preferred embodiments, the protonized cargo moiety is water soluble. In other preferred embodiments, the protonized cargo moiety is a protonized weakly basic cargo moiety. In still other preferred embodiments, the protonized cargo moiety is a multivalent cation.

In particularly preferred embodiments, the protonized cargo moiety is a protonized peptide, a protonized protein, a protonized nucleotide, including a protonized DNA, a protonized RNA, a protonized morpholino, a protonized siRNA molecule, a protonized ribozyme, a protonized antisense molecule, or a protonized plasmid, an aminoglycoconjugate, such as a protonized aminoglycoside or a protonized aminoglycopeptide, including protonized vancomycin, teicoplanin, bleomycin, peptidolglycan, ristocetin, sialoglycoproteins, orienticin, avaporcin, helevecardin, galacardin, actinoidin, gentamycin, netilmicin, tobramycin, amikacin, kanamycin A, kanamycin B, neomycin, paromomycin, neamine, streptomycin, dihydrostreptomycin, apramycin, ribostamycin, spectinomycin, or a protonized echinocandin, including protonized caspofungin, echinocandin B, aculeacin A, micafungin, anidulafungin, cilofungin, pneumocandin and any combinations thereof.

In some embodiments, the ratio of protonized cargo moiety to lipid is about 2:1 by weight. In other embodiments, the ratio of protonized cargo moiety to lipid is between about 4:1 and about 10:1 by weight. In yet other embodiments, the composition can additionally include a second protonized cargo moiety or a cargo moiety. The cargo moiety nay be any of the cargo moieties discussed herein. In a preferred embodiment, the cargo moiety is a nutrient. In a particularly preferred embodiment, the nutrient is Vitamin E. In other preferred embodiments, the divalent metal cation is barium or calcium.

In some embodiments, the composition may include an aggregation inhibitor. Any of the aggregation inhibitors discussed herein may be used.

In some embodiments, the lipid may include a phospholipid. In preferred embodiments, the phospholipid is a dioleoylphosphatidylserine (DOPS) and/or a phosphatidylserine (PS).

In still other embodiments, the present invention provides a method for forming an anhydrous cochleate which includes the step of contacting a negatively charged lipid, a protonized cargo moiety and a divalent metal cation, such that a cochleate is formed.

In some preferred embodiments, the method includes the step of acidifying a cargo moiety to form a protonized cargo moiety. In other preferred embodiments, the method includes the step of adjusting the pH of a solution of the cochleate to maintain a protonized cargo moiety.

In yet other embodiments, the cochleate further comprises a second protonized cargo moiety. In still other embodiments, the divalent metal cation is barium or calcium.

In still other embodiments, an aggregation inhibitor can be introduced to the cochleate. In preferred embodiments, the aggregation inhibitor is introduced to the cochleate before and after the cochleate is formed. In particularly preferred embodiments, the aggregation inhibitor comprises casein and methylcellulose, and the casein is introduced before the cochleate is formed and the methylcellulose is introduced after the cochleate is formed.

In another aspect, the present invention is directed to a cochleate which includes an aggregation inhibitor. In certain embodiments, the present invention is directed to a cochleate composition including a plurality of cochleates and an aggregation inhibitor. In some preferred embodiments, the aggregation inhibitor coats the cochleate. The cochleate composition can further include a cargo moiety, and the cargo moiety can be any of the cargo moieties discussed herein, including protonized cargo moieties. In preferred embodiments, the cochleate includes an antifungal drug. Preferred aggregation inhibitors include proteins, peptides, polysaccharides, milk or milk products, polymers, gums, waxes and/or resins. Particularly preferred aggregation-inhibitors include casein, κ-casein, milk, albumin, serum albumin, bovine serum albumin, rabbit serum albumin, methylcellulose, ethylcellulose, propylcellulose, hydroxycellulose, hydroxymethyl cellulose, hydroxyethyl cellulose, hydroxypropyl cellulose, hydroxypropylmethyl cellulose, polyvinyl pyrrolidone, carboxymethyl cellulose, carboxyethyl cellulose, pullulan, polyvinyl alcohol, sodium alginate, polyethylene glycol, polyethylene oxide, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, carrageenan, carnauba wax, shellac, latex polymers, milk protein isolate, soy protein isolate, and/or whey protein isolate. In particularly preferred embodiments, the aggregation inhibitor is casein, methylcellulose, albumin, serum albumin, bovine serum albumin and/or rabbit serum albumin.

In preferred embodiments, the plurality of cochleates has a mean diameter of less than about 600 nm. In particularly preferred embodiments, the plurality of cochleates has a mean diameter of less than about 500 nm. In other preferred embodiments, the size distribution of the plurality of cochleates is less than about 700 nm. In particularly preferred embodiments, the size distribution of the plurality of cochleates is less than about 550 nm.

In other embodiments, the cochleate further includes an antifungal drug. In preferred embodiments, the antifungal drug is Amphotericin B, miconazole nitrate, ketoconazole, itraconazole, fluconazole, griseofulvin, clotrimazole, econazole, terconazole, butoconazole, oxiconazole, sulconazole, saperconazole, voriconazole, ciclopirox olamine, haloprogin, tolnaftate, naftifine, terbinafine hydrochloride, morpholines, flucytosine, natamycin, butenafine, undecylenic acid, Whitefield's ointment, propionic acid, caprylic acid, clioquinol, nystatin, selenium sulfide, caspofungin, echinocandin B, aculeacin A, micafungin, anidulafungin, cilofungin, and/or pneumocandin. In particularly preferred embodiments, the antifungal drug is Amphotericin B and the aggregation inhibitor comprises methylcellulose. In other particularly preferred embodiments, the composition is a nasal spray.

In yet another aspect, the present invention provides a cochleate composition which includes a first plurality of cochleates with a first mean particle size and a second plurality of cochleates with a second mean particle size, wherein the second mean particle size is different from the first mean particle size. In preferred embodiments, the composition includes at least one cargo moiety. In some particularly preferred embodiments, the first plurality of cochleates and the second plurality of cochleates include the same cargo moiety. In other particularly preferred embodiments, the first plurality of cochleates contains a different cargo moiety than the second plurality of cochleates.

In another embodiment, the cochleate composition can include a third plurality of cochleates with a third mean particle size, wherein the third mean particle size is different from both the first and the second mean particle sizes. In a preferred embodiment, the third plurality of cochleates includes a cargo moiety.

In still another aspect, the present invention provides a method of making a cochleate composition including introducing an aggregation inhibitor to a cochleate composition. In some embodiments, the method includes introducing the aggregation inhibitor to a composition of cochleates. In other embodiments, the method includes introducing the aggregation inhibitor to a composition of aggregated cochleates. In still other embodiments, the method includes introducing the aggregation inhibitor to a composition of liposomes and inducing formation of the cochleate composition. In yet other embodiments, the method includes introducing the aggregation inhibitor to a solution of lipids, forming a liposomes, and inducing formation of the cochleate composition. In preferred embodiments, the aggregation inhibitor is added in an aggregation inhibitor to lipid ratio of between about 4:1 and about 0.1:1 by weight. In particularly preferred embodiments, the aggregation inhibitor is added in an aggregation inhibitor to lipid ratio of about 1:1 by weight. In other particularly preferred embodiments, the aggregation inhibitor is added in an amount suitable for modulating the resulting cochleate to the desired size range.

In yet other embodiments, the present invention includes pharmaceutical compositions including any of the cochleates or cochleate compositions discussed herein.

In still other aspects, the present invention provides methods for treating a subject that can benefit from the administration of a cargo moiety, including protonized cargo moieties, by administering cochleates or cochleate compositions such that the cargo moiety is administered to the subject and such that the subject is treated. Cochleates or cochleate compositions of the invention can be made using any of the methods described herein, including introducing a cargo moiety to a liposome in the presence of a solvent such that the cargo moiety associates with the liposome and precipitating the liposome to form a cargo moiety-cochleate. Any of the cargo moieties and protonized cargo moieties described herein can be administered in the cochleates of the present invention. In another preferred embodiment, the cochleate compositions include an aggregation inhibitor. In particularly preferred embodiments, the aggregation inhibitor is casein, methylcellulose, albumin, serum albumin, bovine serum albumin and/or rabbit serum albumin.

In a preferred embodiment, the cochleates are used for treating a bacterial infection in a host. In other preferred embodiments, the cochleates are used for treating a fungal infection in a host. In particularly preferred embodiments, the host of the bacterial infection or the fungal infection is a cell, a tissue or an organ. In other preferred embodiments, the subject can benefit from administration of a nutrient and the cargo moiety is a nutrient. Administration of cochleates can be used to treat any of the diseases or disorders described herein. In preferred embodiments, the compositions of the invention are used to treat rhinosinusitis.

Administration of cochleates can be by a mucosal route, including oral, intranasal, intraocular, intrarectally, intravaginal, topical, buccal and intrapulmonary, or by a systemic route, including intravenous, intramuscular, intrathecal, subcutaneous, transdermal and intradermal. In a preferred embodiment the administration is intranasal. In another embodiment, the cochleate composition is delivered in the form of a solid, a capsule, a cachet, a pill, a tablet, a gelcap, a crystalline substance, a lozenge, a powder, a granule, a dragee, an electuary, a pastille, a pessary, a tampon, a suppository, a patch, a gel, a paste, an ointment, a salve, a cream, a foam, a lotion, a partial liquid, an elixir, a mouth wash, a syrup, a spray, a nebulae, a mist, an atomized vapor, an irrigant, an aerosol, a tincture, a wash, an inhalant, a solution or a suspension in an aqueous or non-aqueous liquid, and an oil-in-water and/or water-in-oil liquid emulsion. In a preferred embodiment, the cochleate composition is delivered in a form of a spray, a nebulae, a mist, an atomized vapor, an irrigant, an aerosol, a wash, and/or inhalant. In a preferred embodiment, the cochleate composition includes an antifungal drug. The antifungal drug can include any of the antifungal drugs discussed herein In yet another aspect, the present invention involves an article of manufacture which includes packaging material and a lipid contained within the packaging material, wherein the packaging material comprises a label or package insert indicating the use of the lipid for forming cochleates or cochleate compositions of the invention. In preferred embodiments, the article of manufacture can additionally include instructions or guidelines for the formation of cochleates or cochleate compositions, a solvent, a phospholipid, a cargo moiety, a protonized cargo moiety, a multivalent cation, a divalent metal cation, a control cargo moiety, a chelating agent, and/or an aggregation inhibitor. In particularly preferred embodiments, one of the instructions involves mixing a cargo moiety with a solvent and dripping it into a solution of the lipids.

DESCRIPTION OF THE DRAWINGS

FIG. 30 is a schematic diagram of cochleate aggregation in the absence of an aggregation inhibitor.

FIG. 31 is a schematic diagram of an exemplary method of making cochleates of the invention by adding an aggregation inhibitor prior to cochleate formation.

FIG. 32 is a schematic diagram of an exemplary method of making cochleates of the invention by adding an aggregation inhibitor subsequent to cochleate formation.

FIG. 35D is an image of a control composition of cochleates that do not include an aggregation inhibitor.

FIGS. 36A and 36B are two fluorescent images of Rhodamine-labeled cochleates demonstrating the disaggregation of cochleates upon addition of an aggregation inhibitor.

FIG. 38 is a graph comparing the in vivo efficiency of coated (small) and standard (large) aspirin cochleates at different concentrations and with optional additive in reducing edema in rat paws injected with carrageenan.

FIG. 40 is a graph indicating that empty cochleates are immunologically inert in that they have no effect on the production of NO in macrophages.

FIG. 41 is a graph comparing the efficacy of encochleated and unencochleated aspirin and acetaminophen cochleates in inhibiting NO formation.

FIG. 45A depicts vanco-liposomes. FIG. 45B depicts vanco-cochleates that include an aggregation inhibitor (casein). FIG. 45C depicts vanco-cochleates without an aggregation inhibitor. FIG. 45D depicts the cochleates of FIG. 45C upon addition of a chelator (EDTA).

FIG. 48A depicts tobramycin-liposomes. FIG. 48B depicts tobramycin-cochleates that include an aggregation inhibitor (casein). FIG. 48C depicts tobramycin-cochleates without an aggregation inhibitor. FIG. 48D depicts the cochleate of FIG. 48C upon addition of a chelator (EDTA).

DETAILED DESCRIPTION OF THE INVENTION

Figure 1:
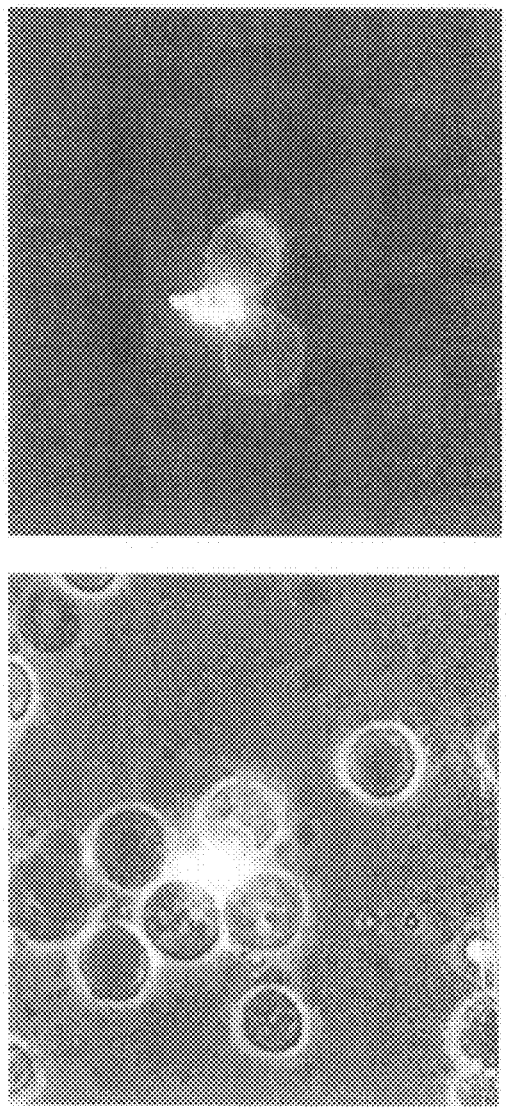
FIG. 1 is two fluorescent images of Rhodamine-labeled cochleates incubated with splenocytes. These images demonstrate a transfer of lipid to the cell membrane, and indicate that a fusion event occurred between the outer layer of the cochleate and the splenocyte cell membrane.

The present invention is based, at least in part, on the discovery of a novel method for the formulation of cochleates and cochleate compositions. These cochleates and cochleate compositions provide all the advantages of conventional cochleates, but are more efficiently made, from a cost and a time perspective. The method generally includes the step of introducing a cargo moiety to a liposome in the presence of a solvent such that the cargo moiety associates with the liposome.

Without wishing to be bound to any particular theory, it is believed that the solvent facilitates association of the cargo moiety with the liposome, e.g., incorporation of a cargo moiety with the liposomal bilayer. For example, in some embodiments, a hydrophobic or amphipathic cargo moiety is dissolved in the solvent prior to addition to an aqueous liposomal suspension. When the solution is added to the liposomal suspension, the solvent is miscible with the water which changes the polarity and decreases the solubility of the cargo moiety in the solution. The cargo moiety then associates, at least in part, with the more hydrophobic environment of the lipid bilayer. For example, the hydrophobic portion of an amphipathic molecule may associate-itself with the lipid bilayer, leaving the remainder of the molecule to reside outside the liposome.

In another embodiment, the cargo moiety is hydrosoluble and/or hydrophilic, and the solvent creates an environment such that the cargo moiety associates with the lipid bilayer (e.g., by ionic attraction to the lipid and/or cation and/or total or partial migration into the bilayer). Additionally or alternatively, the solvent also may facilitate membrane permeation of the cargo moiety (e.g., an alcohol may be employed to enhance the permeability of the liposomal bilayer).

The invention also provides cochleates and cochleate compositions (e.g., pharmaceutical compositions), prepared by the methods of the invention.

The present invention also provides novel cochleates and cochleate compositions that include an aggregation inhibitor. These cochleates and cochleate compositions provide all the advantages of conventional cochleates, and additionally provide a cochleate or cochleate composition having a stable mean particle size and distribution. The cochleates and cochleate compositions can have, e.g., a small particle size, e.g. a mean particle size of less that 600 nm, and/or a narrow particle size range, e.g. less than about 700 nm. Moreover, the composition is stable and does not aggregate with the passage of time.

The invention also provides novel methods of formation of cochleates that allow the cochleates to be produced in any desired size range using a variety of methods. These methods do not require such steps as providing a two-phase system and/or particle size differentiation to obtain a cochleate composition having a mean particle size of less than a micrometer. The methods of the invention can be utilized with any known method of making cochleates.

The present invention also provides a composition for the safe and efficient delivery of cargo moieties in anhydrous cochleates. The invention is based, at least in part, on the discovery that protonized cargo moieties can be precipitated with a negatively charged lipid and a divalent metal cation to form anhydrous, stable and safe compositions for delivery of the moiety. Moreover, protonized cargo moieties can be included in the cochleates at surprisingly high concentrations, if desired.

The cochleates of the invention not only protect the cargo moiety from the host (e.g., from decomposition by proteolytic enzymes in the digestive tract), but also protect the host from the cargo moiety (e.g., preventing damage to vital organs caused by toxic levels of certain cargo moieties). In addition, the cochleates of the invention allow for efficient delivery of the cargo moiety across the digestive tract and to cells, e.g., by fusion and/or cellular uptake. Thus, a lower dosage of cargo moiety can be administered to generate the same beneficial results as compared to conventional preparations, while minimizing the incidence of toxic side effects and/or buildup of cargo moiety in the digestive tract The methods of the invention are superior to those employing conventional liposomal preparations. By way of example, liposome-encapsulated tobramycin has resulted in a low bactericidal activity in vitro. In contrast, anhydrous tobramycin cochleate preparations of the present invention facilitate oral delivery with lower serum levels of drug, thereby lowering the toxicity. In addition, the anhydrous tobramycin cochleates of the invention may be absorbed via the gastrointestinal tract and delivered directly to the site of infection. Moreover, once anhydrous tobramycin cochleates are within the systemic circulation, they can be efficiently accumulated by phagocytes resulting in intracellular delivery of the drug to infected cells.

The invention also provides methods for forming cochleates that include contacting a protonized cargo moiety, a negatively charged lipid and a divalent metal cation.

The invention further provides methods of using the cochleates of the invention, including methods of administration. Finally, the invention provides methods of use, including therapeutic use, and kits directed to the manufacture and use of the cochleates and cochleate compositions of the invention.

In order to more clearly and concisely describe the subject matter of the claims, the following definitions are intended to provide guidance as to the meaning of specific terms used in the following written description, examples and appended claims.

The term "cargo moiety," as used herein, refers to a moiety to be encochleated, and generally does not refer to the lipid and ion employed to precipitate the cochleate. Cargo moieties include any compounds having a property of biological interest, e.g., ones that have a role in the life processes of a living organism. A cargo moiety may be organic or inorganic, a monomer or a polymer, endogenous to a host organism or not, naturally occurring or synthesized in vitro and the like.

As used herein, the terms "cochleate," "lipid precipitate" and "precipitate" are used interchangeably to refer to a lipid precipitate component that generally includes alternating cationic and lipid bilayer sheets with little or no internal aqueous space, typically stacked and/or rolled up, wherein the cationic sheet is comprised of one or more multivalent cations. Additionally, the term "encochleated" means associated with the cochleate structure.

The term "protonized cargo moiety" refers to a protonizable cargo moiety that has been protonized. "Protonizable" refers to the ability to gain one or more protons. The protonizable cargo moiety can be weakly basic, and can be protonized by acidification or addition of a proton. Additionally or alternatively, the protonizable cargo moiety can be neutral or weakly acidic and can be protonized in the same manner. Thus, the protonizable cargo moiety can be an anionic or a neutral cargo moiety, which is rendered cationic by protonization, or the protonizable cargo moiety can be cationic, and be rendered more cationic upon protonization. The cargo moiety can also be provided protonized. Optionally, the protonized state can be induced, e.g., by acidification or other methods, as described herein. Protonization renders the cargo moiety cationic or increases the valency of a cargo moiety that is already cationic, e.g., from monovalent to divalent or trivalent.

The term "protonization," as used herein, refers to the process of increasing the valency of a cargo moiety. "Protonized" refers to a cargo moiety that has undergone protonization. Thus, valency can be increased, e.g. from 0 to 1, from 1 to 2, from 2 to 3, from 3 to 4, or any combination thereof, e.g., from 0 to 3. Any method to increase valency, e.g., increasing pH, can be used to protonize a cargo moiety.

The term "weakly basic cargo moiety" refers to cargo moieties that, at neutral pH, have the ability to accept protons. That is, weakly-basic cargo moieties are capable of being rendered cationic or more cationic by protonization. As such, weakly basic cargo moieties can be anionic or neutral, and be rendered cationic by protonization. Alternatively, weakly basic cargo moieties can be cationic, and can be rendered more cationic, i.e., polycationic, by protonization.

The term "weakly acidic cargo moiety" refers to cargo moieties that, at neutral pH, have the ability to give up protons. "Protonizable weakly acidic cargo moieties," due to their weak acidity, have the ability to accept protons at decreased pH.

"Aminioglycoconjugates," as used herein, refer to compounds that include an amino sugar or carbohydrate covalently linked with another moiety. Exemplary subgroups of aminoglycoconjugates include, but are not limited to, aminoglycoproteins, aminoglycosides, glycosaminoglycans, and aminoglycopeptides.

"Aminoglycopeptides" are compounds that include an amino sugar or carbohydrate covalently linked to one or more peptides, including synthetic or chemically modified derivatives. Aminoglycopeptides include, but are not limited to vancomycin, teicoplanin, bleomycin, peptidolglycan, ristocetin, sialoglycoproteins, orienticin, avaporcin, helevecardin, galacardin, and actinoidin. Derivatives of these compounds also are included, e.g., those provided by reductive alkylation of reactive amines. See, Sundram et al., J. Org. Chem. 60:1102-03 (1995). U.S. Pat. Nos. 4,639,433, 4,643,987, and 4,698,327, teach N-alkyl and N-acyl derivatives of vancomycin. European Patent Nos. 435 503A1 and 667 353 A1, described reductive alkylations of a variety of aminoglycopeptides including vancomycin and orienticin A.

"Aminoglycosides" are compounds that include at least two amino sugars linked by glycoside bonds to a streptidine or a 2-deoxystreptamine or their analogs. Analogs are meant to include aminoglycosides modified, e.g., to increase resistance to enzyme cleavage. Such derivatives (e.g., amikacin, a semisynthetic derivative of kanamycin), are necessary for treatment of individuals or populations that have built up resistance to other aminoglycosides, and all such derivatives developed presently or in the future are aminoglycosides that fall within the scope of the present invention. Analogs also are meant to include the structurally related aminocyclitols (e.g., spectinomycin). Aminoglycosides include, but are not limited to, gentamicin, netilmicin, tobramycin, amikacin, kanamycin A, kanamycin B, neomycin, paromomycin, neamine, streptomycin, dihydrostreptomycin, apramycin, ribostamycin, and spectinomycin. Aminoglycosides can optionally be grouped as streptomycins (e.g., streptomycin and dihydrostreptomycin), kanamycins (e.g., kanamycin, amikacin, tobramycin), gentamicins (e.g., gentamicin and netilmicin), and neomycins. Apramycin and specinomycin are aminoglycosides typically used by veterinarians to treat non-human animals.

"Echinocandins" are large lipopeptide molecules, which are active as antifungal agents. Echinocandins act by inhibiting glucan synthesis via inhibition of 1,3-beta-D-glucan synthase. This interferes with the synthesis of chitin, an important cell-wall component, and results in fungal cell lysis. These drugs have fungicidal activity against a vast species of fungi, e.g., *Candida* and *Aspergillus*. Examples of echinocandins include, but are not limited to, caspofungin, echinocandin B, aculeacin A, micafungin, anidulafungin, cilofungin, and pneumocandin. Any antifungal molecule with an echinocandin core structure is meant to be included.

As used herein, the term "peptide" refers to a compound containing two or more amino acids, such as a protein. The term "nucleotide" refers to one or more purine or pyrimidine molecules attached to a backbone. The backbone can be a sugar-phosphate backbone, or a modified backbone, e.g., a morpholino backbone. The terms "protonized peptide" and "protonized nucleotide" are meant to include any peptide or nucleotide that can be rendered divalent or polyvalent.

"Carbohydrates" include any carbohydrate including those that include one or more monosaccharides, disaccharides, oligosaccharides or polysaccharides, and their derivatives.

Cochleates

Cochleate delivery vehicles represent a unique technology platform suitable for the oral and systemic administration of a wide variety of molecules with important therapeutic biological activities, including drugs, genes, and vaccine antigens. Miller et al., J Exp Med 176:1739-1744 (1992); Gould-Fogerite and Mannino, J. Liposome Res 6(2):357-79 (1996); Mannino and Gould-Fogerite, New Generation Vaccines, ch. 18, pp 229-39 (Marcel Dekker, New York, N.Y., Myron M. Levine, Ed. 2nd ed. 1997); Gould-Fogerite et al., Advanced Drug Delivery Reviews 32(3):273-387 (1998); Gould-Fogerite and Mannino, Methods in Molecular Medicine, Vaccine Adjuvants: Preparation Methods and Research Protocols pp 179-196 (Humana Press, Totowa 1999); Gould-Fogerite et al., J Liposome Research 10(4): 339-358 (2000); U.S. Pat. No. 5,834,015; Gould-Fogerite et al., Gene 84:429-438 (1989); Zarif et al., J. Liposome Research-60(4), 523-538 (2000); Zarif et al., Antimicrobials Agents and Chemotherapy 44(6):1463-1469 (2000); Santangelo et al., Antimicrobials Agents and Chemotherapy 44(9):2356-2360 (2000); Parker et al., Methods in Enzymology: Antisense Technology, Part B, 314: 411-29 (M. Ian Phillips, Ed., 1999).

Cochleate formulation technology is particularly applicable to macromolecules as well as small molecule drugs that are hydrophobic, positively charged, negatively charged and/or possess poor oral bioavailability. Proof-of-principle studies for cochleate mediated oral delivery of macromolecules as well as small molecule drugs is being carried out in appropriate animal models with well established, clinically important drugs which currently can only be effectively delivered by injection (e.g., antifungal agents such as amphotericin B).

The cochleate structure provides protection from degradation for associated "encochleated" moieties. Divalent cation concentrations in vivo in serum and mucosal secretions are such that the cochleate structure is maintained. Hence, the majority of cochleate-associated molecules are present in the inner layers of a primarily solid, non-aqueous, stable, impermeable structure. Since the cochleate structure includes a series of solid layers, components within the interior of the cochleate structure remain substantially intact, even though the outer layers of the cochleate may be exposed to harsh environmental conditions or enzymes. In an exemplary method of cochleate formation, liposomes, which include negatively charged lipids associated with a cargo moiety, are exposed to a cation, e.g., calcium, that interacts with the liposomes to displace water and condense the lipid. The cation/lipid sheets "roll-up" and/or stack against each other to minimize contact with water, which provides an environment for the encochleated molecule that is substantially free of water. This structure provides protection to encochleated molecules from digestion in the stomach.

The cochleate interior is primarily free of water and resistant to penetration by oxygen. Oxygen and water are primarily responsible for the decomposition and degradation of cargo moieties (e.g., drugs and nutrients), which leads to reduced shelf-life. Accordingly, encochleation also imparts extensive shelf-life stability. For example, for DNA vaccine-cochleates, the encochleation efficiency, the percentage of supercoiled versus relaxed plasmid, and immunogenicity are equivalent to fresh preparations for more than one year.

With respect to storage, cochleates can be stored in cation-containing buffer, or lyophilized or otherwise converted to a powder, and stored at room temperature. If desired, the cochleates also can be reconstituted with liquid prior to administration. Cochleate preparations have been shown to be stable for more than two years at 4° C. in a cation-containing buffer, and at least one year as a lyophilized powder at room temperature.

As used herein, the term "multivalent cation" refers to a divalent cation or higher valency cation, or any compound that has at least two positive charges, including mineral cations such as calcium, barium, zinc, iron and magnesium and other elements capable of forming ions or other structures having multiple positive charges capable of chelating and bridging negatively charged lipids. Additionally or alternatively, the multivalent cation can include other multivalent cationic compounds, e.g., cationic or protonized cargo moieties. The term "divalent metal cation," as used herein, refers to a metal having two positive charges.

The lipid employed in the present invention preferably includes one or more negatively charged lipids. As used herein, the term "negatively charged lipid" includes lipids having a head group bearing a formal negative charge in aqueous solution at an acidic, basic or physiological pH, and also includes lipids having a zwitterionic head group.

The cochleates of the invention also can include non-negatively charged lipids (e.g., positive and/or neutral lipids). Preferably, a majority of the lipid is negatively charged. In one embodiment, the lipid is a mixture of lipids, comprising at least 75% negatively charged lipid. In another embodiment, the lipid includes at least 85% negatively charged lipid. In other embodiments, the lipid includes at least 90%, 95% or even 99% negatively charged lipid. All ranges and values between 60% and 100% negatively charged lipid are meant to be encompassed herein.

The negatively charged lipid can include soy-based lipids. Preferably, the lipid includes phospholipids, such as soy-based phospholipids. The negatively charged lipid can include phosphotidyl serine (PS), dioleoylphosphatidylserine (DOPS), phosphatidic acid (PA), phosphatidylinositol (PI), and/or phosphatidyl glycerol (PG) and or a mixture of one or more of these lipids with other lipids. Additionally or alternatively, the lipid can include phosphatidylcholine (PC), phosphatidylethanolamine (PE), diphosphotidylglycerol (DPG), dioleoyl phosphatidic acid (DOPA), distearoyl phosphatidylserine (DSPS), dimyristoyl phosphatidylserine (DMPS), dipalmitoyl phosphatidylglycerol (DPPG) and the like.

The lipids can be natural or synthetic. For example, the lipid can include esterified fatty acid acyl chains, or organic chains attached by non-ester linkages such as ether linkages (as described in U.S. Pat. No. 5,956,159), disulfide linkages, and their analogs.

In one embodiment the lipid chains are from about 6 to about 26 carbon atoms, and the lipid chains can be saturated or unsaturated. Fatty acyl lipid chains useful in the present invention include, but are not limited to, n-tetradecanoic, n-hexadecanoic acid, n-octadecanoic acid, n-eicosanoic acid, n-docosanoic acid, n-tetracosanoic acid, n-hexacosanoic acid, cis-9-hexadecenoic acid, cis-9-octadecenoic acid, cis, cis-9,12-octadecedienoic acid, all-cis-9,12,15-octadecetrienoic acid, all-cis-5,8,11,14-eicosatetraenoic acid, all-cis-4,7,10,13,16,19-docosahexaenoic acid, 2,4,6,8-tetramethyl decanoic acid, and lactobacillic acid, and the like.

The cochleates of the invention can further include additional compounds known to be used in lipid preparations, e.g., cholesterol, and/or pegylated lipid. Pegylated lipid includes lipids covalently linked to polymers of polyethylene glycol (PEG). PEG's are conventionally classified by their molecular weight, thus PEG 6,000 MW, e.g., has a molecular weight of about 6000. Adding pegylated lipid generally will result in an increase of the amount of compound (e.g., peptide, nucleotide, and nutrient) that can be incorporated into the cochleate. An exemplary pegylated lipid is dipalmitoylphosphatidylehtanolamine (DPPE) bearing PEG 5,000 MW.

Methods of Forming Cochleates

In one aspect, the invention provides methods for forming cochleates. Any known method can be used to form cochleates, including but not limited to those described in U.S. Pat. Nos. 5,994,318 and 6,153,217, the entire disclosures of which are incorporated herein by this reference.

In one embodiment, the method generally includes introducing a cargo moiety to a lipid in the presence of a solvent, adding an aqueous solution to form liposomes, and precipitating to form a cochleate.

In a preferred embodiment, the method generally includes introducing a cargo moiety to a liposome in the presence of a solvent such that the cargo moiety associates with the liposome, and precipitating the liposome to form a cargo moiety-cochleate.

The step of introducing a cargo moiety to a liposome in the presence of a solvent can be achieved in a variety of ways, all of which are encompassed within the scope of the present invention. In one embodiment, the cargo moiety is introduced by introducing a solution of the solvent and the cargo moiety to the liposome. Preferably, the liposome is in a liposomal suspension, preferably, an aqueous liposomal suspension. In a preferred embodiment, the solution is introduced to the liposome by dropwise addition of the solution. In other embodiments, the solution can be added by continuous flow or as a bolus. In addition the solution may be introduced to dried lipid, with water added before, after or with the solution.

In another embodiment, the cargo moiety is introduced to the liposome prior to or after the solvent. For example, the cargo moiety may be introduced to a liposomal suspension that includes the solvent. The mixture can then be agitated, mixed, vortexed or the like to facilitate association of the cargo moiety with the liposome. The cargo moiety introduced may be in a powder or a liquid form.

An antioxidant (e.g., Vitamin E) may also be employed in the methods of the present invention. It can be introduced with the cargo moiety or with the liposome. Preferably, it is incorporated into the liposomal suspension or a solution of the cargo moiety and solvent.

The liposome may be prepared by any known method of preparing liposomes. Thus, the liposomes may be prepared for example by solvent injection, lipid hydration, reverse evaporation, freeze drying by repeated freezing and thawing. The liposomes may be multilamellar (MLV) or unilamellar (ULV), including small unilamellar vesicles (SUV). The concentration of lipid in these liposomal solutions can be from about 0.1 mg/ml to 500 mg/ml. Preferably, the concentration of lipid is from about 0.5 mg/ml to about 50 mg/ml, more preferably from about 1 mg/ml to about 25 mg/ml.

The liposomes may be large unilamellar vesicles (LUV), stable plurilamellar vesicles (SPLV) or oligolamellar vesicles (OLV) prepared, e.g., by detergent removal using dialysis, column chromatography, bio beads SM-2, by reverse phase evaporation (REV), or by formation of intermediate size unilamellar vesicles by high pressure extrusion. Methods in Biochemical Analysis, 33:337 (1988). Liposomes made by all these and other methods known in the art can be used in practicing this invention.

In a preferred embodiment at least majority of the liposomes are unilamellar. The method can further include the step of filtering a liposomal suspension and/or mechanically extruding the suspension through a small aperture that includes both MLV and ULV liposomes, such that a majority of the liposomes are ULV. In preferred embodiments, at least 70%, 80%, 90% or 95% of the liposomes are ULV.

The method is not limited by the method of forming cochleates. Any known method can be used to form cochleates from the liposomes of the invention (i.e., the liposomes associated with the cargo moiety). In a preferred embodiment, the cochleate is formed by precipitation. The liposome can be precipitated with a multivalent cation to form a cargo moiety-cochleate. The multivalent cation can consist entirely or consist essentially of a cationic metal, including, but not limited to calcium, magnesium, barium, zinc, and/or iron. Additionally or alternatively, the multivalent cation can include other multivalent cationic compounds. As used herein, the term "multivalent" refers to ions having a valency of at least 2, e.g., divalent, trivalent, etc.

Any suitable solvent can be employed in connection with the present invention. Solvents suitable for a given application can be readily identified by a person of skill in the art. Preferably, the solvent is an FDA acceptable solvent.

The solvent can be an organic solvent or an inorganic solvent. In one embodiment, the solvent is a water miscible solvent. Suitable solvents include but are not limited to dimethylsulfoxide (DMSO), a methylpyrrolidone, N-methylpyrrolidone (NMP), acetonitrile, alcohols, e.g., ethanol (EtOH), dimethylformamide (DMF), tetrahydrofuran (THF), and combinations thereof. In general, the cargo moiety concentration within the solvent is between about 0.01 mg/ml and 200 mg/ml. Preferably, the cargo moiety concentration is between about 0.05 mg/ml and about 100 mg/ml, more preferably between about 0.1 mg/ml and 20 mg/ml.

The solvent can optionally be removed, e.g., before the formation of liposomes, at the liposome stage and/or after the cochleates are formed. Any known solvent removal method can be employed. For example, solvent may be removed from the liposomal suspension by tangential flow and/or filtration and/or dialysis, or from the cochleates by washing, filtration, centrifugation, and/or dialysis. The cochleates can be washed, e.g., with buffer or water, optimally with calcium or another cation.

Utilizing the methods of the invention a wide range of lipid to cargo moiety ratios can be achieved. Different ratios can have varying biological activity. The amount of cargo moiety incorporated into the cochleates can be varied as desired. The optimal lipid:cargo moiety ratio for a desired purpose can readily be determined without undue experimentation. The cochleates can be administered to the targeted host to ascertain the nature and tenor of the biologic response to the administered cochleates. It is evident that the optimized ratio for any one use may range from a high ratio to a low ratio to obtain maximal amount of cargo moiety in the cochleates. All ratios disclosed herein are w/w, unless otherwise indicated. In one embodiment, the ratio of lipid to cargo moiety is between about 10,000:1 and 1000:1. Ratios in this range may be suitable when it is desired to administer small amounts of the moiety, (e.g., in the case of administration of radioactive agents or highly active, rare or expensive molecules). In another embodiment, the ratio is between about 8,000:1 and 4,000:1, e.g., about 6,000:1. Such a ratio may be suitable, e.g., in delivering porphyrins. In yet another embodiment, the ratio is between about 5,000:1 and 50:1. In yet another embodiment, the ratio of the lipid to the cargo moiety is between about 20:1 and about 0.5:1. In another embodiment, the ratio of the lipid to the cargo moiety is between about 1:1 and about 10:1. Such a ratio may be suitable, e.g., for delivery of an antifungal agent. In yet another embodiment, the ratio of lipid to the cargo moiety is about 2:1, about 3:1, or between about 1.5:1 and 3.5:1. All individual values and ranges between about 0.25:1 and about 40,000:1 are within the scope of the invention. Further values also are within the scope of the invention. The cochleate formulations also can be prepared both with and without targeting molecules (e.g., fusogenic molecules, such as Sendai virus envelope polypeptides), to target specific cells and/or tissues.

In some embodiments, the cargo moiety is hydrophobic. In others, it is amphipathic. In still others, it is hydrophilic and/or hydrosoluble. Exemplary cargo moieties are disclosed below.

In preferred embodiments, hydrophobic cargo moiety cochleates (e.g., beta-carotene cochleates) are formed by introducing a hydrophobic cargo moiety to a liposome in the presence of a solvent such that the hydrophobic cargo moiety associates with the liposome, and precipitating the liposome to form a hydrophobic cargo moiety-cochleate. In particularly preferred embodiments, the loading of hydrophobic cargo moiety in the cochleate is considerably higher than the loading observed when cochleates are formed using conventional methods, i.e., those described in U.S. Pat. No. 5,994,318.

Formation of the cochleates of the invention in the above methods involves crystallization of multivalent cation with negatively charged lipids. It is evident, therefore, that all of the parameters that govern crystallization, e.g., temperature, lipid concentration, multivalent cation concentrations, rate of cation addition, pH and rate of mixing, can be utilized to regulate cochleate formation. In certain embodiments, ionic conditions can be created or adjusted to affect the efficiency of the association and/or the encochleation of the cargo moiety. For example, increasing the salt concentration in a liposomal suspension can render the environment less hospitable to a hydrophobic or amphipathic cargo moiety, thereby increasing liposome and cochleate loading efficiency. Ionic conditions can also affect the ultimate structure of the cochleate generated. High loads of a cargo moiety can also affect the highly ordered structure observed in cochleates formed, e.g., exclusively from calcium and PS. Additionally or alternatively, pH conditions can be created or adjusted to affect the loading and structure of the resulting cochleates. Such variations can readily be manipulated by the skilled practitioner using no more than the instant specification and routine experimentation. In addition, because a cochleate is highly thermodynamically stable, once a cochleate formulation method is developed for a given product, the end product can be made predictably and reliably.

Accordingly, in another aspect, the present invention provides methods of making anhydrous cochleates with protonized cargo moieties. The method generally includes the step of contacting a negatively charged lipid, a protonized cargo moiety and a divalent metal cation. Without wishing to be bound by any particular theory, it is believed that the negatively charged lipid forms an ionic interaction with the cationic protonized-cargo moiety. The divalent metal cation then precipitates the lipid and protonized cargo moiety to form an anhydrous cochleate.

In a preferred embodiment, the protonized cargo moiety is introduced to the negatively charged lipid. A divalent metal cation is then added to the lipid-protonized cargo moiety mixture in order to form anhydrous cochleates. The divalent metal cation can be, e.g., calcium, barium, etc. In particularly preferred embodiments, the divalent metal cation is capable of inducing the formation of an anhydrous cochleate. In other particularly preferred embodiments, the divalent metal cation is calcium.

In one embodiment, liposomes are formed that include negatively charged lipid using known methods, and the protonized cargo moiety is added prior to, during or after formation of the liposomal suspension. Alternatively, the protonized cargo moiety is introduced to a preformed liposomal suspension, e.g., as a solid or in an aqueous or organic solution.

The method can further include the step of protonizing the cargo moiety prior to or during the formation of the cochleate, e.g., by acidification. Any known method of acidification can be employed. For example, a weakly basic cargo moiety can be protonized with acidic aqueous buffer. A buffer is chosen based upon the $pK_a$ of the cargo moiety. A cargo moiety with a lower $pK_a$ would necessitate a buffer with a lower pH range than that of a cargo moiety with a higher $pK_a$. Thus, for caspofungin, with $pK_a$, values of 5.1, 8.7, 9.7 and 10.7, a buffer with a pH range of between 4.5 and 5.5 would be sufficient to maintain its multivalency. Buffers with a pH range suitable for acidification can readily be identified by the skilled practitioner based upon the cargo moiety being protonized. Suitable buffers include low molecular weight buffers having an acidic $pK_a$, e.g., amino acids and TES. Acidic buffers are known in the art, and identification of a variety of acidic buffers would require no more than routine experimentation by one of ordinary skill in the art. Alternatively, the weakly basic cargo moiety can be protonized by slow addition of an acid, e.g., hydrochloric acid, to an aqueous solution of lipid and weakly basic cargo moiety.

In still other embodiments, the protonizable cargo moiety has more than one $pK_a$ value. In preferred embodiments, the pH is lowered to below the highest $pK_a$ value. In other preferred embodiments, pH is lowered to below the second highest pK$_a$ value. In other preferred embodiments, the pH is lowered to below the third, fourth, fifth or even sixth highest pK$_a$ value. In yet other preferred embodiments, the pH is lowered to below the lowest pK$_a$ value.

Optionally, the cargo moiety can be protonized in the lipid-cargo moiety mixture, e.g., by lowering the pH or introducing the cargo moiety to a suspension of lipids at a low pH. Because of its cationic nature, the protonized cargo moiety tends to associate with the negatively charged surface of the liposome bilayers.

In yet other embodiments, the cargo moieties can be protonized prior to incorporation into the cochleates. For example, they can be obtained or purchased protonized from the manufacturer. Additionally or alternatively, they can be protonized, isolated as a protonized cargo moiety, and subsequently incorporated into a cochleate at a suitable pH. A suitable pH is a pH that allows the cargo moiety to remain protonized, and can be readily determined by the skilled artisan.

In other embodiments, the pH of the resultant anhydrous cochleates in solution can be adjusted using, e.g., acid. Without wishing to be bound by any particular theory, it is believed that this would help to maintain the protonized cargo moiety within the cochleate structure.

In another aspect, the present invention generally is directed to methods of making cochleates that include an aggregation inhibitor. The aggregation inhibitor can be introduced prior to, during or after formation of cochleates. That is, the aggregation inhibitor can be added to the lipid-cargo moiety solution, to the liposomal solution or to the precipitated cochleate. For example, in one embodiment, the aggregation inhibitor is introduced to a liposomal suspension from which cochleates will subsequently be formed (e.g., by addition of cation or dialysis). That is, the aggregation inhibitor may be introduced prior to formation of liposomes, e.g., it may be added to dried lipid prior to suspension or added directly to a liposomal suspension, before of after addition of a cargo moiety. In such embodiments, the cochleates may be initially formed in the desired size range and aggregation thereafter prevented by the presence of the aggregation inhibitor.

In other embodiments, the methods of the invention can include the step of introducing an aggregation inhibitor to a cochleate composition. For example, the method can further include forming cochleates (prior to introducing the aggregation inhibitor). The method can include providing cochleates already formed, e.g., cochleates obtained from a supplier. The method can further include the step of disaggregating cochleates by adding an aggregation inhibitor to aggregated cochleates.

In still other embodiments, aggregated cochleates may be disaggregated using alternative disaggregation methods, e.g., homogenization, and an aggregation inhibitor can be introduced in order to prevent reaggregation.

In yet another embodiment, the aggregation inhibitor can be introduced during the formation of the cochleate, e.g., it can be added with the cation or during dialysis.

In a preferred embodiment, the aggregation inhibitor is added in an amount suitable for modulating the resulting cochleate to the desired size.

The method can include forming cochleates with any or all of the optional ingredients disclosed herein. For example, the cochleates can include additional cationic compounds, protonized cargo moieties, non-negative lipids, and/or aggregation inhibitors.

Any of the methods described herein can be utilized to produce anywhere from about 1 mg to about 500 g of cochleates in one batch. A smaller batch may be preferred in a laboratory setting where characterization of cochleates is desired. On the other hand, larger batches may be preferred in a manufacturing setting where mass production is desired. Preferably, larger batches are at least 50 g, and more preferably at least 75 g.

Figure 2:
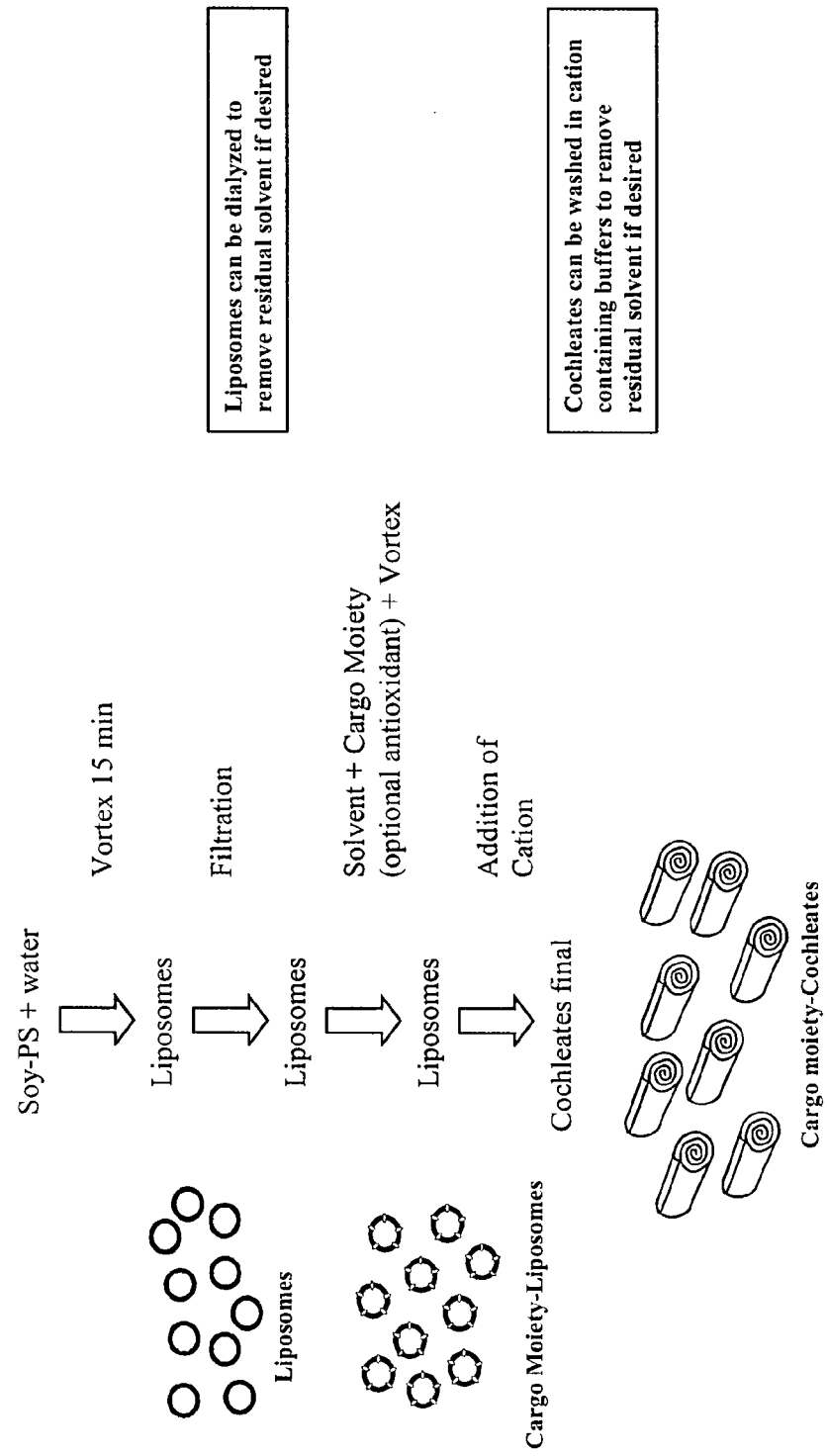
FIG. 2 illustrates an exemplary method of the present invention, wherein drug-liposomes are obtained by addition of a hydrophobic drug in solvent, optionally with an antioxidant, to a liposomal suspension.

FIG. 2 illustrates an exemplary method of the present invention, wherein drug-liposomes are obtained by addition of a hydrophobic drug in solvent (e.g., DMSO, DMF, THF, EtOH), optionally with an antioxidant (e.g., Vitamin E), to a liposomal suspension. A liposomal suspension is prepared by vortexing lipid (e.g., soyPS) and water and filtered, however, other methods of obtaining liposomal suspensions can be employed in the methods of the present invention. Cochleates are precipitated out by the addition of calcium (e.g., calcium chloride), and subsequently can be washed (e.g., with calcium containing buffers) to remove any residual solvent, if desired. Alternatively, residual solvent can be removed by other methods, e.g., dialysis.

Figure 3:
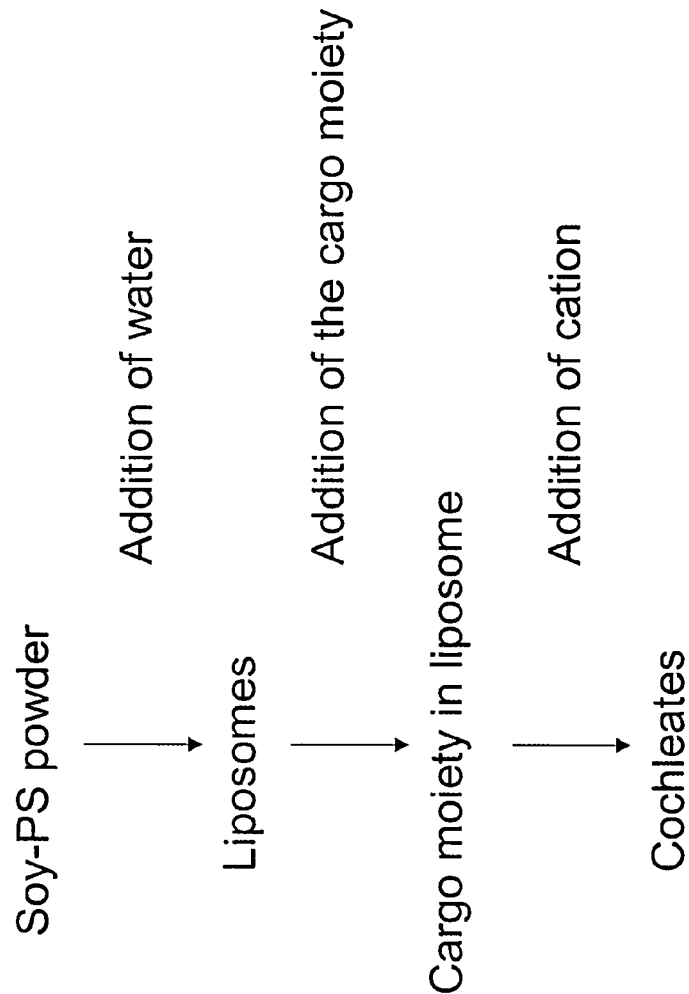
FIG. 3 illustrates another aspect of the invention, wherein hydrosoluble drugs are encochleated.

FIG. 3 illustrates another aspect of the invention, wherein hydrosoluble drugs are encochleated. In this method, a hydrosoluble drug is added directly to liposomes and subsequently precipitated. The liposomes are prepared by adding lipid (e.g., dry Soy PS powder) to water, but could be prepared or provided by any other known means.

Aggregation Inhibitors

In some preferred embodiments, the cochleates of the present invention can optionally include one or more aggregation inhibitors. The term "aggregation inhibitor," as used herein, refers to an agent that inhibits aggregation of cochleates. The aggregation inhibitor typically is present at least on the surface of the cochleate, and may only be present on the surface of the cochleate (e.g., when the aggregation inhibitor is introduced after cochleate formation). Aggregation inhibitors can be added before, after, or during cochleate formation. The type and/or amount of aggregation inhibitor can be adjusted to obtain a desired cochleate size and/or distribution. Additionally or alternatively, aggregation inhibitor(s) can be used to stabilize cochleate size and/or size distribution such that aggregation of cochleates is minimized or eliminated.

Such compositions are advantageous for several reasons including that smaller cochleates can allow for greater uptake by cells and rapid efficacy. Such a composition is suitable, e.g., when it is desired to rapidly and effectively deliver a cargo moiety (e.g., an antifungal or antibacterial agent against a fungal or bacterial infection). Moreover, particle size can have a targeting affect in that some cells may take up particles of a certain size more or less effectively. Size may also affect the manner in which cochleates interact with a cell (e.g., fusion events or uptake).

Aggregation inhibitors work in part by modifying the surface characteristics of the cochleates such that aggregation is inhibited. Aggregation can be inhibited, for example, by steric bulk around the cochleate, which inhibits aggregation and/or changes the nature of the cochleate structure, e.g., a change in the surface hydrophobicity and/or surface charge.

The terms "coat," "coated," "coating," and the like, unless otherwise indicated, refer to an agent (e.g. an aggregation inhibitor) present at least on the outer surfaces of a cochleate. Such agents may be associated with the bilayer by incorporation of at least part of the agent into the bilayer, and/or may be otherwise associated, e.g., by ionic attraction to the cation or hydrophobic or ionic attraction to the lipid.

Figure 37A:
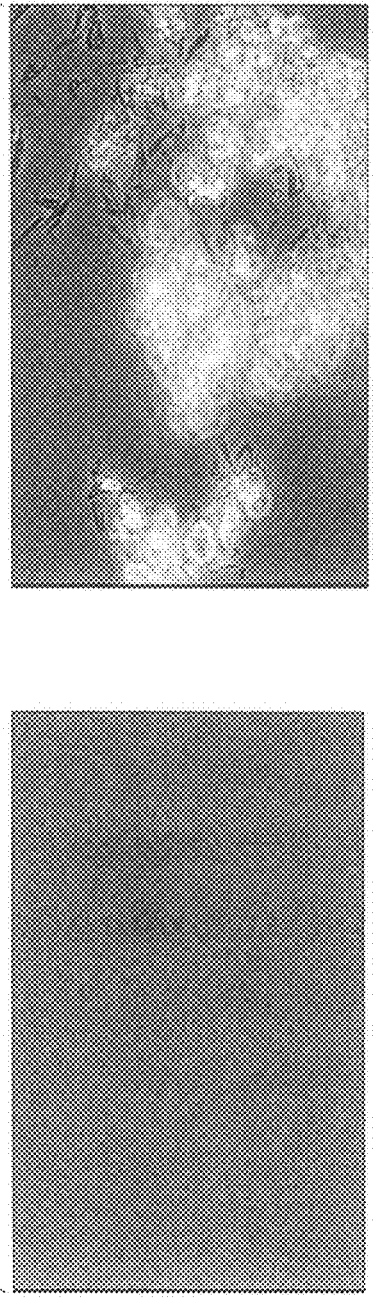
FIG. 37A is two images comparing acetaminophen cochleates with and without aggregation inhibitor (casein).

As discussed herein, cochleates can be formed by the calcium induced restructuring and fusion of lipid, e.g., phospholipid such as phosphatidylserine (PS). Due to the hydrophobic nature of the surfaces of cochleates in aqueous, calcium containing solutions, cochleates formed without the aggregation inhibitors of the invention can aggregate and form larger masses, e.g., needle-like structures in aspirin cochleates (FIG. 37A, right panel). It has been discovered that restricting and/or inhibiting the interaction of liposomes that can coalesce into cochleates at the time of cation addition limits the size of the resultant cochleate crystal, and prevents aggregation into larger particles. The addition of an aggregation inhibitor (e.g., casein) to liposomes prior to the addition of calcium results in stable non-aggregated nanocochleate structures (FIG. 37A, left panel).

The type and/or amount of aggregation inhibitor used can also determine the size of resulting cochleate. The presence of an aggregation inhibitor in differing concentrations also allows regulation of cochleate size distribution.

Figure 35:
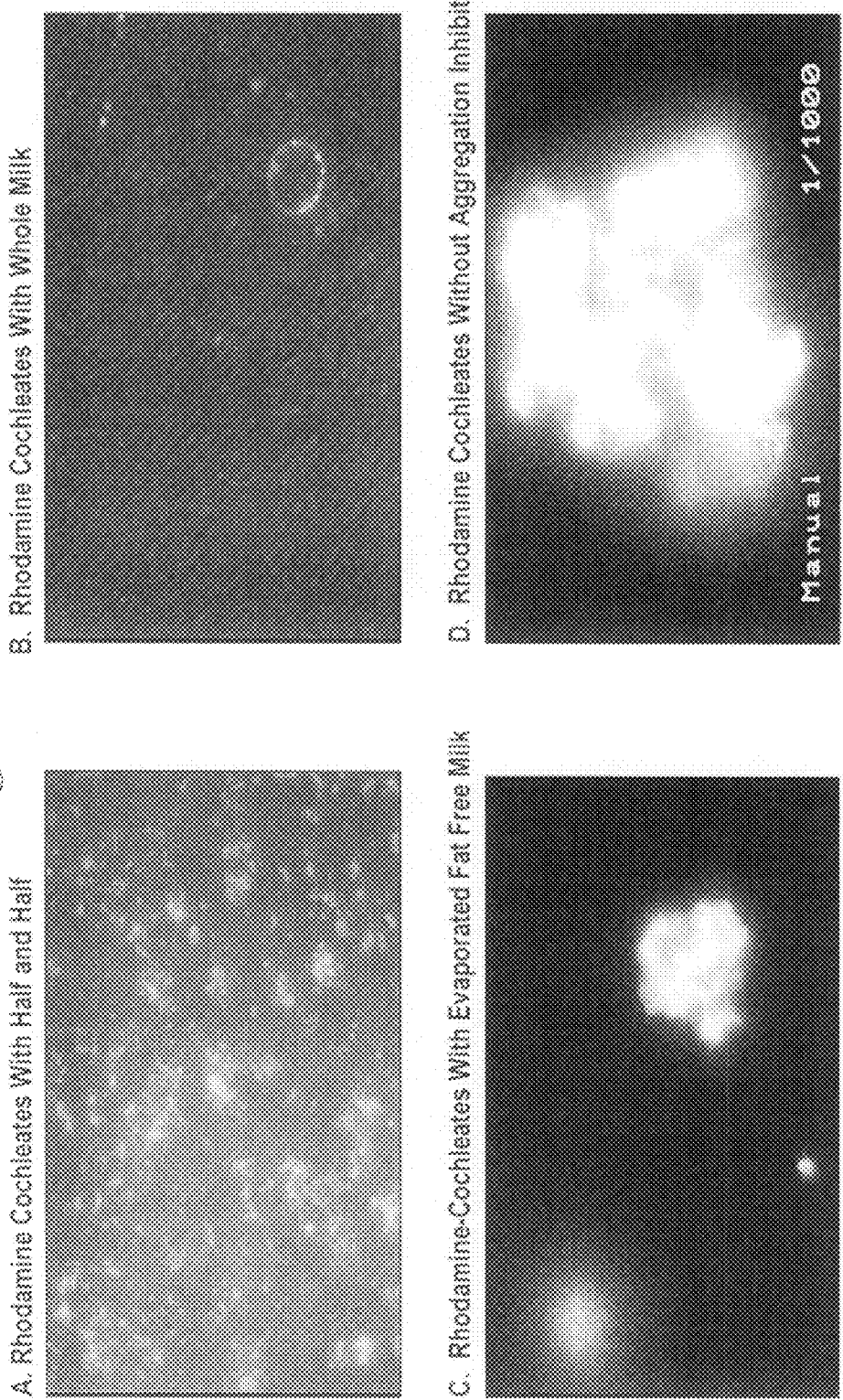
FIGS. 35A-D are four fluorescent images of Rhodamine-labeled cochleates demonstrating the effect of formulating cochleates in the presence of various aggregation inhibitors: half and half (FIG. 35A), whole milk (FIG. 35B), and fat-free milk (FIG. 35C).

It also has been discovered that addition of one or more aggregation inhibitors after formation of cochleates also inhibits and even reverses aggregation. For example, it is shown in FIG. 35 that the addition of half and half, whole milk, and fat free milk to Rhodamine-PE cochleates inhibits aggregation. It can also be noted that the milk products with more fat content (milk and half and half) inhibited aggregation more than the fat free milk, which has less fat content. Additionally, the addition of an aggregation inhibitor (milk) to aggregated cochleates has been demonstrated to disaggregate the cochleates as depicted in FIG. 36.

Suitable aggregation inhibitors that can be employed in accordance with the present invention, include but are not limited to at least one of the following: casein, κ-casein, milk, albumin, serum albumin, bovine serum albumin, rabbit serum albumin, methylcellulose, ethylcellulose, propylcellulose, hydroxycellulose, hydroxymethyl cellulose, hydroxyethyl cellulose, hydroxypropyl cellulose, hydroxypropylmethyl cellulose, polyvinyl pyrrolidone, carboxymethyl cellulose, carboxyethyl cellulose, pullulan, polyvinyl alcohol, sodium alginate, polyethylene glycol, polyethylene oxide, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, carrageenan, carnauba wax, shellac, latex polymers, milk protein isolate, soy protein isolate, whey protein isolate and mixtures thereof.

A preferred aggregation inhibitor is casein. Casein is a highly phosphorylated, calcium binding protein. Without wishing to be bound to any particular theory, it is believed that calcium mediates an interaction between negatively charged lipid (e.g., PS) and casein, thereby changing the surface properties of cochleates such that aggregation is inhibited. Another preferred aggregation inhibitor is milk and other milk products such as Half and Half, cream etc. Preferred milk products also contain casein. Another preferred aggregation inhibitor is an excipient, e.g., methylcellulose. Other preferred aggregation inhibitors include albumin, serum albumin, bovine serum albumin and rabbit serum albumin.

More than one aggregation inhibitor may be employed in the compositions of the invention. For example, both milk and methylcellulose may be used as an aggregation inhibitor.

In one embodiment, the cochleate compositions of the invention include between about 10% and about 0.1% aggregation inhibitor. Preferably, the aggregation inhibitor comprises about 1% of the cochleate composition.

In another embodiment, the cochleate compositions of the invention include an aggregation inhibitor to lipid ratio of between about 0.1:1 to about 4:1 by weight.

Preferably, the aggregation inhibitor to lipid ratio is about 1:1. A person of ordinary skill in the art will readily be able to determine the amount of aggregation inhibitor needed to form cochleates of the desired size with no more than routine experimentation.

Cochleate Size and Distribution

The formation of cochleates can be envisioned as a crystallization event that spontaneously occurs upon the interaction of charged lipids and oppositely charged multivalent cations. Modulating of the size of cochleate crystals formed, however, has prior to the present invention proved difficult.

In aqueous suspension, plain cochleates generally aggregate and upon long term storage form larger masses which can be several microns in size. Because of the association of the calcium with the lipid head group, the surfaces of cochleates have a hydrophobic character. When suspended in aqueous buffer, cochleate aggregation is a consequence of hydrophobic interactions, minimizing the amount of surface area exposed to water. FIG. 30 is a schematic model of cochleate aggregation in aqueous solution.

It has been discovered that aggregation can be inhibited and even reversed, and individual cochleate particles can be stabilized by changing the surface properties of the cochleates and thereby inhibiting cochleate-cochleate interaction. Aggregation can be inhibited by including in the liposome suspension a material that prevents liposome-liposome interaction at the time of calcium addition and thereafter. Alternatively, the aggregation inhibitor can be added after formation of cochleates. Additionally, the amount of aggregation inhibitor can be varied, thus allowing modulation of the size of the cochleates.

FIG. 31 is a schematic model of cochleates coated in proteins to reduce the amount of cochleate aggregation to near zero. As demonstrated in greater detail below, the resulting cochleates are surprisingly small. Particle size analysis demonstrates that these formulations are stable nanocochleates. Additional experiments, presented below in the Examples, have extended these observations providing the conceptual basis for the development of protocols for the preparation of stabilized nanocochleate formulations of defined size.

FIG. 32 is a schematic diagram of an exemplary method of making cochleates of the invention by adding an aggregation inhibitor subsequent to cochleate formation. Accordingly, in one aspect, the invention provides a cochleate composition comprising a plurality of cochleates and an aggregation inhibitor. In a preferred embodiment, the aggregation inhibitor comprises a coating on the cochleates. Such a "coating" can be formed by addition of the aggregation inhibitor after formation of cochleates. The amount of aggregation inhibitor employed and the point at which the aggregation inhibitor is added can be used to control the particle sizes of the cochleates.

Accordingly, the present invention provides a cochleate composition comprising a plurality of cochleates and an aggregation inhibitor having a desired particle size distribution, and methods of making the same. As demonstrated herein, the amount of aggregation inhibitor and/or time of addition can be varied to modulate and/or stabilize the size and/or size distribution of a cochleate composition.

In one embodiment, the aggregation inhibitor can be employed to achieve cochleates that are significantly smaller and have narrower particle size distributions than compositions without aggregation inhibitors as demonstrated, e.g., in FIG. 34. Such compositions are advantageous for several reasons including that they can allow for greater uptake by cells (see e.g., FIG. 33), and rapid efficacy (see e.g., FIGS. 46, 47, 49 and 50). Such a composition is suitable, e.g., when it is desired to rapidly and effectively deliver a cargo moiety (e.g., an antifungal or antibacterial agent against a fungal or bacterial infection). Moreover, cochleate size can have a targeting affect in that some cells may take up particles of a certain size more or less effectively. Size may also affect the manner in which cochleates interact with a cell (e.g., fusion events or uptake).

In another embodiment, the aggregation inhibitor can be employed in an amount to achieve cochleate-compositions having a particle size relatively larger than that which can be achieved without or with other aggregation inhibitors (e.g., if more and/or a different aggregation inhibitor used). Such a composition can be useful, e.g., when delayed uptake and/or release of the cargo molecule is desired, or when targeted cells or organs more effectively take up cochleates in the relatively larger size range. Such compositions also may have sustained activity (relative to smaller cochleate compositions) because it can take longer for the cargo moiety to be released from a larger cochleate, e.g., if multiple fusion events are required.

In yet another embodiment, the amount and/or types of aggregation inhibitor can be chosen to manufacture a cochleate composition that has a wide particle size distribution such that the cargo moiety is released over a period of time because smaller cochleates are rapidly taken up initially followed by take up or fusion events with increasingly larger cochleates. In addition, size may not only affect what type of cells take up the cochleate, but also how the cochleates interact with certain cells, e.g., size may effect whether a cochleate is taken up by a cell or undergoes one or more fusion events with a cell.

Moreover, in yet further embodiments, several compositions can be combined for desired release profiles, e.g., a pulsed released, or combined release. For example, a rapid release nanocochleate composition can be mixed with a delayed-release larger size or even standard cochleate composition, such that an immediate and a delayed release are both realized. In an exemplary case, both small and large antibiotic cochleates are administered in order to treat a subject with a high initial dose (small cochleates) and to maintain enough antibiotic in the serum to be effective against remaining bacteria (large cochleates). In addition, the cochleate compositions may have different cargo moieties, e.g., a stomach protecting medication can be formulated with nanocochleates for initial release (or a large distribution for long term release), and one or more non-steroidal anti-inflammatory drugs can be formulated with larger cochleates (NSAID) for release after the stomach protecting medication is released.

Figure 54:
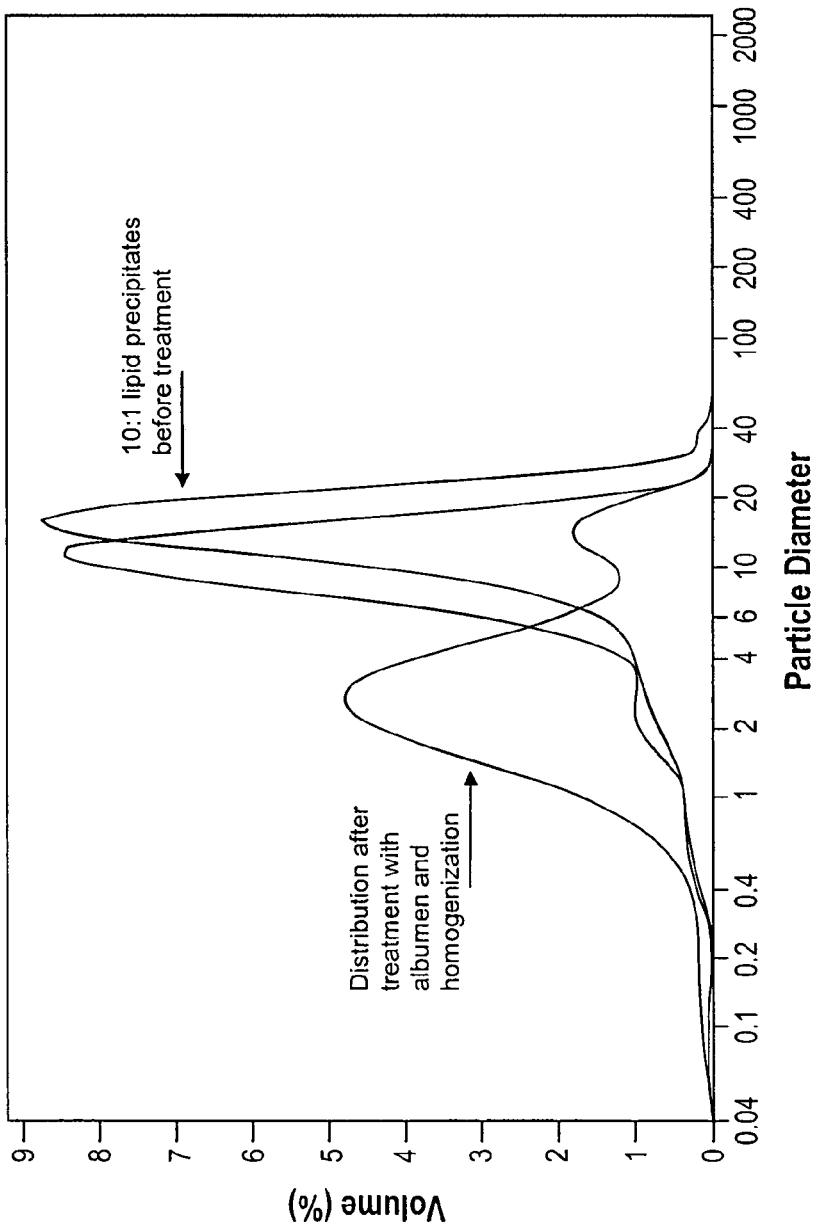
FIG. 54 is a graph demonstrating the size distribution of 10:1 soy PS:caspofungin cochleates before and after addition of bovine serum albumin and homogenization.

An aggregation inhibitor also can be employed to stabilize particle size and particle size distribution. For example, it can be used to "lock-in" the cochleate size and distribution of standard cochleates and/or cochleates having an aggregation inhibitor. While the cochleates of the invention typically are stable over long periods of time, standard cochleates (cochleates formed without aggregation inhibitors) can tend to aggregate over time. Thus, standard cochleates can be reduced in size and/or stabilized by addition to such aggregation inhibitors, e.g., addition of methylcellulose after cochleate formation. FIG. 54 shows the decrease in size of caspofungin cochleates which have been homogenized and treated with bovine serum albumin.

Cochleates formed in the presence of aggregation inhibitors do not aggregate. Accordingly, such compositions are advantageous for several reasons including, e.g., greater uptake by cells, and increased efficacy. Cochleate compositions of the invention preferably have a mean diameter less than about 5, 4, 3, 2, or 1 micrometer. Preferably, the cochleate compositions have a mean diameter less than about 900 nm, 800 nm, 700 nm, 600 nm, 500 nm, 400 nm, 300 nm, 200 nm, or 100 nm. All individual values between these values (880, 435, 350), are meant to be included and are within the scope of this invention. In another embodiment, cochleate compositions of the invention include cochleate populations having a mean diameter about equal to or greater than about 1 micrometer, e.g., 2, 3, 4, 5, 10, 50, or 100 micrometers. All individual values and ranges within these ranges are meant to be included and are within the scope of this invention.

Preferably, the size distribution is narrow relative to that observed in standard cochleates (cochleates formed without aggregation inhibitors). As demonstrated, e.g. in FIG. 34, the size distribution of cochleate compositions with aggregation inhibitors is significantly improved relative to that observed in standard cochleate compositions. Preferably, the cochleates have a size distribution of less than about 30, 20, 10, 5, 3 or 1 µm, 900 nm, 800 nm, 700 nm, 600 nm, 500 nm, 400 nm, 300 nm, 200 nm, or 100 nm. All individual values between these values (550 nm, 420 nm, 475 nm, etc.), are meant to be included and are within the scope of this invention. Such compositions are particularly desirable where uptake by macrophages is desired. It can readily be appreciated that particle size can be adjusted to a size suitable for uptake by desired organs or cells and/or unsuitable for uptake by organs or cells. In another embodiment, a wider size distribution of cochleates is employed, e.g., about 10, 20, 50, 100, 200 . . . 500 micrometers. All individual values within these ranges are meant to be included and are within the scope of this invention. Such compositions can be useful for long term release of cargo moieties.

Additionally, as discussed above, the invention contemplates combination of cochleate populations with one or more cargo moieties, one or more size distributions, and one or more mean diameter, to achieve a desired release pattern, e.g., pulsed release, delayed release and/or timed release of different cargo-moieties.

Cargo Moieties

The cochleates of the present invention are preferably associated or "loaded" with a cargo moiety. A "cargo moiety" is a moiety to be encochleated, and generally does not refer to the lipid and ion employed to precipitate the cochleate. Cargo moieties include any compounds having a property of biological interest, e.g., ones that have a role in the life processes of a living organism. A cargo moiety may be organic or inorganic, a monomer or a polymer, endogenous to a host organism or not, naturally occurring or synthesized in vitro and the like.

Thus, examples include vitamins, minerals, nutrients, micronutrients, amino acids, toxins, microbicides, microbistats, co-factors, enzymes, polypeptides, polypeptide aggregates, polynucleotides, lipids, carbohydrates, nucleotides, starches, pigments, fatty acids, saturated fatty acids, monounsaturated fatty acids, polyunsaturated fatty acids, flavorings, essential oils, extracts, hormones, cytokines, viruses, organelles, steroids and other multi-ring structures, saccharides, metals, metabolic poisons, antigens, imaging agents, porphyrins, tetrapyrrolic pigments, drugs and the like.

The cargo moiety can be a diagnostic agent, such as an imaging agent. Imaging agents include nuclear agents and fluorescent probes, e.g., porphyrins. Porphyrins include tetrapyrrolic agents or pigments. One such tetrapyrrolic agent is Zinc Tetra-Phenyl Porphyrin (ZnTPP), which is a hydrophobic, fluorescent molecule that has high absorption in the visible spectrum (dark purple).

The polynucleotide can be one that is expressed to yield a biologically active polypeptide or polynucleotide. Thus, the polypeptide may serve as an immunogen or, for example, have enzymatic activity. The polynucleotide may have catalytic activity, for example, be a ribosome, or may serve as an inhibitor of transcription or translation, e.g., a small interfering RNA (siRNA) or an antisense molecule. The polynucleotide can be an antisense molecule including modified antisense molecule, such as a morpholino antisense molecule. The polynucleotide can be modified, e.g., it can be synthesized to have a morpholino backbone. If expressed, the polynucleotide preferably includes the necessary regulatory elements, such as a promoter, as known in the art. A specific example of a polypeptide is insulin.

The cargo moiety can be an organic molecule that is hydrophobic in aqueous media. The cargo moiety can also be a water-soluble monovalent or polyvalent cationic molecule, anionic, or net neutral at physiological pH.

The drug can be, but is not limited to, a protein, a small peptide, a bioactive polynucleotide, an antibiotic, an antiviral, an anesthetic, antipsychotic, an anti-infectious, an antifungal, an anticancer, an immunosuppressant, an immunostimulant, a steroidal anti-inflammatory, a non-steroidal anti-inflammatory, an antioxidant, an antidepressant which can be synthetically or naturally derived, a substance which supports or enhances mental function or inhibits mental deterioration, an anticonvulsant, an HIV protease inhibitor, a non-nucleophilic reverse transcriptase inhibitor, a cytokine, a tranquilizer, a mucolytic agent, a dilator, a vasoconstrictor, a decongestant, a leukotriene inhibitor, an anti-cholinergic, an anti-histamine, a cholesterol lipid metabolism modulating agent or a vasodilatory agent. The drug can also be any over the counter (non-prescription) medication.

An antifungal drug can be a polyene macrolide, tetraene macrolide, pentaenic macrolide, fluorinated pyrimidine, imidazole, azole, triazole, halogenated phenolic ether, thiocarbamate, allylamine, sterol inhibitor, and an agent that interpolates fungal cell wall components.

Nonsteroidal anti-inflammatory drugs (NSAIDS) are typically used to treat inflammation, muscle strains, and high fever. NSAIDS function by inhibiting. cyclooxygenase-1 (COX1) and cyclooxygenase-2 (COX2). COX1 enzymes are responsible for protecting the lining of the stomach and COX2 enzymes are responsible for the production of prostaglandins, which are important in the inflammatory process. Unfortunately, commercially available preparations of NSAIDS are active against both COX1 and COX2, and therefore have unwanted side effects such as ulcers, upset stomach or nausea.

Examples of suitable drugs include Amphotericin B, acyclovir, adriamycin, carbamazepine, ivermectin, melphalen, nifedipine, indomethacin, curcumin, aspirin, ibuprofen, naproxen, acetaminophen, rofecoxib, diclofenac, ketoprofen, meloxicam, nabumetone, estrogens, testosterones, steroids, phenyloin, ergotamines, cannabinoids, rapamycin, propanadid, propofol, alphadione, echinomycin, miconazole, miconazole nitrate, ketoconazole, itraconazole, fluconazole, griseofulvin, clotrimazole, econazole, terconazole, butoconazole, oxiconazole, sulconazole, saperconazole, voriconazole, ciclopirox olamine, haloprogin, tolnaftate, naftifine, terbinafine hydrochloride, morpholines, flucytosine, natamycin, butenafine, undecylenic acid, Whitefield's ointment, propionic acid, and caprylic acid, clioquinol, selenium sulfide, teniposide, hexamethylmelamine, taxol, taxotere, 18-hydroxydeoxycorticosterone, prednisolone, dexamethasone, cortisone, hydrocortisone, piroxicam, diazepam, verapamil, vancomycin, tobramycin, teicoplanin, bleomycin, peptidolglycan, ristocetin, sialoglycoproteins, orienticin, avaporcin, helevecardin, galacardin, actinoidin, gentamycin, netilmicin, amikacin, kanamycin A, kanamycin B, neomycin, paromomycin, neamine, streptomycin, dihydrostreptomycin, apramycin, ribostamycin, spectinomycin, caspofungin, echinocandin B, aculeacin A, micafungin, anidulafungin, cilofungin, pneumocandin, geldanamycin, nystatin, rifampin, tyrphostin, a glucan synthesis inhibitor, vitamin A acid, mesalamine, risedronate, nitrofurantoin, dantrolene, etidronate, nicotine, amitriptyline, clomipramine, citalopram, dothiepin, doxepin, fluoxetine, imipramine, lofepramine, mirtazapine, nortriptyline, paroxetine, reboxetine, sertraline, trazodone, venlafaxine, dopamine, St. John's wort, phosphatidylserine, phosphatidic acid, amastatin, antipain, bestatin, benzamidine, chymostatin, 3,4-dichloroisocoumarin, elastatinal, leupeptin, pepstatin, 1,10-phenanthroline, phosphoramidon, ethosuximide, ethotoin, felbamate, fosphenytoin, lamotrigine, levitiracetam, mephenyloin, methsuximide, oxcatbazepine, phenobarbital, phensuximide, primidone, topirimate, trimethadione, zonisamide, saquinavir, ritonavir, indinavir, nelfinavir, and amprenavir.

Tyrphostin and geldanamycin (GA) target the oncoprotein/oncogene erb B2, which is overexpressed on a variety of tumor cells, and this high level of expression is functionally related to transformation.

GA is a hydrophobic small molecule drug that has been shown to have activity in vitro against cancer cell lines. It inhibits ErbB2 expression by destabilizing chaperone proteins. GA has been traditionally dissolved in DMSO for in vitro and in vivo testing. In vivo, it has anti-tumor activity, but has significant hepatotoxicity. Tyrphostin AG-825 is a tyrosine kinase inhibitor that has activity against cancer cell lines over-expressing erb B2. It inhibits its activity, and therefore cellular proliferation, but not erb B2 expression.

The drug can be a polypeptide such as cyclosporin, Angiotensin I, II and III, enkephalins and their analogs, ACTH, anti-inflammatory peptides I, II, III, bradykinin, calcitonin, b-endorphin, dinorphin, leucokinin, leutinizing hormone releasing hormone (LHRH), insulin, neurokinins, somatostatin, substance P, thyroid releasing hormone (TRH) and vasopressin.

The drug can be an antigen, but is not limited to a protein antigen. The antigen can also be a carbohydrate or DNA. Examples of antigenic proteins include membrane proteins, carbohydrates, envelope glycoproteins from viruses, animal cell proteins, plant cell proteins, bacterial proteins, and parasitic proteins.

The antigen can be extracted from the source particle, cell, tissue, or organism by known methods. Biological activity of the antigen need not be maintained. However, in some instances (e.g., where a protein has membrane fusion or ligand binding activity or a complex conformation which is recognized by the immune system), it is desirable to maintain the biological activity. In these instances, an extraction buffer containing a detergent which does not destroy the biological activity of the membrane protein is employed. Suitable detergents include ionic detergents such as cholate salts, deoxycholate salts and the like or heterogeneous polyoxyethylene detergents such as Tween, BRIG or Triton.

Utilization of this method allows reconstitution of antigens into the liposomes with retention of biological activities, and efficient association with the cochleates. The method may also be employed without sonication, extreme pH, temperature, or pressure all of which may have an adverse effect upon efficient reconstitution of the antigen in a biologically active form.

Suitable nutrients include, but are not limited to lycopene, micronutrients such as phytochemicals or zoochemicals, vitamins, minerals, fatty acids, amino acids, fish oils, fish oil extracts, saccharides, herbal products and essential oils and flavor agents. Specific examples include Vitamins A, B, B1, B2, B3, B12, B6, B-complex, C, D, E, and K, vitamin precursors, caroteniods, and beta-carotene, resveratrol, biotin, choline, inositol, gingko, lutein, zeaxanthine, quercetin, silibinin, perillyl alcohol, genistein, sulfurophane, and essential fatty acids, including eicosapentaenoic acid (EPA), gamma-3, omega-3, gamma-6 and omega-6 fatty acids, herbs, spices, and iron. Minerals include, but are not limited to boron, chromium, colloidal minerals, colloidal silver, copper, manganese, potassium, selenium, vanadium, vanadyl sulfate, calcium, magnesium, barium, iron and zinc.

As used herein, "micronutrient" is a nutrient that the body must obtain from outside sources. Generally micronutrients are essential to the body in small amounts.

The cargo moiety can be a saccharide or sweetener, e.g., saccharine, isomalt, maltodextrin, aspartame, glucose, maltose, dextrose, fructose and sucrose. Flavor agents include oils, essential oils, or extracts, including but not limited to oils and extracts of cinnamon, vanilla, almond, peppermint, spearmint, chamomile, geranium, ginger, grapefruit, hyssop, jasmine, lavender, lemon, lemongrass, marjoram, lime, nutmeg, orange, rosemary, sage, rose, thyme, anise, basil, black pepper, tea or tea extracts, an herb, a citrus, a spice or a seed.

In some preferred embodiments, the cargo moiety can be a protonized cargo moiety. In one embodiment, the cargo moiety is a protonized weakly basic cargo moiety. The pharmacokinetics of weakly basic cargo moieties (e.g., vancomycin and tobramycin), conventionally has been dominated by their poor solubility in lipids such as milk. Because of this poor solubility and the lack of water in the cochleates, it was surprising that weakly basic cargo moieties could be incorporated into cochleates at the concentrations achieved in the present invention. It has been discovered, however, that protonized weakly basic cargo moieties can be incorporated into anhydrous cochleates. Protonized neutral cargo moieties can similarly be precipitated with negatively charged lipid, provided that acidification renders them cationic. Additionally, cargo moieties suitable for use in accordance with the present invention can include protonized weakly acidic cargo moieties or protonized amphoteric cargo moieties. Weakly acidic cargo moieties or amphoteric cargo moieties may or may not include an initial positive charge. Such cargo moieties would also be rendered cationic by protonization. Protonizable cargo moieties can be negatively charged, positively charged, uncharged or zwitterionic. The invention is particularly advantageous in the preparation of protonized water-soluble cargo moieties.

In one embodiment, the protonized cargo moiety is monovalent. In other embodiments, the protonized cargo moiety is multivalent, e.g., divalent, trivalent, etc. In certain embodiments, a higher valency may be preferable due to the size and/or conformation of the cargo moiety.

Moreover, because the protonized cargo moieties are cationic, hydrous cochleates can be a made without additional cation (e.g., a metal cation, such as calcium). For example, vancomycin-cochleates have been made without cation, as described below. Anhydrous cochleates made with divalent metal cation, e.g., $Ca^{2+}$, are preferred and are active against *Staph. A.* infection in vitro.

In one embodiment, the protonized cargo moiety is a multivalent cation (i.e., polycationic). The protonization or acidification can render a non-cationic moiety cationic or increase the valency of a cationic moiety. The protonized cargo moiety can optionally be isolated and characterized prior to formulation into a cochleate. Alternatively, the cargo moiety can be obtained or purchased protonized (e.g., vancomycin hydrochloride or caspofungin acetate).

In one embodiment, the protonized cargo moiety is a protonized peptide, such as a protonized protein.

In another embodiment, the protonized cargo moiety is a protonized nucleotide. The protonized nucleotide can be, but is not limited to a protonized DNA, a protonized RNA, a protonized morpholino, a protonized siRNA molecule, a protonized ribozyme, a protonized antisense molecule, or a protonized plasmid.

In a preferred embodiment, the cargo moiety is a drug, including, but not limited to, an aminoglyconjugate, e.g., an aminoglycoside or an aminoglycopeptide. Preferably the aminoglycoconjugate is weakly basic.

In a particularly preferred embodiment, the aminoglycoconjugate is one or more of the following: vancomycin, teicoplanin, bleomycin, peptidolglycan, ristocetin, sialoglycoproteins, orienticin, avaporcin, helevecardin, galacardin, actinoidin, gentamycin, netilmicin tobramycin, amikacin, kanamycin A, kanamycin B, neomycin, paromomycin, neamine, streptomycin, dihydrostreptomycin, apramycin, ribostamycin, and spectinomycin.

In another preferred embodiment, the cargo moiety is an echinocandin. In a particularly preferred embodiment, the echinocandin is one or more of the following: caspofungin, echinocandin B, aculeacin A, micafungin, anidulafungin, cilofungin, and pneumocandin.

The cochleates of the invention can be prepared with a wide range of cargo moiety to lipid ratios. By way of example, the ratio of cargo moiety to lipid can be between about 20,000:1 and about 0.5:1 by weight. In one embodiment the ratio is about 1:1 by weight. In others the ratio is about 2:1, 3:1, 4:1, 5:1, 10:1, 20:1, 50:1, 100:1, 200:1, or 400:1 by weight. All individual ranges and values between 20,000:1 and 0.5:1 are encompassed by the invention.

The cochleates of the present invention can optionally include one or more additional cargo moieties. The additional cargo moiety can be a second protonized cargo moiety or any other cargo moiety.

Additional pharmacologically active agents may be delivered in combination with the primary active agents, e.g., the cochleates of this invention. In one embodiment, such agents include, but are not limited to agents that reduce the risk of atherosclerotic events and/or complications thereof. Such agents include, but are not limited to beta-blockers, beta blockers and thiazide diuretic combinations, HMG CoA reductase inhibitors, statins, aspirin, ace inhibitors, ace receptor inhibitors (ARBs), and the like.

Suitable beta blockers include, but are not limited to cardioselective (selective beta 1 blockers), e.g., acebutolol (e.g., Sectral™), atenolol (e.g., Tenormin™), betaxolol (e.g., Kerlone™), bisoprolol (e.g., Zebeta™), metoprolol (e.g., Lopressor™), and the like. Suitable non-selective blockers (block beta 1 and beta 2 equally) include, but are not limited to carteolol (e.g., Cartrol™), nadolol (e.g., Corgard™), penbutolol (e.g., Levatol™), pindolol (e.g., Visken™), propranolol (e.g., Inderal™), timolol (e.g., Blockadren™), labetalol (e.g., Normodyne™, Trandate™), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

Suitable statins include, but are not limited to pravastatin (e.g., Pravachol™), simvastatin (e.g., Zocor™), lovastatin (e.g., Mevacor™), and the like.

Suitable ace inhibitors include, but are not limited to captopril (e.g., Capoten™), benazepril (e.g., Lotensin™), enalapril (e.g., Vasotec™), fosinopril (e.g., Monopril™), lisinopril (e.g., Prinivil™ or Zestril™), quinapril (e.g., Accupril™), ramipril (e.g., Altace™), imidapril, perindopril erbumine (e.g., Aceon™), trandolapril (e.g., Mavik™), and the like.

Suitable ARBS (Ace Receptor Blockers) include but are not limited to losartan (e.g., Cozaar™), irbesartan (e.g., Avapro™), candesartan (e.g., Atacand™), valsartan (e.g., Diovan™), and the like.

Suitable HMG CoA reductase inhibitors that are useful in accordance with the methods and compositions of the invention are statin molecules. These include: Lovastatin (e.g., Mevacor™), Pravastatin (e.g., Pravachol™), Simvastatin (e.g., Zocor™), Fluvastatin (e.g., Lescol™), Atorvastatin (e.g., Lipitor™), or Cerivastatin (e.g., Baycol™).

Other agents that may be administered in conjunction with the cochleates of the invention for treatment of atherosclerotic events and/or complications thereof are phytosterols, phytostanols and their derivatives and isomers; soy protein; soluble fibers, e.g. beta-glucan from, for example, oat and psyllium, nuts, rice bran oil, each of which is particularly suitable for use in food, dietary supplements and food additive compositions. Phytosterols may be solid (e.g., powder, granules) or liquid (e.g., oil) form.

It will be obvious to a person of skill in the art that the choice of the agent for treatment of atherosclerotic events and/or complications thereof depends on the intended delivery vehicle (e.g., food, supplement, pharmaceutical) and the mode of administration.

The cargo moiety can additionally be bound to a cochleate component or to a hydrophobic tail. In one embodiment, the cargo moiety is bound to the lipid cochleate component or the hydrophobic tail with a digestible, reducible, or otherwise reversible linker. The cargo moiety can be bound in a reversible manner e.g., with a reducible or digestible linker) or a linker susceptible to target conditions (e.g., pH, temperature, ultrasonic energy and the like). This is particularly useful as the linker can be chosen such that it is readily digestible, e.g., by an enzyme, in the body generally or even in a target structure. Thus, e.g., a linker can be chosen such that it is degraded by an enzyme in the plasma, interstitial fluids, in a cell (e.g. a macrophage) or in an endosome, such that the protonized cargo moiety becomes detached and available in unbound form in these structures. In another embodiment, the reversible linker can be an electrostatic or other bond that is broken by a change in pH, e.g., in an organ or other structure in which the cochleate experiences a pH gradient. In another embodiment, the linker is reversed by a change in temperature, e.g., by exposure to body temperature.

In one embodiment, the cargo moiety is bound by an electrostatic, hydrophobic, covalent, or ionic interaction with a lipid component such as a hydrophobic tail. In a preferred embodiment, the cargo moiety is bound to a component of the bilayer of the cochleate, e.g., a phospholipid or other lipid. Covalently binding the cargo moiety to the lipid by cross-linking can be accomplished by known methods. In one embodiment, the covalent bond is reversible so that the cargo moiety can be detached from the lipid component or hydrophobic tail under suitable conditions. For example, a cargo moiety can be attached to a phospholipid via a linker that can be cleaved by an enzyme endogenous to a target tissue, organ, or structure (e.g., a plasma protein, interstitial protein, an endosome or the intracellular milieu), such that the cargo moiety is delivered to the target tissue, organ or other structure. In alternative embodiments the cargo moiety can be attached by any other means, for example, by electrostatic interactions and/or hydrophobic interactions.

The cargo moiety can be associated with the lipid component or hydrophobic tail in any of the methods described herein. For example, in one embodiment, the cargo moiety is associated with the lipid component, such that the cargo moiety dissociates with the lipid component upon contact with a target environment. The cargo moiety can be bound to a component of the cochleate with any of the linkers described herein, e.g., a linker that is reducible, or otherwise reversible or digestible by an enzyme, protein, or molecule endogenous to the target environment. The enzyme can be an extracellular, intracellular or endosomal enzyme endogenous to the subject. In another embodiment, the cargo moiety component is electrostatically associated with the lipid component and dissociates with the cochleate upon contact with a pH gradient in a cell or organ of the subject.

Delivery of Cargo Moieties

Many naturally occurring membrane fusion events involve the interaction of calcium with negatively charged phospholipids (e.g. PS and phosphatidylglycerol). Calcium-induced perturbations of membranes containing negatively charged lipids, and the subsequent membrane fusion events, are important mechanisms in many natural membrane fusion processes. Therefore, cochleates can be envisioned as membrane fusion intermediates.

Phase/fluorescent and fluorescent images of Rhodamine-labeled cochleates incubated with splenocytes were captured and are shown in FIG. 1. These images indicate that a fusion event occurs between the outer layer of the cochleate and the cell membrane, resulting in the delivery of encochleated material into the cytoplasm of the target cell. As the calcium rich, highly ordered membrane of a cochleate first comes into close approximation to a natural membrane, a perturbation and reordering of the cell membrane is induced, resulting in a fusion event between the outer layer of the cochleate and the cell membrane. This fusion results in the delivery of a small amount of the encochleated material into the cytoplasm of the target cell. The cochleate can then break free of the cell and be available for another fusion event, either with the same or another cell.

Additionally or alternatively, particularly with active phagocytic cells, cochleates may be taken up by endocytosis and fuse from within the endocytic vesicle. Cochleates made with trace amounts of fluorescent lipids have been shown to bind and gradually transfer lipids to the plasma membrane and interior membranes of white blood cells in vitro. FIG. 33, for example, demonstrates the uptake of cochleates by macrophages.

Cochleates are useful for the delivery of a cargo moiety to cultured cells, tissues or organisms by a variety of administration routes. The term "delivery," as used herein, refers to any means of bringing or transporting a cargo moiety to a host, a food item, a formulation, a pharmaceutical composition, or any other system, wherein the cargo moiety maintains at least a portion of its activity. For example, the use of cochleates to deliver protein or peptide molecules as vaccines has been disclosed in U.S. Pat. No. 5,840,707, issued Nov. 24, 1998. Similarly, polypeptide-cochleates are effective immunogens when administered to animals by intraperitoneal and intramuscular routes of immunization (G. Goodman-Snitkoff, et al., J. Immunol., Vol. 147, p. 410 (1991); M. D. Miller, et al., J. Exp. Med., Vol. 176, p. 1739 (1992)). Further, cochleates are effective delivery vehicles for encapsulated proteins and/or DNA to animals and to cells in culture. For example, reconstituted Sendai or influenza virus glycoproteins are efficiently delivered in encochleated form (Mannino and Gould-Fogerite, Biotechniques 6(1):682-90 (1988); Gould-Fogerite et al., Gene 84:429 (1989); Miller et al., J. Exp. Med. 176: 1739 (1992)).

The cochleates can be coadministered with a further agent. The second agent can be delivered in the same cochleate preparation, in a separate cochleate preparation mixed with the cochleate preparation of the invention, separately in another form (e.g., capsules or pills), or in a carrier with the cochleate preparation. The cochleates can further include one or more additional cargo moieties, such as other drugs, peptides, nucleotides (e.g., DNA and RNA), antigens, nutrients, flavors and/or proteins.

The cochleates of the invention also can include a reporter molecule for use in in vitro diagnostic assays, which can be a fluorophore, radiolabel or imaging agent. The cochleates can include molecules that direct binding of the cochleate to a specific cellular target, or promotes selective entry into a particular cell type.

One advantage of the cochleates of the present invention is the stability of the composition. Cochleates can be administered by any route, e.g., mucosal or systemic, without concern. Cochleates can be administered orally or by instillation without concern, as well as by the more traditional routes, such as oral, intranasal, intraoculate, intrarectal, intravaginal, intrapulmonary, topical, subcutaneous, intradermal, intramuscular, intravenous, transdermal, systemic, intrathecal (into CSF), and the like. Direct application to mucosal surfaces is an attractive delivery means made possible with cochleates. Delivery can be effected by, e.g., a nasal spray or nasal bath or irrigation.

Another advantage of the present invention is the ability to modulate cochleate size. Modulation of the size of cochleates and cochleate compositions changes the manner in which the cargo moiety is taken up by cells. For example, in general, small cochleates are taken up quickly and efficiently into cells, whereas larger cochleates are taken up more slowly, but tend to retain efficacy for a longer period of time. Also, in some cases small cochleates are more effective than large cochleates in certain cells, while in other cells large cochleates are more effective than small cochleates.

Cochleates and cochleate compositions can also be administered to humans and non-human animals, such as dog, cats, and farm animals, in food or beverage preparations. Such compositions can be introduced to the food or beverage compositions by the manufacturer (e.g., to supplement food with nutrients), or by the consumer (e.g., where the cochleate composition is sold separately as a food additive). For example, nutrients and/or flavorings may be incorporated into dog or cat food, particularly where such nutrient and/or flavoring is fragile and normally decomposes or loses activity when exposed to oxygen and/or water. Cochleates may be added at any stage into the preparation of dog or cat food, as the cochleates are stable under extreme pressure and temperature conditions.

Another advantage of cochleates and cochleate compositions of the present invention is their ability to reduce a number of unwanted side effects. A number of drugs currently on the market cause gastrointestinal distress and often high circulating blood levels lead to toxicity in a number of vital organs. The ingestion of, e.g., aspirin may result in epigastric distress, nausea, and vomiting. Aspirin may also cause gastric ulceration; exacerbation of peptic ulcer symptoms, gastrointestinal hemorrhage, and erosive gastritis have all been reported in patients on high-dose therapy but also may occur even when low doses are administered. In high doses, aspirin can also cause hepatic injury. Aspirin can cause retention of salt and water as well as an acute reduction of renal function in patients with congestive heart failure or renal disease. Although long-term use of aspirin alone rarely is associated with nephrotoxicity, the prolonged and excessive ingestion of aspirin in combination with other compounds can produce papillary necrosis and interstitial nephritis. Although acetaminophen is usually well tolerated, skin rash (generally erythematous or urticarial) and other allergic reactions occur occasionally. Occasionally, the rash can be more serious and may be accompanied by drug fever and mucosal lesions. In other examples, the use of acetaminophen has been associated with neutropenia, thrombocytopenia, and pancytopenia. The most serious adverse effect of acute overdosage of acetaminophen is a dose-dependent, potentially fatal hepatic necrosis. Renal tubular necrosis and hypoglycemic coma also may occur.

Another advantage of the present invention is that the cochleates can be formulated for uptake by particular cells or organs. Conventionally, high levels of drugs are often administered intravenously to obtain moderate levels at the sites of infection in order to combat opportunistic infections. This can cause undesirable side effects, for example, in the case of vancomycin, macular skin rashes, anaphylaxis, phlebitis and pain at the site of intravenous injection, chills, rash, and fever may occur. Also, rapid intravenous infusion may cause a variety of symptoms, including erythematous or urticarial reactions, flushing, tachycardia, and hypotension, generally non-permanent auditory impairment, ototoxicity associated with excessively high concentrations of the drug in plasma and less commonly, nephrotoxicity. By employing the cochleates of the present invention, toxicity levels can be lowered by decreasing the free drug in the circulating blood. Additionally, the cargo moiety can be delivered directly to the site of infection, which can lower or eliminate the incidence of gastrointestinal distress.

Aminoglycosides are very poorly absorbed from the gastrointestinal tract. Less than 1% of the dose typically is absorbed following either oral or rectal administration. Also, inadequate concentrations of aminoglycosides are found in cerebrospinal fluid. Additionally, the drugs are not inactivated in the intestine, and are excreted relatively rapidly by the normal kidney, i.e., they are eliminated quantitatively in the feces. Long-term oral or rectal administration, however, may result in accumulation of aminoglycosides to toxic concentrations in patients with renal impairment. Instillation of these drugs into body cavities with serosal surfaces may result in rapid absorption and unexpected toxicity, i.e., neuromuscular blockade. Similarly, intoxication may occur when aminoglycosides are applied topically for long periods to large wounds, burns, or cutaneous ulcers, particularly if there is renal insufficiency.

Moreover, due to their polar nature, aminoglycosides largely are excluded from most cells, from the central nervous system, and from the eye. Concentrations of conventionally administered aminoglycosides in secretions and tissues are low. High concentrations, however, are found in the renal cortex and in the endolymph and perilymph of the inner ear; this is thought to contribute to the nephrotoxicity and ototoxicity caused by these drugs. Although they are widely used agents, serious toxicity is a major limitation to the usefulness of the aminoglycosides.

Both vestibular and auditory dysfunction can follow the administration of any of the aminoglycosides. Studies of both animals and human beings have documented progressive accumulation of these drugs in the perilymph and endolymph of the inner ear. Accumulation occurs predominantly when plasma concentrations are high. Diffusion back into the bloodstream is slow; the half-lives of the aminoglycosides are five to six times longer in the otic fluids than in plasma. Ototoxicity is more likely to occur in patients with persistently elevated concentrations of drug in plasma. However, even a single dose of tobramycin has been reported to produce slight temporary cochlear dysfunction during periods when the concentration in plasma is at its peak. The relationship of this observation to permanent loss of hearing is not known.

Approximately 8% to 26% of patients who receive an aminoglycoside for more than several days develop renal impairment, which is almost always reversible. The toxicity results from accumulation and retention of aminoglycoside in the proximal tubular cells. The initial manifestation of damage at this site is excretion of the enzymes of the renal tubular brush border. Several variables have been found to influence nephrotoxicity from aminoglycosides, including total amount of drug administered and duration of therapy. Constant concentrations of drug in plasma above a critical level, which is manifested by elevated trough serum concentrations, correlate with toxicity in human beings. Aminoglycosides have the potential to produce reversible and irreversible vestibular, cochlear, and renal toxicity. These side effects complicate the use of these compounds and make their proper administration difficult.

Accordingly, the cochleates of the present invention can be employed to avoid harmful side effects of drugs caused by their high concentration or presence in organs such as the kidneys, stomach or liver.

Echinocandins are a relatively new class of antifungal drugs. Although the most widely known echinocandin, caspofungin, is considered less toxic than other antifungal drugs, (e.g., Amphotericin B), this is not true of the entire class. Caspofungin is especially effective against *Candida* species, however, other members of the echinocandin class have activity against other species, (e.g., *Cryptococcus*). Additionally, echinocandins are generally administered intravenously due to their poor oral absorption. Cochleates of the present invention can be used not only to facilitate oral absorption, but also to avoid potential side effects from this class of compounds.

Safety/Biocompatibility

Cochleates readily can be prepared from safe, simple, well-defined, naturally occurring substances, e.g., PS and calcium. Mixtures of naturally occurring (e.g., soy lipids), synthetic lipids, and/or modified lipids can also be utilized. Phosphatidylserine is a natural component of all biological membranes, and is most concentrated in the brain. The phospholipids used can be produced synthetically, or prepared from natural sources. Soy PS is inexpensive, available in large quantities and suitable for use in humans. Clinical studies indicate that PS is safe and may play a role in the support of mental functions in the aging brain. Unlike many cationic lipids, cochleates (which are composed of anionic lipids) are non-inflammatory and biodegradable. The tolerance in vivo of mice to multiple administrations of cochleates by various routes, including intravenous, intraperitoneal, intranasal and oral, has been evaluated. Multiple administrations of high doses of cochleate formulations to the same animal show no toxicity, and do not result in either the development of an immune response to the cochleate matrix, or any side effects relating to the cochleate vehicle.

The cochleates and cochleate compositions of the present invention can be administered to animals, including both human and non-human animals. It can be administered to animals, e.g., in animal feed or water. For example, antibiotic-cochleates of the present invention can be administered to poultry and other farm animals, including the ruminants and pigs, to control infection or to promote growth or milk production. Among a number of conditions which can be treated with these agents is enteritis, a disease which can cause severe economic losses to livestock producers. Enteritis occurs in chickens, swine, cattle and sheep and is attributed mainly to anaerobic bacteria, particularly *Clostridium perfungens*. Enterotoxemia in ruminants, an example of which is "overeating disease" in sheep, is a condition caused by *C. perfungens* infection. The treatment of such conditions is therefore also encompassed within the methods of the present invention.

Methods of Treatment

In yet another aspect, the present invention provides for both prophylactic and therapeutic methods of treating a subject at risk of (or susceptible to) a disorder or having a disorder which can be treated with one or more cargo moiety.

"Treatment", or "treating" as used herein, is defined as the application or administration of a therapeutic agent (e.g., antibiotics encochleated by cochleates of the invention) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease or disorder. "Treated," as used herein, refers to the disease or disorder being cured, healed, alleviated, relieved, altered, remedied, ameliorated improved or affected. For example, certain methods of treatment of the instant invention provide for administration of anti-inflammatory cochleates, such that inflammation is lessened or alleviated. Other methods of treatment of the instant invention include the administration of antifungal cochleates, such that fungal infection is relieved or remedied.

The terms "cure," "heal," "alleviate," "relieve," "alter," "remedy," "ameliorate," "improve" and "affect" are evaluated in terms of a suitable or appropriate control. A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to administration of a cargo moiety cochleate, as described herein. For example, the number of colony forming units can be determined prior to administering an echinocandin cochleate of the invention to a host. In another embodiment, a "suitable control" or "appropriate control" is a value, level, feature, characteristic, property, etc. determined in a subject, e.g., a control or normal subject exhibiting, for example, normal traits. In yet another embodiment, a "suitable control" or "appropriate control" is a predefined value, level, feature, characteristic, property, etc.

The methods of the present invention include methods of administering a cargo moiety to a host, wherein the cargo moiety is associated with a cochleate or cochleate composition of the invention. The cochleates and cochleate compositions of the present invention may be administered orally, nasally, topically, intravenously, transdermally, buccally, sublingually, rectally, vaginally or parenterally.

The present invention provides a method for treating a subject that would benefit from administration of a composition of the present invention. Any therapeutic indication that would benefit from a cargo moiety, e.g., a drug or nutrient, can be treated by the methods of the invention. Accordingly, the present invention provides methods of treating a subject at risk for or having a disease or disorder which can be treated with, for example, a protein, a small peptide, a bioactive polynucleotide, an antibiotic, an antiviral, an anesthetic, antipsychotic, an anti-infectious, an antifungal, an anticancer, a immunosuppressant, an immunostimulant, a steroidal anti-inflammatory, a non-steroidal anti-inflammatory, an antioxidant, an antidepressant which can be synthetically or naturally derived, a substance which supports or enhances mental function or inhibits mental deterioration, an anticonvulsant, an HIV protease inhibitor, a non-nucleophilic reverse transcriptase inhibitor, a cytokine, a tranquilizer, a mucolytic agent, a dilator, a vasoconstrictor, a decongestant, a leukotriene inhibitor, an anti-cholinergic, an anti-histamine, a cholesterol lipid metabolism modulating agent or a vasodilator agent. The method includes the step of administering to the subject a composition of the invention, such that the disease or disorder is treated. The disease or disorder can be, e.g., inflammation, pain, infection, fungal infection, bacterial infection, viral infection, parasitic disorders, an immune disorder, genetic disorders, degenerative disorders, cancer, proliferative disorders, obesity, depression, hair loss, impotence, hypertension, hypotension, dementia, senile dementia, or malnutrition, acute and chronic leukemia and lymphoma, sarcoma, adenoma, carcinomas, epithelial cancers, small cell lung cancer, non-small cell lung cancer, prostate cancer, breast cancer, pancreatic cancer, hepatocellular carcinoma, renal cell carcinoma, biliary cancer, colorectal cancer, ovarian cancer, uterine cancer, melanoma, cervical cancer, testicular cancer, esophageal cancer, gastric cancer, mesothelioma, glioma, glioblastoma, pituitary adenomas, schizophrenia, obsessive compulsive disorder (OCD), bipolar disorder, Alzheimer's disease, Parkinson's disease, cell proliferative disorders, blood coagulation disorders, Dysfibrinogenaemia and hemophilia (A and B), autoimmune disorders, e.g., systemic lupus erythematosis, multiple sclerosis, myasthenia gravis, autoimmune hemolytic anemia, autoimmune thrombocytopenia, Grave's disease, allogenic transplant rejection, ankylosing spondylitis, psoriasis, scleroderma, uveitis, eczema, dermatological disorders, hyperlipidemia, hyperglycemia, and hypercholesterolemia.

Cochleates of the instant invention can also be used to promote greater health or quality of life, for example limit cholesterol uptake or regulate lipid metabolism, weight gain, hunger, aging, or growth. Cosmetic effects such as wrinkle reduction, hair growth, pigmentation, or dermatologic disorders may also be treated. Cochleates may also treat hereditary disease such as cystic fibrosis or muscular dystrophy.

The cochleates of the instant invention can be used to treat a variety of inflammations, including headache, arthritis, rheumatoid arthritis, osteoarthritis, atherosclerosis, acute gout, acute or chronic soft tissue damage associated with, e.g., a sports injury, tennis elbow, bursitis, tendonitis, acute or chronic back pain, such as a herniated disc, carpal tunnel syndrome, glomerulonephritis, carditis, ulcerative colitis, asthma, sepsis, and plantar fasciitis. The cochleates of the invention can also be used to relieve pain resulting from surgery or other medical procedure. The cochleates of the instant invention can further be used to treat a variety of fungal infections, including candida, e.g., yeast infection, tinea, e.g., Athlete's foot, pityriasis, thrush, *cryptococcal* meningitis, histoplasmosis, and blastomycosis.

The cochleates of the instant invention can also be used to treat a variety of bacterial infections, including but not limited to moderate to severe lower respiratory tract infections, skin infections, biliary tract infections, bone infections, antibiotic prophylaxis, pseudomembranous enterocolitis, central nervous system infections (e.g., meningitis and ventriculitis), intra-abdominal infections (e.g., peritonitis), pneumonia, septicemia, soft tissue infections, neutropenic sepsis, joint infections, infective endocartidis, and urinary tract infections.

Exemplary bacteria that can be treated with the antibiotic preparation of the present invention include, but are not limited to, *Staphylococcus aureus, Staphylococcus epidermidis, Streptococcus pyogenes, Streptococcus pneumuoniae, Streptococcus* Group D, *Clostridium perfungens, Haemophilus influenzae, Escherichia coli, Pseudomonas aeruginosa,* and *Klebsiella pneumoniae.*

The cochleate compositions of the invention are demonstrated herein to effectively mediate the presence of bacteria such as *Pseudomona* and *Staphylococcus*. One species, *S. aureus*, one of the leading causes of hospital acquired infections, causes a wide variety of suppurative diseases, including superficial and deep abscesses, empyema, meningitis, purulent arthritis, and septicemia and endocarditis. In addition, it causes two toxinoses: food poisoning and exfolative skin disease.

*Staphyloccoci* found in infected tissues are mainly located extracellularly. However, virulent *staphylococci* can survive within leukocytes after phagocytosis and may protect themselves against the bactericidal action of antibiotics by means of their intracellular location. Intraphagocytic survival of *S. aureus* has also been observed in patients with various disorders of phagocytic functions. Certain infections caused by *S. aureus* have the tendency to become recurrent, which is attributable to the intraphagocytic survival of small numbers of the organism. Antibiotics that are able to penetrate leukocytes have been shown to have superior clinical efficacy in such recurrent and persistent staphylococcal infections.

Because intracellular residence of infectious agents can complicate treatment, a complete cure can require the eradication of all intracellular bacteria. Therefore, a therapeutic approach that increases the intracellular antibiotic concentration may enhance the bactericidal killing and ensure complete elimination of infection.

*Pseudomonas aeruginosa* infections occur in individuals with altered host defenses, including burn patients, persons with malignant or metabolic disease, or those who have had prior instrumentation or manipulation. Prolonged treatment with immunosuppressive or antimicrobial drugs and radiation therapy also predispose individuals to *Pseudomonas* infections. *P. aeruginosa* is a frequent cause of life-threatening infection, and is the most common cause of nosocomial gram-negative pneumonia, with an associated mortality rate of less than 60%. Among immunocompromised patients, *P. aeruginosa* is a frequent cause of nosocomial bacteremia. In cystic fibrosis, *P. aeruginosa* chronically colonizes the lung, eventually causing respiratory failure and death.

In a preferred embodiment, antibacterial cochleates of the present invention have the ability to reduce the number of bacterial colonies by at least 10%. More preferably, antibacterial cochleates can reduce the number of bacterial colonies by at least 25% and even more preferably by 50%, 75%, 85%, 95%, . . . 100%. All individual values and ranges falling between these ranges and values are within the scope of the present invention.

The present invention also provides a means for treating a variety of fungal infections, including, but not limited to, asthma, chronic rhinosinusitis, allergic fungal sinusitis, sinus mycetoma, non-invasive fungus induced mucositis, non-invasive fungus induced intestinal mucositis, chronic otitis media, chronic colitis, inflammatory bowel diseases, ulcerative colitis, Crohn's disease, candidemia, intraabdominal abscesses, peritonitis, pleural space infections, esophageal candidiasis and invasive aspergillosis. Exemplary fungi that can be treated using antifungal cochleates of the invention include, without limitation, *Absidia, Aspergillus flavus, Aspergillus fumigatus, Aspergillus glaucus, Aspergillus nidulans, Aspergillus terreus, Aspergillus versicolor, Alternaria, Basidiobolus, Bipolaris, Candida albicans, Candida glabrata, Candida guilliermondii, Candida krusei, Candida lypolytica, Candida parapsilosis, Candida tropicalis, Cladosporium, Conidiobolus, Cunninahamella, Curvularia, Dreschlera, Exserohilum, Fusarium, Malbranchia, Paecilonvces, Penicillium, Pseudallescheria, Rhizopus, Schizophy-*

*lum, Sporothrix, Acremonium, Arachniotus citrinus, Aurobasidioum, Beauveria, Chaetomium, Chryosporium, Epicoccum, Exophilia jeanselmei, Geotrichum, Oidiodendron, Phoma, Pithomyces, Rhinocladiella, Rhodoturula, Sagrahamala, Scolebasidium, Scopulariopsis, Ustilago, Trichoderma,* and *Zygomycete.*

*Candida albicans* is part of the normal microbial flora that colonizes mucocutaneous surfaces of the oral cavity gastrointestinal tract, and vagina of many mammals and birds. Because both antibody- and cell-mediated immune responses to *Candida* antigens are evoked in healthy individuals, *C. albicans* colonies are generally infectious for the host. *C. albicans,* however, does not normally cause disease in immunocompetent colonized hosts. It is the setting of congenital, induced, or disease-related immune dysfunction that *C. albicans* causes cutaneous, mucocutaneous, and life-threatening systemic disease.

*C. albicans* is able to not only compete with other microbes but also adhere to and survive on mucosal surfaces of a host with *Candida*-specific antibody and cell-mediated immunity. Numerous putative *C. albicans* virulence factors exist that may enable this opportunistic fungus to survive and thrive in the adverse conditions of host tissues. Among these putative virulence factors, the cell wall of *C. albicans* is one of the most important. The cell wall provides rigidity as well as protection against osmotic lysis, and it promotes infection by supporting the interaction of *C. albicans* adhesins and host-cell receptors. Also, the *C. albicans* cell wall contains mannoproteins which have immunosuppressive properties that can enhance the persistence of the fungus in lesions. Echinocandins, unlike other antifungals, function by interfering with the synthesis of the fungal cell wall.

In a preferred embodiment, echinocandin cochleates of the present invention have the ability to reduce fungal colony forming units (CFU's) by at least 10%. More preferably, echinocandin cochleates can reduce CFU's by at least 25% and even more preferably by 50%, 75%, 85%, 95%, . . . 100%. All individual values and ranges falling between these ranges and values are within the scope of the present invention. Reduction in colony forming units may be in vivo or in vitro. The host of the fungal infection can be a human or non-human animal.

Macrophages are important in the uptake of bacteria, fungi and parasites, and also play an important role in the inflammatory response. In addition to performing phagocytosis, macrophages have the potential of being activated, a process that results in increased cell size, increased levels of lysosomal enzymes, more active metabolism, and greater ability to phagocytose and kill ingested microbes. After activation, macrophages secrete a wide variety of biologically active products that, if unchecked, result in tissue injury and chronic inflammation. One of the secreted products, nitric oxide (NO) has come into the forefront as a mediator of inflammation.

Nitric oxide (NO) produced by inducible NOS plays an important role in inflammation, killing of bacterial pathogens, and tissue repair. NO formation increases during inflammation (i.e., in rheumatoid arthritis, ulcerative colitis, and Crohns disease), and several classic inflammatory symptoms, (i.e., erythema and vascular weakness) are reversed by NOS inhibitors. Nitric oxide has also been recognized as playing a versatile role in the immune system. It is involved in the pathogenesis and control of infectious diseases, tumors, autoimmune processes and chronic degenerative diseases.

Aspirin and acetaminophen are used as anti-inflammatory drugs to relieve pain and fever. The mechanism of action and side effects of these drugs are explained in part by the generation of NO from iNOS. Inhibition of iNOS expression and NO production, therefore, could be a way to therapeutically decrease the inflammatory actions of these drugs.

The above methods can be employed in the absence of other treatment, or in combination with other treatments. Such treatments can be started prior to, concurrent with, or after the administration of the compositions of the instant invention. Accordingly, the methods of the invention can further include the step of administering a second treatment, such as for example, a second treatment for the disease or disorder or to ameliorate side effects of other treatments. Such second treatment can include, e.g., radiation, chemotherapy, transfusion, operations (e.g., excision to remove tumors), and gene therapy. Additionally or alternatively, further treatment can include administration of drugs to further treat the disease or to treat a side effect of the disease or other treatments (e.g., anti-nausea drugs).

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market.

More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment according to that individual's drug response genotype. Pharmacogenomics allows a clinician or physician to target prophylactic or therapeutic treatments to patients who will most benefit from the treatment and to avoid treatment of patients who will experience toxic drug-related side effects.

The language "therapeutically effective amount" is that amount necessary or sufficient to produce the desired physiologic response. The effective amount may vary depending on such factors as the size and weight of the subject, or the particular compound. The effective amount may be determined through consideration of the toxicity and therapeutic efficacy of the compounds by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range that includes the EC50 (i.e., the concentration of the test composition that achieves a half-maximal response) as determined in cell culture. Such information can be used to more accurately determine useful doses in humans. Levels in plasma may be measured, for example, by high performance liquid chromatography.

1. Prophylactic Methods

In one aspect, the invention provides a method for preventing in a subject, a disease or disorder which can be treated with at least one cargo moiety, e.g., a protein, a small peptide, an antiviral, an anesthetic, an anti-infectious, an antifungal, an anticancer, an immunosuppressant, a steroidal anti-inflammatory, a non-steroidal anti-inflammatory, a tranquilizer, a mucolytic agent, a dilator, a vasoconstrictor, a decongestant, a leukotriene inhibitor, an anti-cholinergic, an anti-histamine or a vasodilatory agent. Subjects at risk for a disease or condition which can be treated with the agents mentioned herein can be identified by, for example, any or a combination of diagnostic or prognostic assays known to those skilled in the art. Administration of a prophylactic agent can occur prior to the manifestation of symptoms characteristic of the disease or disorder, such that the disease or disorder is prevented or, alternatively, delayed in its progression. Amphotericin B cochleates, for example, have been administered prophylactically in mice, and were at least as efficacious, if not more efficacious, than Amphotericin B deoxycholate.

2. Therapeutic Methods

Another aspect of the invention pertains to methods of administering a cochleate composition for therapeutic purposes. In one embodiment, the present invention provides a method for treating a subject that would benefit from administration of a composition of the present invention. Any therapeutic indication that would benefit from a cochleate composition of the invention can be treated by the methods of the invention. The present invention provides methods of treating a subject at risk for or having a disease or disorder that can be treated with one or more cargo moiety. The method includes the step of administering to the subject a composition of the invention, such that the disease or disorder is prevented, ameliorated, terminated or delayed in its progression. The disease or disorder can be any of the diseases or disorders discussed herein.

The compositions of the invention can be administered to a subject alone or in combination with a second therapy as described above. The compositions of the invention can be administered to a subject prior to, at the same time, or after a second therapy is administered.

Therapeutic agents can be tested in an appropriate animal model. For example, cochleate compositions of the present invention can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

Pharmaceutical Compositions

The invention pertains to uses of the cochleate compositions of the invention for prophylactic and therapeutic treatments as described infra. Accordingly, the compounds of the present invention can be incorporated into pharmaceutical compositions suitable for administration. Such compositions typically comprise the compositions of the invention and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

Wetting agents, emulsifiers and lubricants, such as sodium lauryl sulfate and magnesium stearate, as well as coloring agents, release agents, sweetening, flavoring and perfuming agents, preservatives and antioxidants may also be present in the compositions.

Examples of pharmaceutically acceptable antioxidants, which may also be present in formulations of therapeutic compounds of the invention, include water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Furthermore, the present invention can further include one or more additional agents, including water, antimicrobial agents, plasticizing agents, flavoring agents, surfactants, stabilizing agents, emulsifying agents, thickening agents, binding agents, coloring agents, sweeteners, fragrances, and the like.

Suitable antimicrobial agents include triclosan, cetyl pyridium chloride, domiphen bromide, quaternary ammonium salts, zinc compounds, sanguinarine, fluorides, alexidine, octonidine, EDTA, and essential oils such as thymol, methyl salicylate, menthol and eucalyptol.

Suitable plasticizing agents include, for example, polyols such as sugars, sugar alcohols, or polyethylene glycols (PEGs), urea; glycol, propylene glycol, triethyl citrate, dibutyl or dimethyl phthalate, monoacetin, diacetin or triacetin.

Suitable surfactants include pluronic acid, sodium lauryl sulfate, mono and diglycerides of fatty acids and polyoxyethylene sorbitol esters, such as, Atmos 300 and Polysorbate 80. Suitable stabilizing agents include xanthan gum, locust bean gum, guar gum, and carrageenan. Suitable emulsifying agents include triethanolamine stearate, quaternary ammonium compounds, acacia, gelatin, lecithin, bentonite, veegum, and the like. Suitable thickening agents include methylcellulose, carboxyl methylcellulose, and the like. Suitable binding agents include starch.

Suitable sweeteners that can be included are those well known in the art, including both natural and artificial sweeteners. Suitable sweeteners include water-soluble sweetening agents such as monosaccharides, disaccharides and polysaccharides; water-soluble artificial sweeteners such as soluble saccharin salts, cyclamate salts, or the free acid form of saccharin, and the like; dipeptide based sweeteners, such as L-aspartic acid derived sweeteners; water-soluble sweeteners derived from naturally occurring water-soluble sweeteners, such as a chlorinated derivative of ordinary sugar (sucrose), known, under the product description of sucralose; and protein based sweeteners such as thaumatoccous danielli (Thaumatin I and II).

In general, an effective amount of auxiliary sweetener is utilized to provide the level of sweetness desired for a particular composition, and this amount will vary with the sweetener selected. This amount will normally be 0.01% to about 10% by weight of the composition when using an easily extractable sweetener.

The flavorings that can be used include those known to the skilled artisan, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, and fruit essences. These flavorings can be used individually or in admixture. Flavorings such as aldehydes and esters including cinnamyl acetate, cinnamaldehyde, citral, diethylacetal, dihydrocarvyl acetate, eugenyl formate, p-methylanisole, and so forth may also be used. Generally, any flavoring or food additive, such as those described in Chemicals Used in Food Processing, publication 1274 by the National Academy of Sciences, pages 63-258, may be used.

The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation.

The compositions of this invention can also contain coloring agents or colorants. The coloring agents are used in amounts' effective to produce the desired color. The coloring agents useful in the present invention include pigments such as titanium dioxide, which may be incorporated in amounts of up to about 5 wt %, and preferably less than about 1 wt %. Colorants can also include natural food colors and dyes suitable for food, drug and cosmetic applications. These colorants are known as FD&C dyes and lakes. A full recitation of all FD&C and D&C dyes and their corresponding chemical structures may be found in the Kirk-Othmer Encyclopedia of Chemical Technology, Volume 5, Pages 857-884, which text is accordingly incorporated herein by reference.

Formulations of the present invention include those suitable for oral, nasal, topical, transdermal, buccal, sublingual, rectal, vaginal or parenteral administration. The formulations may conveniently be presented in unit dosage form and may be prepared by any methods well known in the art of pharmacy. The amount of active ingredient which may be combined with a carrier material to produce a single dosage form will generally be that amount of the composition which produces a therapeutic effect. Generally, out of 100%, this amount will range from about 1% to about 99% of active ingredient preferably from about 5% to about 70%, most preferably from about 10% to about 30%.

Methods of preparing these formulations or compositions include the step of bringing into association a composition of the present invention with the carrier and, optionally, one or more accessory ingredients. In general, the formulations are prepared by uniformly and intimately bringing into association a composition of the present invention with liquid carriers, or finely divided solid carriers, or both, and then if necessary, shaping the product.

Formulations of the invention suitable for oral administration may be in the form of capsules, cachets, pills, tablets, gelcaps, crystalline substances, lozenges (using a flavored basis, usually sucrose and acacia or tragacanth), powders, granules, gel, partial liquid, spray, nebulae, mist, atomized vapor, aerosol, tincture, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) or as mouth washes and the like, each containing a predetermined amount of a composition of the present invention as an active ingredient. A composition of the present invention may also be administered as a bolus, electuary, or paste.

In solid dosage forms of the invention for oral administration (capsules, tablets, pills, dragees, powders, granules, and the like), the active ingredient is mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl-sulfate, and mixtures thereof; and coloring agents.

In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing-agent. Molded tablets may be made by molding in a suitable machine a mixture of the powdered composition moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes or microspheres.

They may be sterilized by, for example, filtration through a bacteria-retaining filter, or by incorporating sterilizing agents in the form of sterile solid compositions which may be dissolved in sterile water, or some other sterile injectable medium immediately before use.

These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient may also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert dilutents, the oral compositions may also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented in liquid or aerosol form, or as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Liquid or aerosol forms include, but are not limited to, gels, pastes, ointments, salves, creams, solutions, suspensions, partial liquids, sprays, nebulaes, mists, atomized vapors, and tinctures. Formulations of the present invention which are suitable for vaginal administration also include pessaries, tampons, creams, gels, pastes, foams or spray formulations containing such carriers as are known in the art to be appropriate.

Formulations of the pharmaceutical compositions of the invention for nasal administration can be in solid, liquid, or aerosol form (e.g., powder, crystalline substance, gel, paste, ointment, salve, cream, solution, suspension, partial liquid, spray, nebulae, irrigant, wash, mist, atomized vapor or tincture).

Dosage forms for the topical or transdermal administration of a composition of this invention include powders, sprays, ointments, pastes, creams, lotions, gels, solutions, patches and inhalants. The composition may be mixed under sterile conditions with a pharmaceutically acceptable carrier, and with any preservatives, buffers, or propellants which may be required.

The ointments, pastes, creams and gels may contain, in addition to an composition of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a composition of this invention, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Transdermal patches have the added advantage of providing controlled delivery of a composition of the present invention to the body. Such dosage forms may be made by dissolving or dispersing the composition in the proper medium. Absorption enhancers may also be used to increase the flux of the composition across the skin. The rate of such flux may be controlled by either providing a rate controlling membrane or dispersing the composition in a polymer matrix or gel.

Ophthalmic formulations, eye ointments, powders, solutions and the like are also within the scope of this invention.

Pharmaceutical compositions of this invention suitable for parenteral administration comprise a cochleate or cochleate composition of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride, in the composition. Prolonged absorption of the injectable compositions can be brought about by including in the composition an agent which delays absorption, for example, aluminum monostearate and gelatin.

Sterile injectable solutions can be prepared by incorporating a composition of the invention in the desired amount in an appropriate solvent with one or a combination of ingredients enumerated above, as required, followed by filtered sterilization. Generally, dispersions are prepared by incorporating the composition into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the cochleate compositions of the invention plus any additional desired ingredient from a previously sterile-filtered solution thereof.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissue.

Oral compositions generally include an inert diluent or an edible carrier. They can be enclosed in gelatin capsules or compressed into tablets. For the purpose of oral therapeutic administration, the composition can be incorporated with excipients and used in the form of tablets, troches, or capsules. Oral compositions can also be prepared using a fluid carrier for use as a mouthwash, wherein the composition in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal-administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions of the invention also can be prepared in the form of suppositories (e.g., with conventional suppository bases such as cocoa butter and other glycerides) or retention enemas for rectal delivery.

In one embodiment, the compositions of the invention are prepared with carriers that will protect the composition against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of a composition calculated to produce the desired therapeutic effect in association with the required pharmaceutical carrier. The specification for the dosage unit forms of the invention are dictated by and directly dependent on the unique characteristics of the composition and the particular therapeutic effect to be achieved, and the limitations inherent in the art of compounding such a composition for the treatment of individuals.

The pharmaceutical compositions can be included in a container, pack, or dispenser together with instructions for administration.

The pharmaceutical compositions can be included in a container along with one or more additional compounds or compositions and instructions for use. For example, the invention also provides for packaged pharmaceutical products containing two agents, each of which exerts a therapeutic effect when administered to a subject in need thereof. A pharmaceutical composition may also comprise a third agent, or even more agents yet, wherein the third (and fourth, etc.) agent can be another agent against the disorder, such as a cancer treatment (e.g., an anticancer drug and/or chemotherapy) or an HIV cocktail. In some cases, the individual agents may be packaged in separate containers for sale or delivery to the consumer. The agents of the invention may be supplied in a solution with an appropriate solvent or in a solvent-free form (e.g., lyophilized). Additional components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The present invention also includes packaged pharmaceutical products containing a first agent in combination with (e.g., intermixed with) a second agent. The invention also includes a pharmaceutical product comprising a first agent packaged with instructions for using the first agent in the presence of a second agent or instructions for use of the first agent in a method of the invention. The invention also includes a pharmaceutical product comprising a second or additional agents packaged with instructions for using the second or additional agents in the presence of a first agent or instructions for use of the second or additional agents in a method of the invention. Alternatively, the packaged pharmaceutical product may contain at least one of the agents and the product may be promoted for use with a second agent.

Figure 29:
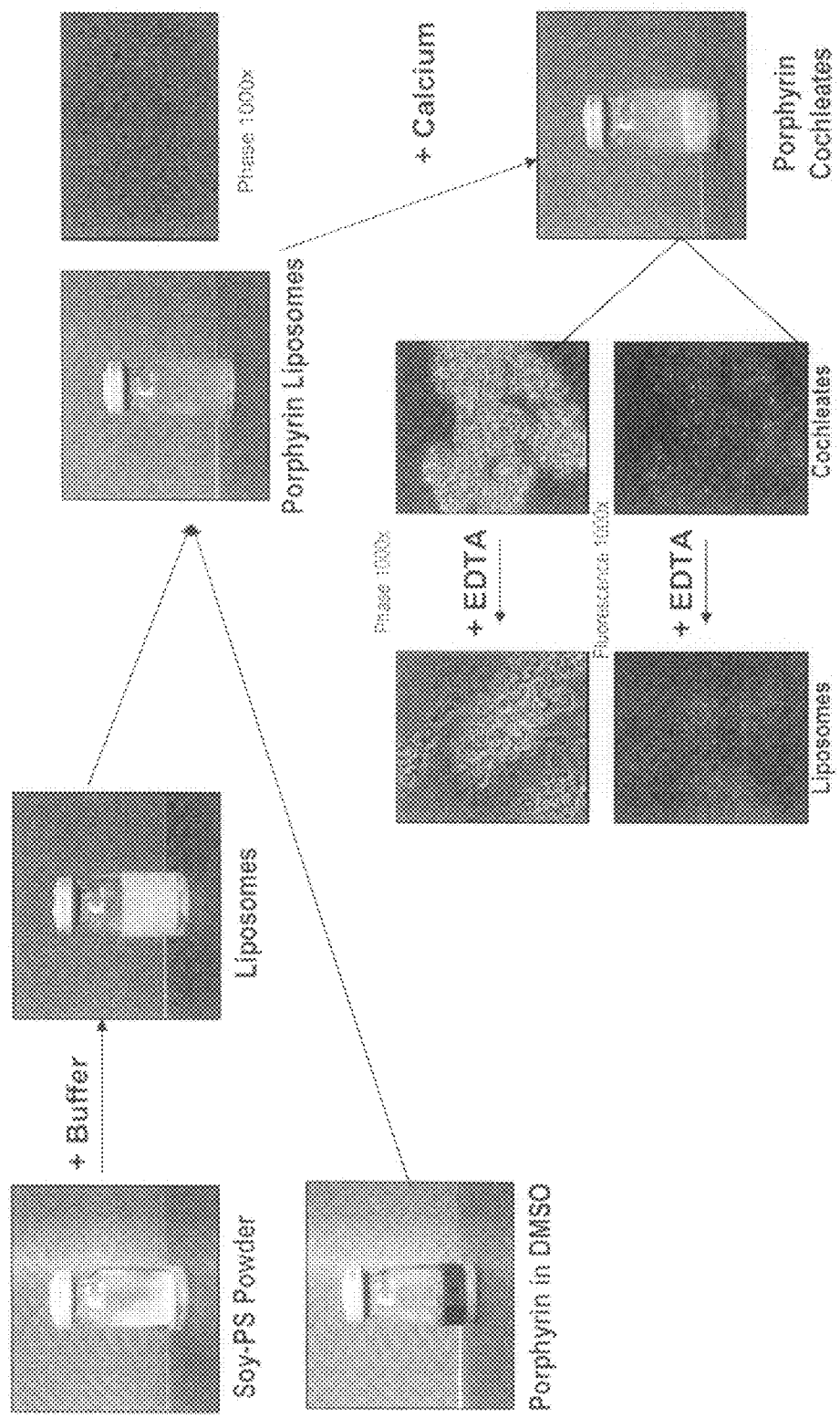
FIG. 29 is a series of images illustrating the use of an exemplary kit of the invention, this is a model compound used as a control.

In yet another aspect, the invention provides an article of manufacture of cochleates and/or cochleate compositions of the invention (FIG. 29). The article of manufacture includes packaging material and a lipid contained within the packaging material. The packaging material includes a label or package insert indicating the use of the lipid for forming cochleates or cochleate compositions of the invention. The article of manufacture can further include instructions or guidelines for the formation of cochleates or cochleate compositions of the invention, e.g., mixing a cargo moiety with a solvent and dripping it into a solution of the lipids. Optionally, the article of manufacture can include a solvent, a cargo moiety, a multivalent cation (e.g., calcium and/or magnesium), a control cargo moiety, and/or a chelating agent (e.g., EDTA).

The article of manufacture may further include other ingredients or apparatus that can be employed to manufacture the compositions of the present invention. One non-limiting example of an article of manufacture would include 5 g of powdered Soy PS, a solution of a model hydrophobic compound in DMSO as a positive control, a solution of calcium chloride to induce cochleate formation, and a solution of EDTA to visualize the opening of the cochleates into liposomes.

The instructions and/or guidelines may generally include one or more of the following statements:

1. Prepare a liposomal suspension by vigorously mixing lipid in water or buffer.

2. Monitor lipid concentrations: low concentration would require a large volume of buffer in order to formulate an adequate amount of end product and high concentration may produce large cochleate aggregates upon the addition of calcium.

3. Experimentally determine whether to use water or buffered solution: the presence of salts and the pH of the suspension may affect the formation of the cargo moiety-liposome intermediate depending on the properties of the cargo moiety.

4. Optionally filter or perform other standard procedures to prepare liposomes of defined size and/or to sterilize the suspension.

5. Prepare a cargo moiety solution with an appropriate solvent: many solvents may potentially be used in this process, e.g., DMSO.

6. Add the cargo moiety-solvent solution, preferably dropwise, to the liposome suspension with vigorous mixing.

7. Experimentally determine the optimal rate of addition and speed of mixing: a suspension of cargo Moiety-liposomes essentially free of unencochleated cargo moiety when viewed by light microscopy should be produced.

8. Calculate the amount of calcium to be added by assuming one mole of calcium for every two moles of lipid, and adding extra calcium to bring the buffer to between 2 and 6 mM.

9. Induce cochleate formation through addition of a calcium salt. The salt may be added as a solution, e.g., 0.1 M calcium chloride, or may be slowly added as a solid calcium salt, e.g., calcium chloride, with vigorous mixing.

10. If the presence of solvent in the buffer is unwanted, optionally harvest the cargo moiety-cochleates, e.g., by centrifugation or filtration, and resuspending them in an appropriate medium. The association of calcium ions with PS is easily reversible, therefore, in order to remain intact and in their crystalline state, cochleate formulations can be resuspended in a medium containing at least 1 to 2 mM calcium ions.

11. Optionally evaluate the quality of the cochleate formulation. The presence of sufficient calcium ions initiates and maintains the cochleate structure. One method of evaluating the quality of a cochleate formulation is visualization of the liposomes that are produced upon removal of the calcium ions from a cochleate crystal. This may be accomplished using light microscopy. An aliquot of a cargo moiety-cochleate suspension may be visualized by phase contrast microscopy at 1000× magnification. A small amount of a concentrated solution of a chelating agent, e.g., EDTA, may be added to the edge of the cover slip, thus reaching the sample through capillary action. A high-quality cochleate product will open into intact liposomes upon contact with the calcium-chelating agent. When using EDTA as the chelating agent, the pH of the EDTA solution should be about pH 9.5. Cochleates will not convert to liposomes at a pH below 6.5. If EDTA solutions at pH 7.4 are used, the release of hydrogen ions upon the binding of calcium to the acetate groups of the chelating agent lowers the pH of the solution and inhibits cochleate conversion to liposomes.

Choice of solvent and other materials, optimal rate of dropwise addition, speed of mixing, the amount of calcium, etc., can readily be determined by the skilled practitioner employing the teachings provided herein.

In addition, a skilled practitioner can introduce, modify and/or eliminate elements and/or steps to the above without departing from the scope of the invention. For example, a liposome suspension might be provided already prepared, a combination of solvents might be used, excess calcium might be used to obviate the calculation of calcium, alternative or additional cations might be employed, etc.

Practice of the invention will be still more fully understood from the following examples, which are presented herein for illustration only and should not be construed as limiting in any way.

EXEMPLIFICATION

Materials and Methods
Materials

The following materials were used, unless otherwise indicated: powdered Amphotericin B (AmB) U.S. Pharmacopela grade was obtained from USP (Rockville, Md.) and Alpharma (Copenhagen, Denmark), and stored at 4° C.; powdered Soy PS was obtained from American Lethicin Corporation (Oxford, Conn.) and Degussa (Champaign, Ill.) and stored at room temperature; Vitamin E (V-E) was obtained from Roche (Parsippany, N.J.); sterile water was obtained from Baxter (Canada); Dioleoylphosphatidyl serine (DOPS) was obtained from Avanti Polar Lipid (Alabaster, Ala.), methyl sulfoxide (DMSO)HPLC grade was obtained from Aldrich (Milwaukee, Wis.), and, micellar AmB/deoxycholate suspension sold under the trademark FUNGIZONE was obtained from Sigma (St. Louis, Mo.).

General Method for Forming Cochleates with a Cargo Moiety

Lipid powder (soy PS or synthetic PS) is dispersed in water (pure water or saline) by vortexing, resulting mixture of unilamellar and multilamellar liposomes. The liposomal suspension is filtered to obtain a suspension having a majority of unilamellar liposomes. To this liposome suspension, a water miscible organic solvent (e.g., DMSO) including a cargo moiety (and optional antioxidant) is introduced. The liposomal suspension is precipitated with cation. The solvent may be removed from the liposomal suspension by tangential flow and/or filtration and/or dialysis, or from the cochleates by washing, filtration, centrifugation, tangential flow, and/or dialysis.

Cell Lines and Culture Conditions

Mouse macrophage J774A.1 cell line and ovarian cancer cell line SKOV3 cell line were obtained from ATCC and PPD, respectively. The cells were grown in monolayers in humidified air with 5% $CO_2$ at 37° C. in 60 $mm^2$ Petri dishes (Corning) containing 5 mL of DMEM supplemented with 10% FBS. For experiments, cells were harvested by scraping (J774A.1) or trypsinization (SKOV3), and were seeded into 24 or 96-well plates at a density of $5 \times 10^5$ cells.

*Staphylococcal aureus* (ATCC 29213) and *Pseudomonas aeruginosa* (ATCC 700289) were maintained weekly on Nutrient agar plates and slants. Fresh cultures were grown up to 24 hours prior to experiment.

Imaging

Phase contrast light microscopy and confocal microscopy (Olympus) was used to image liposomal suspensions, cochleates and cells, with and without the aid of fluorescence, which can be used, e.g., to study cellular uptake and intracellular distribution of fluorescently labeled cochleates and cargo moieties. Confocal microscopy is particularly advantageous as it is a 3-dimensional digital imaging device that can be used to effectively view slices of cell culture. This allows verification of the presence of cochleate and other agents within a cell.

Particle Size Analysis

Two different devices were used to examine particle size. The N4 plus (Coulter) measures particles in the range 10 nm to 3000 nm. The LS230 (Beckman/Coulter) measures particles in the range 40 nm to 1 mm. Using the two devices provides the flexibility and capability to evaluate formulations ranging from nanocochleates to large aggregates of cochleates.

Fraunhofer was used as the optical model for all the experiments. The optical models used to calculate absolute particle size were for spherical particles. Since cochleates are not spherical, the numbers given are relative, not absolute values, but nonetheless allow batch to batch sample comparisons. The results obtained by the two different devices give a qualitative comparison of the size differences between the formulations. However, light and electron microscopy have confirmed that the "nanocochleates" obtained are submicron in size.

Example 1

Amphotericin B Cochleate (CAMB) Prepared with DMSO and Lipid:AmB Ratios of 10:1, 2:1 and 1:1 w/w Amphotericin B cochleates (CAMB) were prepared with Soy PS and DMSO with Vitamin E, and a Lipid to AmB ratio of 10:1 as follows.

Preparation of Liposomes 20 ml of water was added to 200 mg of Soy-PS in a 50 ml plastic tube, vortexed for about 15 minutes to form a liposomal suspension, and filtered using a 0.45 µm filter. The suspension was sonicated for about 4 minutes and filtered again with a 0.22 µm filter.

Addition of Cargo Moiety and Antioxidant in Solvent 1.90 ml of DMSO solvent was added to 20 mg of Amphotericin B in a 15 ml plastic tube. To the AmB/DMSO mixture, 0.1 ml of Vitamin E (20 mg/ml in DMSO), vortexed for about 10 minutes. This solution was then added to the liposomal suspension by drop wise addition using a 1 ml pipette while vortexing. The final mixture was vortexed for about 2 minutes.

Precipitation of Cochleates 2 ml of calcium (0.1 N) was added to the liposomal suspension at a rate of 10 µl/10 s while vortexing to form cochleates.

Solvent Removal/Washing

The mixture was vortexed for about 1-2 minutes, centrifuged for about 1 hours at 9000 rpm, and the supernatant was removed and replaced with fresh supernatant (water with 2 mM calcium). This washing step was repeated once.

Employing the above method, cochleates having a lipid to drug ratio 2:1 and 1:1 also were prepared by varying the ingredients to conform to following formulations.

TABLE 1

Cochleate Formulations

| | CAMB 1:1 | CAMB 2:1 |
|---|---|---|
| Soy PS (mg) | 100 | 200 |
| AmB (mg) | 100 | 100 |
| Vitamin E (mg) | 1 | 2 |
| DMSO (ml) | 2 | 2 |
| Water (ml) | 10 | 20 |
| Calcium (ml) | 1 | 2 |
| Washings with sterile water w/calcium (1 mM) | 2 | 2 |
| Final Volume (ml) | 10 | 20 |

Summary of Results

For each cochleate formulation, a yellowish suspension with some of the cochleates floating on the top and/or residing on the bottom of the suspension were observed macroscopically.

Figure 4:
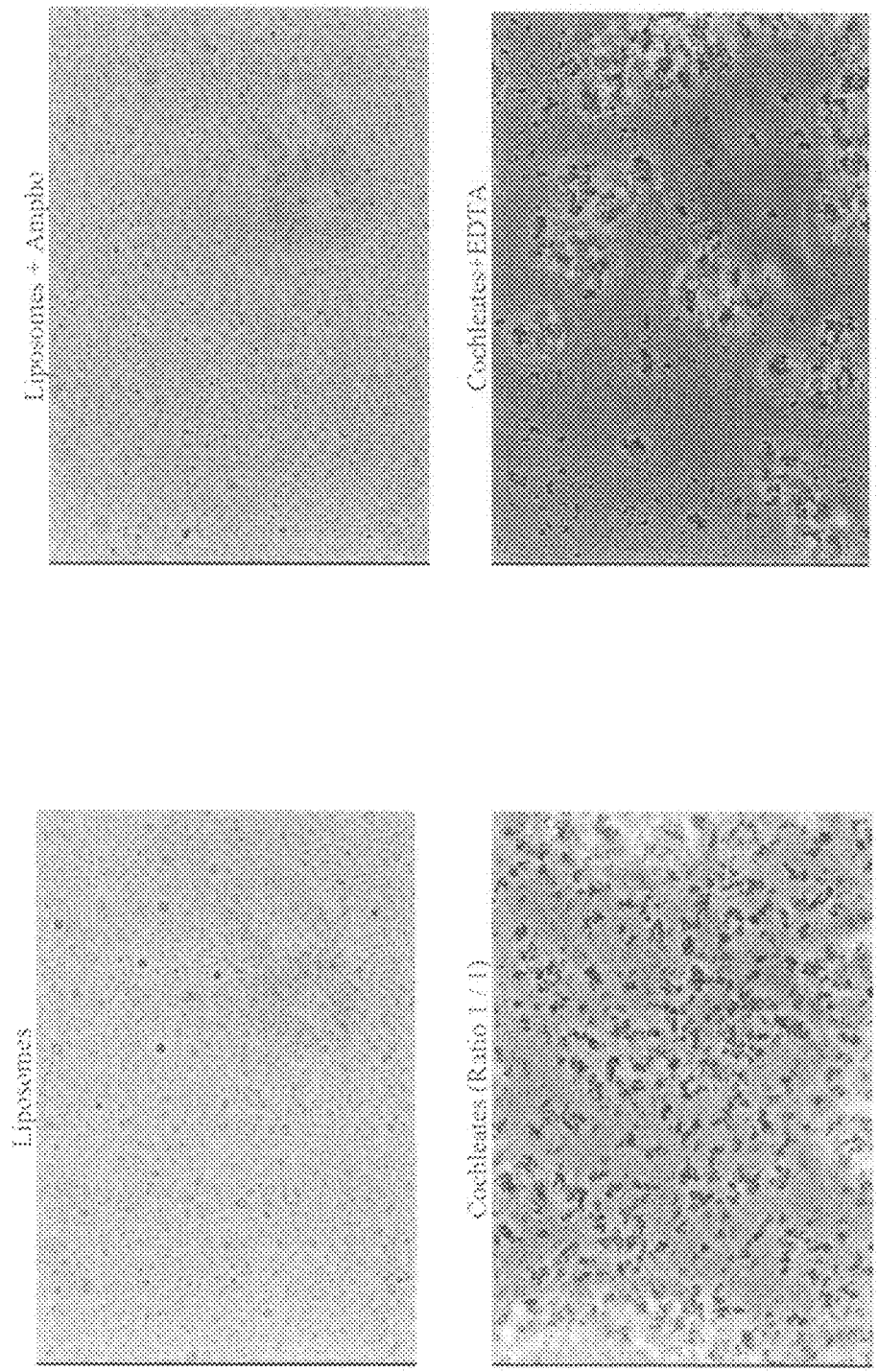
FIG. 4 is a series of images of an Amphotericin B formulation having a lipid to drug ratio of 1:1 at different stages in the formulation: liposomes, liposomes with AmB, cochleates, and cochleates after addition of EDTA.
Figure 5:
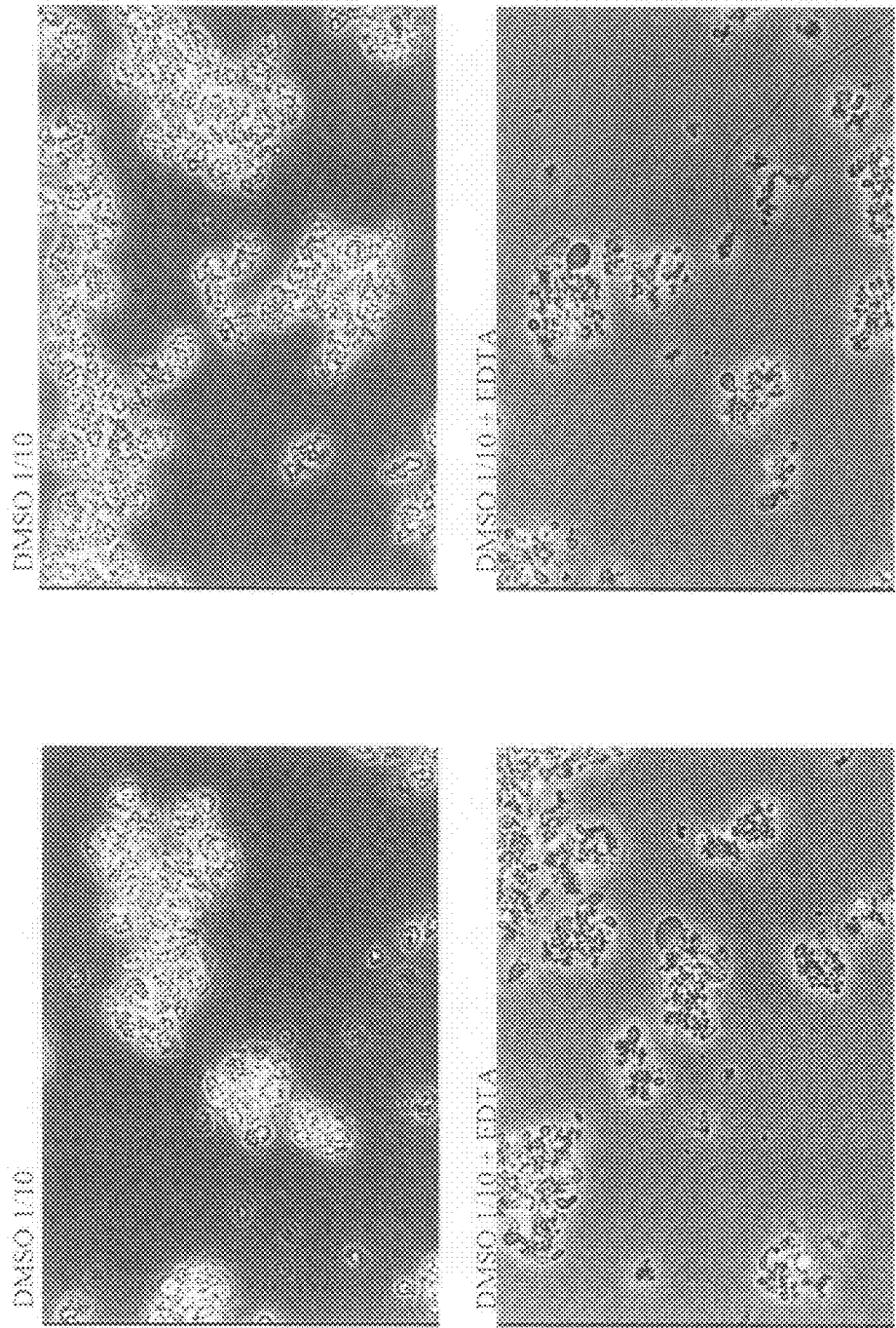
FIGS. 5, 6 and 7 are each a series of images, before and after addition of EDTA, of AmB-cochleate formulations having a lipid to drug ratio of 10:1, 2:1, and 1:1 ratio, respectively.
Figure 6:
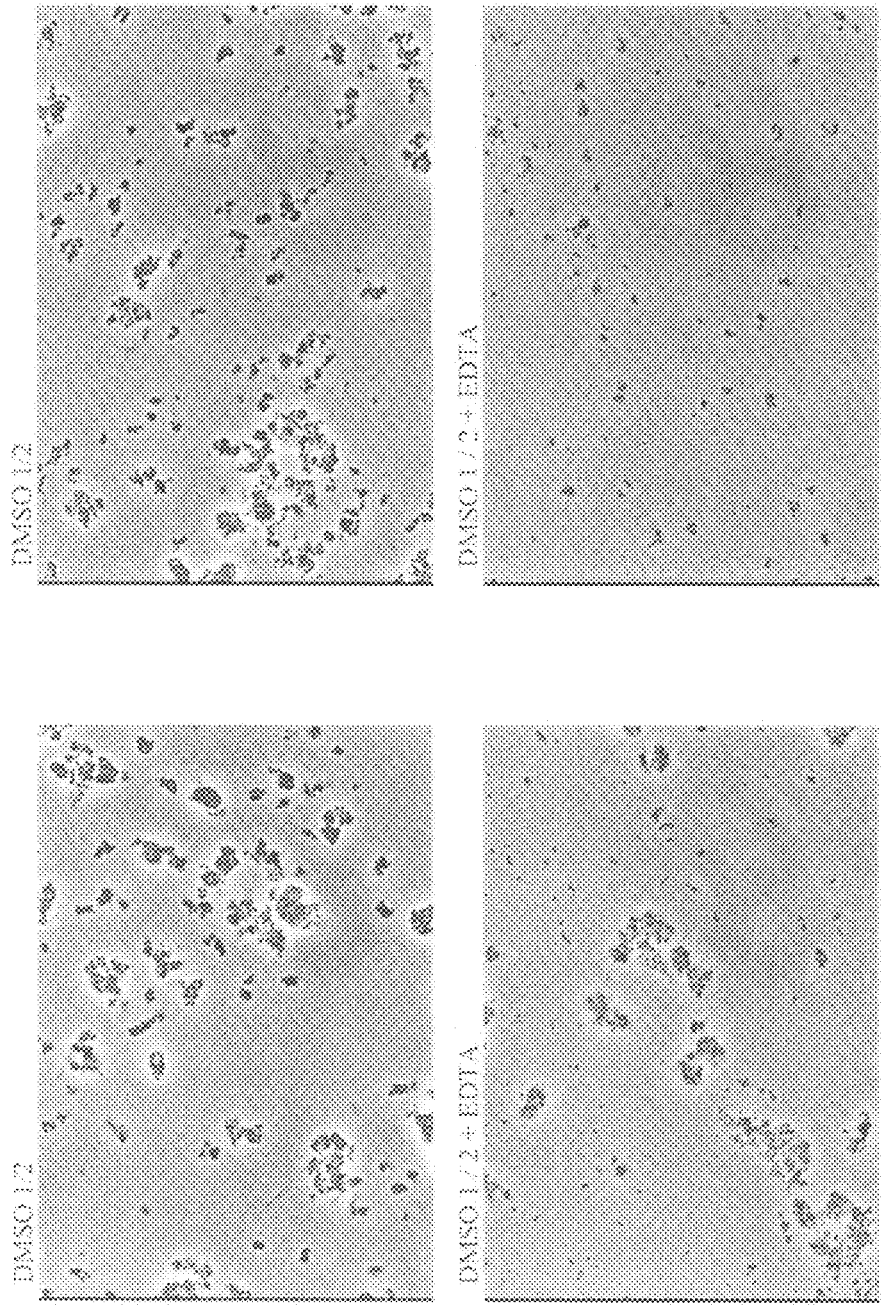
Figure 7:
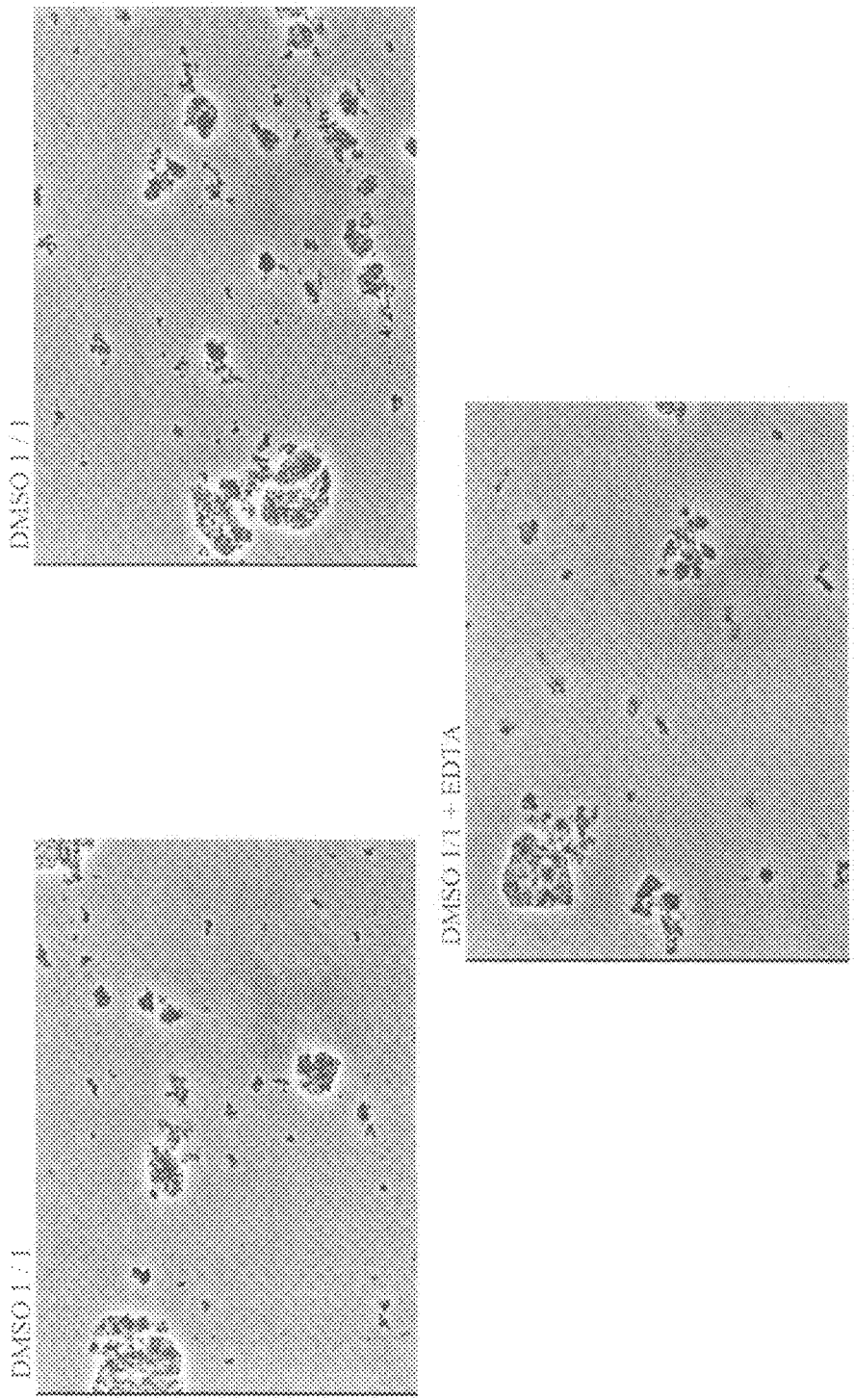

FIG. 4 is a series of images of the formulation having a 1:1 ratio at different stages in the formulation: liposomes, liposomes with AmB, cochleates, and cochleates after addition of EDTA. FIGS. 5, 6 and 7 are each a series of images, before and after addition of EDTA, of the cochleate formulations having a 10:1, 2:1, and 1:1 ratio, respectively.

Figure 8:
FIG. 8 is a graph of the size distribution of the liposomes after vortexing and prior to filtration, after filtration with 0.45 μm filter, and after introducing DMSO/Amphotericin.
Figure 9:
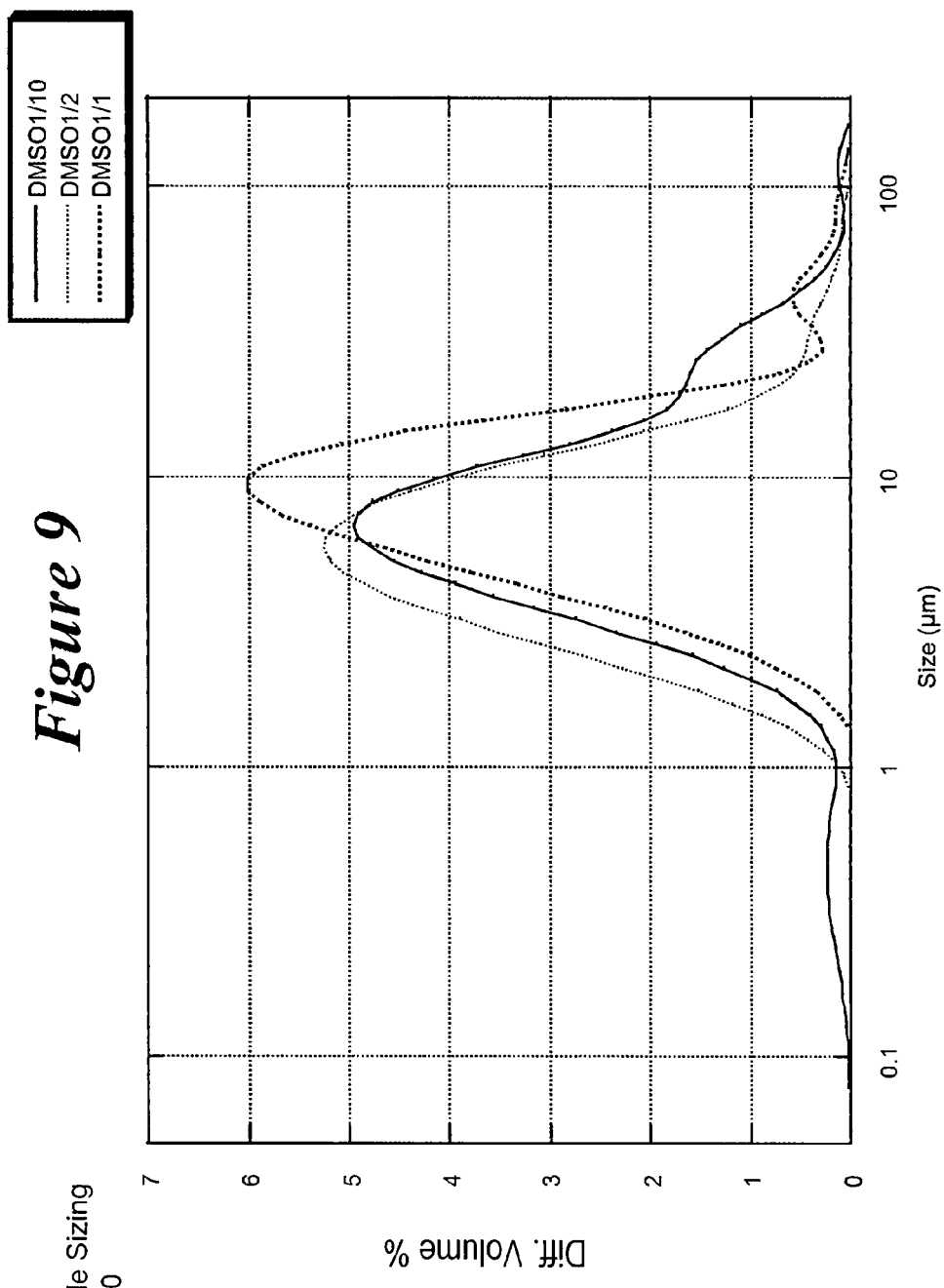
FIG. 9 is a graph of the size distribution of cochleate formulations having lipid to AmB ratios of 10:1, 2:1 and 1:1.

FIG. 8 is a graph of the size distribution of the liposomes after vortexing and prior to filtration, after filtration with 0.45 µm filter, and after introducing DMSO/Amphotericin. FIG. 9 is a graph of the size distribution of cochleate formulations having lipid to AmB ratios of 10:1, 2:1 and 1:1.

Example 2

Amphotericin B Cochleates Prepared with NMP

Cochleates were prepared as described in Example 1, except N-methylpyrrolidone (NMP) solvent was used instead of DMSO, and the formulation was adjusted as indicated in the following table.

TABLE 2

NMP 10:1 Formulation

| | CAMB/NMP 10:1 |
|---|---|
| Soy PS (mg) | 200 |
| AmB (mg) | 20 |
| Vitamin E (mg) | 2 |
| DMSO (ml) | 2 |
| Water (ml) | 20 |
| Calcium (ml) | 2 |
| Washings with sterile water w/calcium (1 mM) | 2 |
| Final Volume | 20 ml |

Cochleates in the final formulations were observed as a yellowish suspension. Mice infected with a lethal dose of *Aspergillus fumigatus* were dosed with 2 mg/kg of the AmB-cochleate formulation for 14 days. The cochleates were efficacious against the *A. fumigatus*.

Example 3

Amphotericin B Cochleates Prepared with DMSO and Lipid:AmB Ratios of 5:1, 4:1, 3:1 and 2:1 w/w Amphotericin B cochleates (CAMB) were prepared with soy PS and DMSO with tocopherol (Vitamin E) with the following protocol:

1. Weighing and placing 300 mg of soy PS into a 50 ml pp sterile tube with 10 ml sterile water.
2. Vortexing the suspension for 2 minutes.
3. Sonicating the suspension for 3 minutes.
4. Filtering the suspension with a 0.22 μm filter and pooling liposomes into a 50 ml tube.
5. Weighing and placing 10 mg (5:1), 12.5 mg (4:1) 16.6 mg (3:1) and 25 mg (2:1), of AmB (individually) into four 15 ml pp sterile tubes with 0.5 ml DMSO and vortexing.
6. Adding 6.0 μl (5:1), 6.2 μl (4:1), 6.6 μl (3:1), and 7.5 μl (2:1) of tocopherol at 10 mg/ml in DMSO to the 15 ml tubes with AmB. (The concentration of the AmB was 20 mg/ml 5:1), 25 mg/ml (4:1), 33.2 mg/ml (3:1), and 50 mg/ml (2:1), at this time)
7. Vortexing the solution for a few minutes until the AmB completely dissolved.
8. Adding 5 ml of liposomes to each AmB/Vitamin E/DMSO solution, and vortexing the sample for a few minutes.
9. Adding 0.5 ml of 0.1M calcium solution into the suspension with vortexing, using an eppendorf repeater pipette with a 500 μl tip and adding 10 μl aliquots to the tube per every 10 sec.
10. Centrifuging the suspension for 30 minutes at 9000 rpm at 4° C.
11. Removing the supernatant from the tube and re-suspending the pellet with the same volume of wash buffer (sterile water with 2 mM calcium).
12. Repeating steps 10 and 11 two more times. Adjusting the final volume of the suspension to 6 ml with wash buffer.
13. Examining the final preparation under a microscope and confirming the pH of 5.5.
14. Streaking the sample on a chocolate plate to check the sterilization of the final preparation and incubating plates at 37° C., 4° C., and room temperature for 24 hrs, 48 hrs, and 72 hrs.
15. Storing the sample, treated with nitrogen and covered with parafilm, at 4° C.

The following table summarizes the above formulations.

TABLE 3

CAMB Preparations

| Name of Sample | PS:AmB (w/w) | AmB | Soy PS | V-E | AmB liposome | 0.1M Calcium | Final AmB (mg/ml) |
|---|---|---|---|---|---|---|---|
| CAMB 5:1 | 5:1 | 10 mg | 50 mg | 60 μg | 5.5 ml | 0.5 ml | 1.66 mg/ml |
| CAMB 4:1 | 4:1 | 12.5 mg | 50 mg | 62.5 μg | 5.5 ml | 0.5 ml | 2.08 mg/ml |
| CAMB 3:1 | 3:1 | 16.6 mg | 50 mg | 66.6 μg | 5.5 ml | 0.5 ml | 2.76 mg/ml |
| CAMB 2:1 | 2:1 | 25 mg | 50 mg | 75 μg | 5.5 ml | 0.5 ml | 4.16 mg/ml |

About 0.5 ml DMSO was used in each preparation. HPLC and LC/MS were used to measure the AmB and DMSO concentrations.

Summary of Results
1. Macroscopic observations: yellowish suspension.
2. Microscopic observations: cochleates with different size of aggregates.
3. Addition of EDTA: liposomes formed after addition of EDTA (chelator).
4. Recovery: HPLC analysis indicated that approximately 100% of the AMB was successfully encochleated.
5. For the mouse study described in Example 4, the following amounts of each formulation were set aside:
   5:1=>0.4 mg/ml×1.2 ml, 14 bottles
   4:1=>0.4 mg/ml×1.2 ml, 14 bottles
   3:1=>0.4 mg/ml×1.2 ml, 14 bottles
   2:1=>0.4 mg/ml×1.2 ml 14 bottles For the in vitro study described in Example 5, the following amounts of each formulation were set aside:
   5:1=>0.34 mg/ml×100 ul (Conc: PS=1.7 mg/ml)
   4:1=>0.42 mg/ml×100 ul (Conc: PS=1.7 mg/ml)
   3:1=>0.56 mg/ml×100 ul (Conc: PS=1.7 mg/ml)
   2:1=>0.85 mg/ml×100 ul (Conc: PS=1.7 mg/ml)
6. Sterility: No bacteria observed in the formulations after 72 hrs.

Example 4

Efficacy Studies in Mice

The formulations of Example 3 were administered to mice to study the efficacy of the formulations to protect mice from a lethal dose of *Candida albicans*, and to clear the organs of *C. albicans* in the surviving mice.

Figure 10:
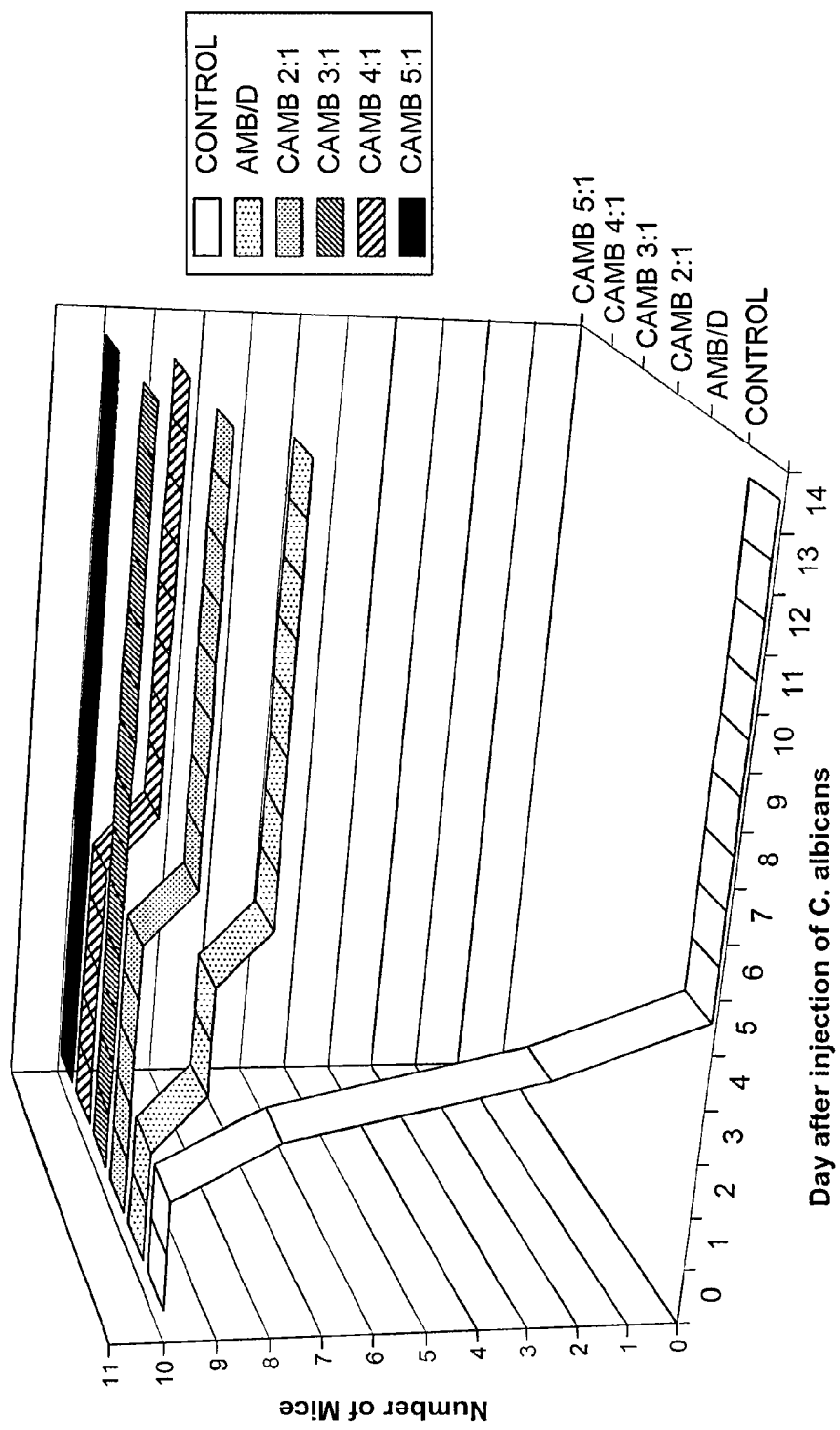
FIG. 10 is a graph of the survival data for *C. albicans*-infected mice untreated (control), or dosed daily for 14 days with AmB/deoxycholate, or AmB-cochleates with a lipid to drug ratio of 2:1, 3:1, 4:1, or 5:1.

Six groups of 10 mice were studied. The mice were administered $5 \times 10^5$ cells *C. albicans* intravenously through the tail vein. Starting 24 hours post-infection, the following compositions were administered to each group orally once daily at 2 mg AmB/kg body weight for 14 days, except for the control group which remained untreated.
   a. Control (untreated)
   b. AmB/deoxycholate (FUNGIZONE)
   c. CAMB 2:1 AmB
   d. CAMB 3:1 AmB
   e. CAMB 4:1 AmB
   f. CAMB 5:1 AmB Appearance and behavior was monitored each day of the study. Tissue burden of *C. Albicans* was determined in kidney, liver and lungs for each animal, and colony counts were taken. Organs were obtained and weighed, homogenized, dilutions in buffer made, and aliquots plated onto plates; colony counts of fungus were taken several days later. FIG. 10 is a graph of the survival data for *C. albicans*-infected mice untreated (control), or dosed daily for 14 days with AmB/deoxycholate, or AmB-cochleates with a lipid to drug ratio of 2:1, 3:1, 4:1, or 5:1.

Figure 11:
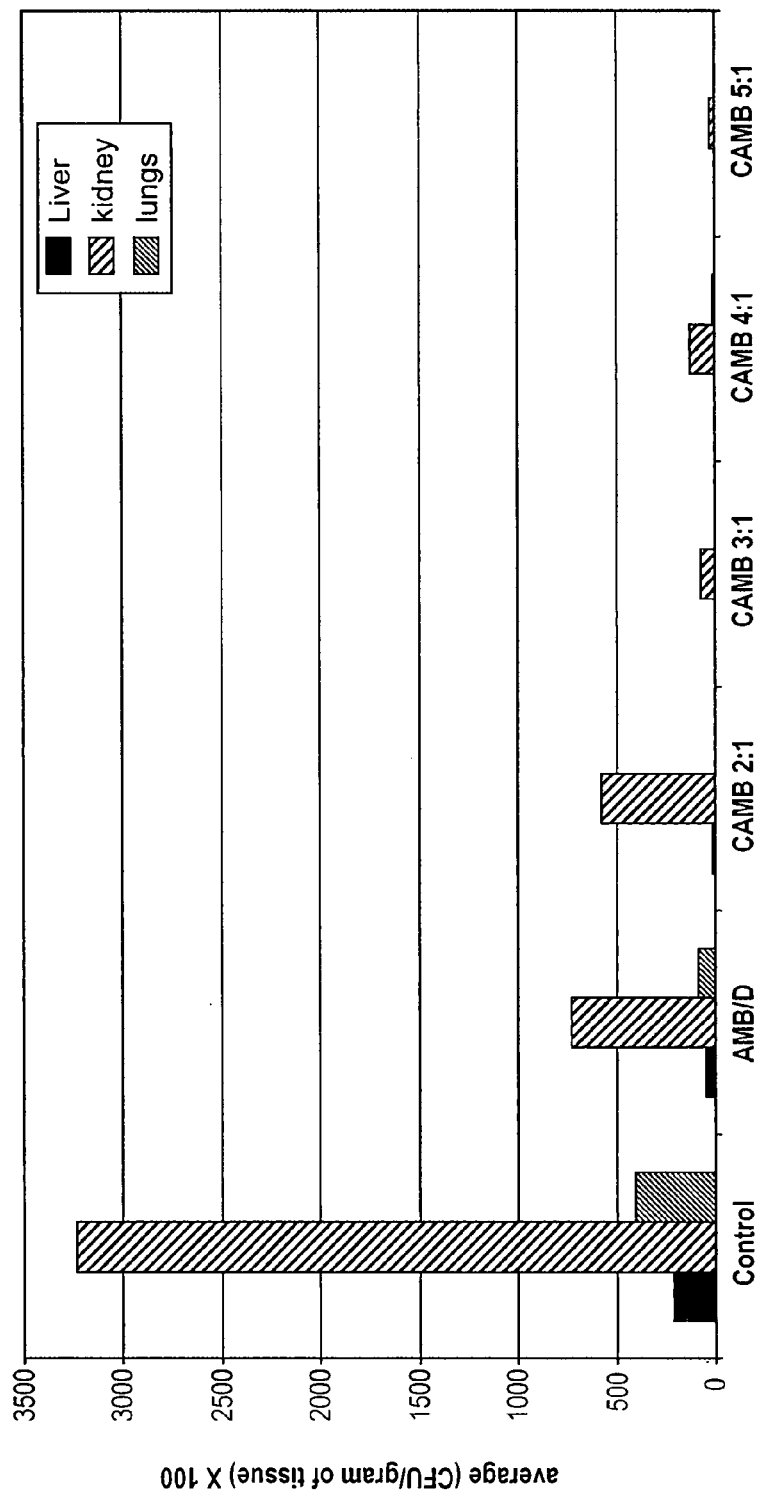
FIG. 11 is a chart of the average number of *C. albicans* cells/gram of tissue in the liver, kidney, and lungs of *C. albicans*-infected mice untreated and dosed daily for 14 days with AmB/deoxycholate, or AmB-cochleates with a lipid to drug ratio of 2:1, 3:1, 4:1, or 5:1.

FIG. 11 is a chart of the average number of *C. albicans* cells/gram of tissue in the liver, kidney, and lungs of *C. albicans*-infected mice untreated and dosed daily for 14 days with AmB/deoxycholate, or AmB-cochleates with a lipid to drug ratio of 2:1, 3:1, 4:1, or 5:1.

One hundred percent of the control (untreated) group did not survive the study and showed high tissue burdens. All four AmB-cochleate (CAMB) formulations were effective in preventing mortality and reducing fungal cell burdens in target organs (kidneys, lungs and liver). The CAMB 5:1 and CAMB 3:1 formulation appeared somewhat better than the others clearing the liver and lungs completely (the principal target organ for *C. albicans* (kidney) was not completely cleared). The CAMB 5:1 formulation appeared to be the most effective versus the others in reducing fungal cell burdens in the kidneys. In general, the CAMB formulations were more effective than the AmB/deoxycholate formulation.

Example 5

Efficacy Studies in Cells

The relative efficacy of the compositions of Example 3 were studied in J774A.1 macrophages to compare the relative efficacy of the cochleate compositions (5:1, 4:1, 3:1 and 2:1) against *Candida albicans*.

Macrophages were seeded into a 96-well plate and incubated overnight as described above. Following incubation, the macrophages were infected with *C. albicans* at a ratio of 1:200 with respect to the macrophages. The AmB-cochleates were then added at the concentrations of 0.1, 0.01 and 0.001 µg. Twenty-four hours later, the cell cultures were lysed, samples were plated onto agar plates, and colonies were counted the following day.

Figure 12:
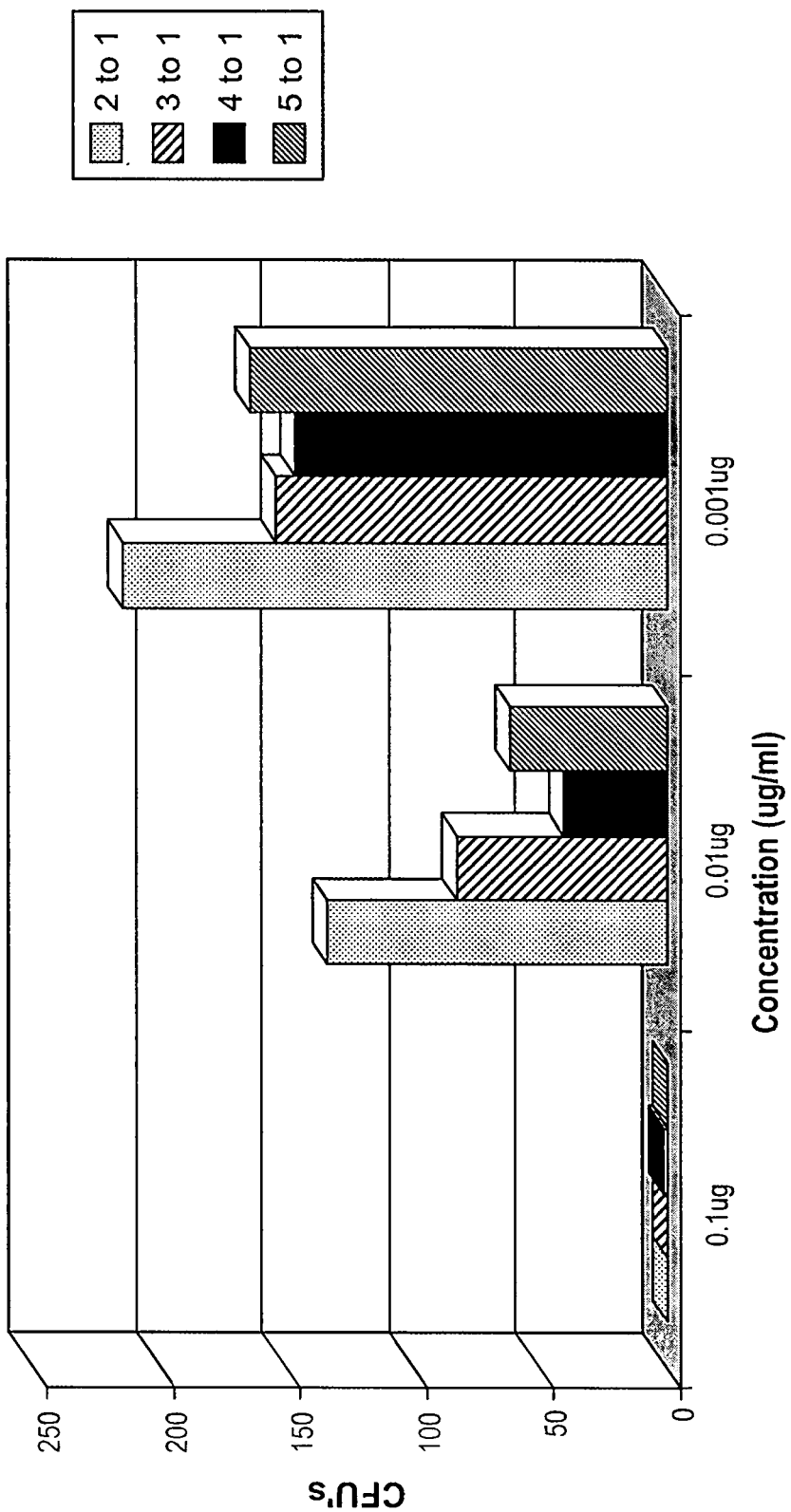
FIG. 12 is a graph of the number of colony forming units (CFU) for the *C. albicans*-infected macrophages dosed with varying concentrations of AmB-cochleates with lipid to drug ratios of 2:1, 3:1, 4:1, and 5:1.

FIG. 12 is a graph of the number of colony forming units (CFU) for the *C. albicans*-infected macrophages dosed with varying concentrations of AmB-cochleates with lipid to drug ratios of 2:1, 3:1, 4:1, and 5:1. All cochleate formulations were efficacious at killing *C. albicans*;

Example 6

Amphotericin B Cochleates Prepared with DMSO and Lipid:AmB Ratios of 5:1, 2:1, and 1:1 w/w Multiple batches of Amphotericin B cochleates (CAMB) were prepared with DMSO and tocopherol (Vitamin E) by the following steps. Two methods for the removal of solvent were employed: removal of solvent by washing the cochleates and removal of solvent by dialysis of the liposomal suspension.
1. Weighing and placing 100 mg of soy PS into a 50 ml pp sterile tube with 10 ml sterile water.
2. Vortexing the suspension for 2 minutes.
3. Sonicating the suspension for 3 minutes.
4. Filtering the suspension with a 0.22 um filter and pooling the liposomes into a 50 ml tube.
5. Weighing and placing 10 mg (5:1), 25 mg (2:1), and 50 mg (1:1) of AmB into 4, 15 ml pp sterile tubes with 0.5 ml DMSO (1 ml DMSO for 1:1).
6. Adding 7.5 µl (2:1), 6.0 µl (5:1), and 10 µl (1:1) of tocopherol at 10 mg/ml to the DMSO (the concentration of the AmB will be 20 mg/ml (5:1), 50 mg/ml (2:1), and 50 mg/ml (1:1) at this time),
7. Vortexing the solution for a few minutes until the AmB dissolved completely.

Remainder of Method when Removing Solvent by Washing Cochleates
1. Mixing 5 ml of liposome with 0.507 ml of the AmB/DMSO suspension, and vortexing the sample for a few minutes.
2. Adding 0.5 ml of 0.1M calcium solution into the suspension with vortexing, using an eppendorf repeater pipette with a 500 ul tip and adding 10 µl aliquots to the tube per every 10 sec.
3. Centrifuging the suspension for 30 minutes at 9000 rpm at 4° C.
4. Removing the supernatant from the tube and re-suspending the pellet with wash buffer of same volume (2 mM calcium with sterile water).
5. Repeating steps 3 and 4. Adjusting the final volume of the suspension to 5 ml with 2 mM calcium wash buffer.

Remainder of Method when Removing Solvent by Dialysis of Liposomes
1. Transferring 6 ml (1:1), and 5.5 ml (2:1 and 5:1), of AmB/DMSO/liposomes into dialysis tubes individually.
2. Starting the removal the DMSO using dialysis by changing the sterile water several times and leaving overnight.
3. On the next day, transferring the AmB/liposomes into the 50 ml sterile tubes, and saving 0.5 ml of AmB/liposomes for the HPLC analysis.
4. Precipitating the liposomes by adding 0.5 ml of 0.1M calcium to each 50 ml tube of AmB/liposomes. About 6.0 ml were precipitated for the 5:1 and 2:1 samples, and 6.5 ml were precipitated for the 1: sample 500 µl of liposomes were saved for the HPLC assay from each sample. The pH was about 4.0 at this point after dialysis, and was readjusted to a pH of 5.5 to 6.0 with 1N NaOH in final preparation.

Sterilization/Stability/Storage of Preparations
1. Stability: The final preparations from both methods were examined under a microscope, and the pH (about 5.5) was confirmed.
2. Sterility: Samples of each preparation were streaked on a chocolate plate to check the sterilization of the final preparation, and incubated at 37° C., 4° C., and room temperature for 24 hrs, 48 hrs, and 72 hrs.
3. Storage: The samples, treated with nitrogen and covered with parafilm, were stored a 4° C.

The above formulations can be summarized as follows.

TABLE 4

CAMB Formulations

| Name of Sample | Ratio of PS:AmB(w/w) | Amount of AmB | Amount of soy PS | Tocopherol | AmB liposome | 0.1M Calcium | Final Conc. Of AmB (mg/ml) |
|---|---|---|---|---|---|---|---|
| AmB/DMSO (washing) | 2:1 | 25 mg | 50 mg | 75 µg | 5.5 ml | 0.5 ml | ≈5 mg/ml |
| AmB/DMSO (dialysis) | 5:1 | 10 mg | 50 mg | 60 µg | 5.5 ml | 0.5 ml | 1.52 mg/ml |
| AmB/DMSO (dialysis) | 2:1 | 25 mg | 50 mg | 75 µg | 5.5 ml | 0.5 ml | ≈3.8 mg/ml |
| AmB/DMSO (dialysis) | 1:1 | 50 mg | 50 mg | 100 µg | 6.0 ml | 0.5 ml | ≈7.1 mg/ml |

The recovery of AmB was determined using HPLC assay.

Figure 13:
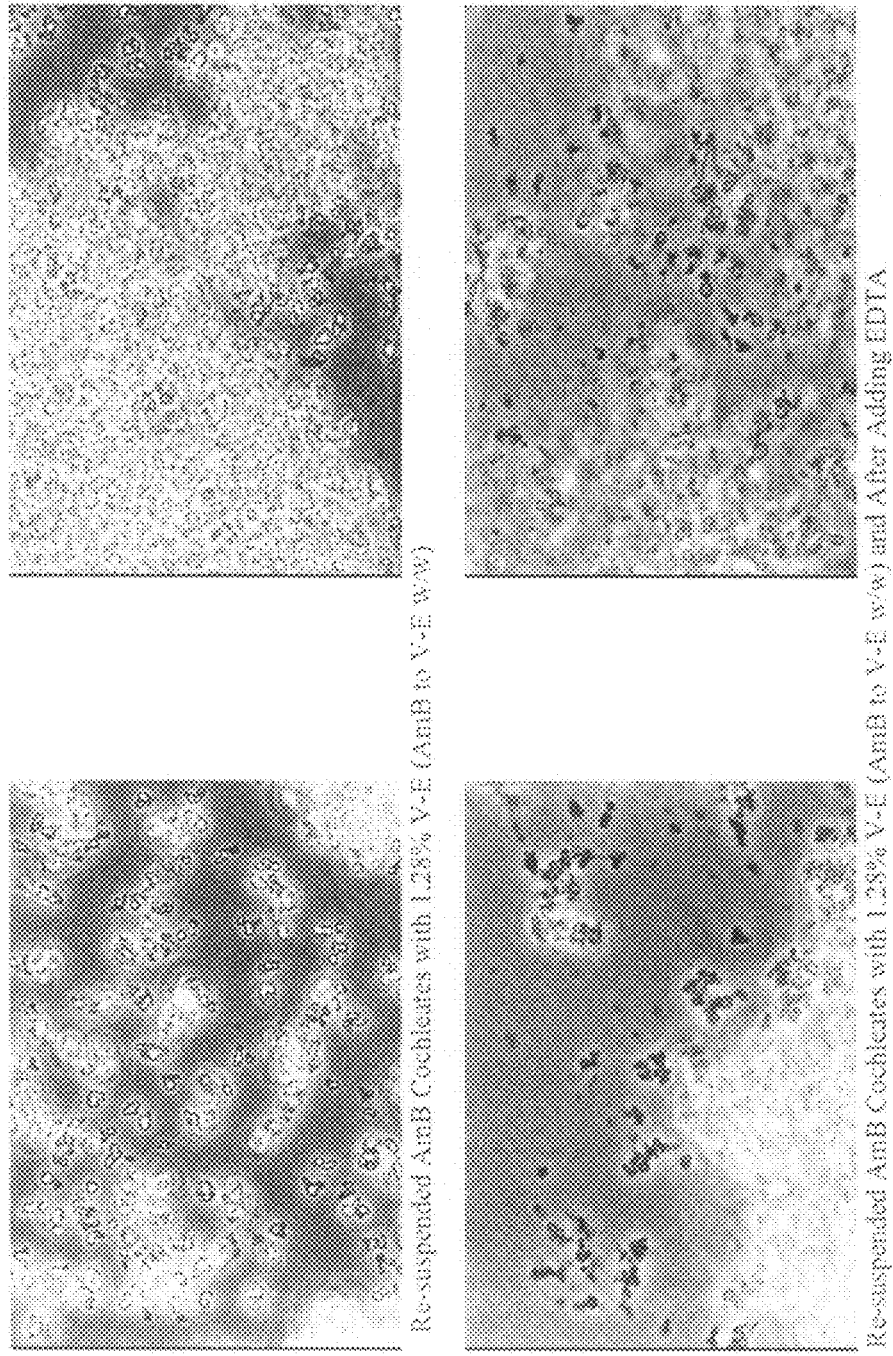
FIG. 13 is a series of images of the 5:1 AmB cochleates (top two panels) and the cochleates after addition of EDTA (bottom two panels).

Results
1. Macroscopic observations: yellowish suspension with some settles on the bottom of the tubes.
2. Microscopic observations: aggregated and individual cochleates were observed.
3. Addition of EDTA: liposomes formed upon addition of EDTA
4. Images of cochleate: FIG. 13 is a series of images of the 5:1 AmB cochleates (top two panels) and the cochleates after addition of EDTA (bottom two panels).
5. Recovery: HPLC analysis indicated that following amounts of AmB encochleated for each formulation indicated.

2:1 (Washing)=>81%

5:1 (Dialysis)=>91%

2:1 (Dialysis)=>92%

1:1 (Dialysis)=>92%

7. Outcome: For the mouse study described in Example 7, the following amounts of each formulation were set aside:

2:1 (Washing)=>0.2 mg/ml×2.5 ml, 14 bottles

5:1 (Dialysis)=>0.2 mg/ml×2.2 ml, 14 bottles (using $2^{nd}$ batch)

2:1 (Dialysis)=>0.2 mg/ml×2.5, 14 bottles

1:1 (Dialysis)=>0.2 mg/ml×2.5 ml 14 bottles

Example 7

Efficacy Studies in Mice

The formulations of Example 6 were administered to mice to study the efficacy of the formulations to protect mice from a lethal dose of Candida albicans, and to clear the organs of C. albicans in the surviving mice.

Six groups of 10 mice were studied. The mice were administered $10^6$ cells C. albicans intravenously through the tail vein. Starting 24 hours post-infection, the following compositions were administered to each mouse once daily at 2 mg/kg orally for 14 days, except for the control group, which remained untreated.

a. Control Group (untreated)

b. AmB/deoxycholate c. CAMB 2:1 (Washed)

d. CAMB 5:1 (Dialysis)

e. CAMB 2:1 (Dialysis)

f. CAMB 1:1 (Dialysis)

Appearance and behavior was monitored each day of the study. Tissue burdens of C. albicans were determined in kidney, liver and lungs for each animal at the end of the study, and colony counts were taken. Organs were obtained and weighed, homogenized, dilutions in buffer made, and aliquots plated onto plates and colony counts of fungus taken several days later.

Summary of Results

Figure 14:
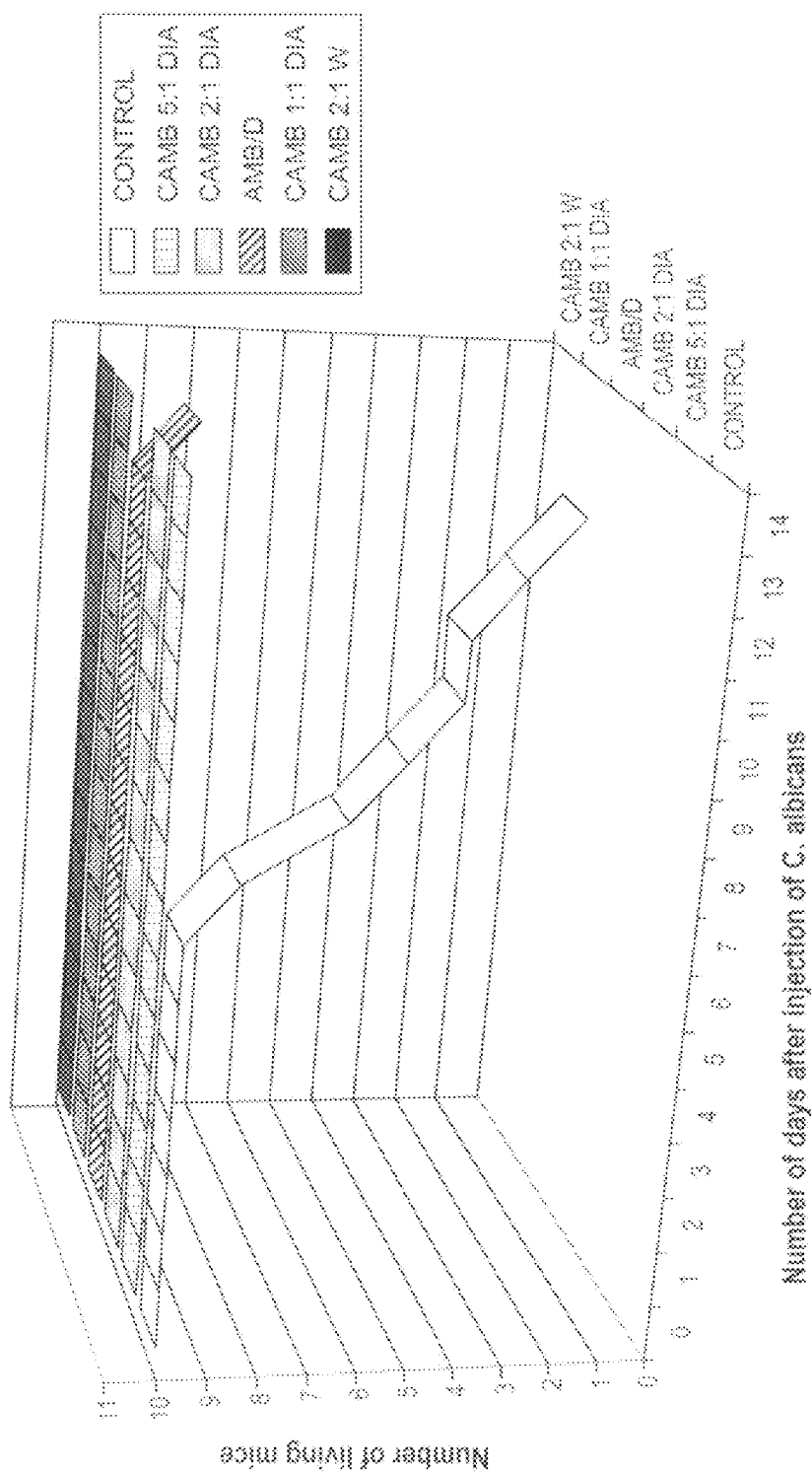
FIG. 14 is a graph of the survival data for the *C. albicans*-infected mice untreated or dosed daily for 14 days with AmB/deoxycholate (AmB/ID), or AmB-cochleates with a lipid to drug ratio of 5:1 (dialysis), 2:1 (dialysis), 1:1 (dialysis), or 2:1 (wash).

FIG. 14 is a graph of the survival data for the C. albicans-infected mice untreated or dosed daily for 14 days with AmB/deoxycholate (AmB/D), or AmB cochleates with a lipid to drug ratio of 5:1 (dialysis), 2:1 (dialysis), 1:1 (dialysis), or 2:1 (wash).

Figure 15:
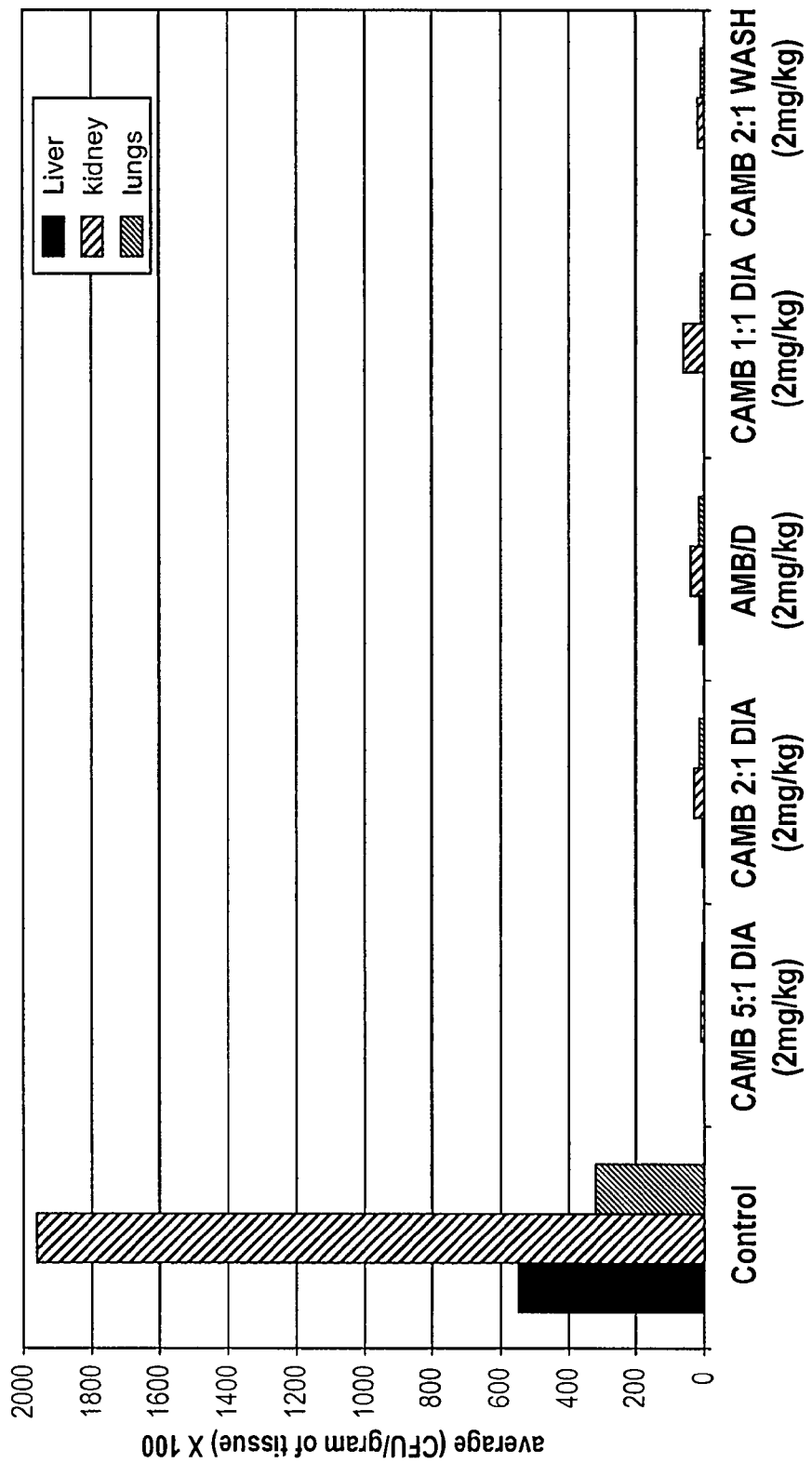
FIG. 15 is a chart of the average number of *C. albicans* cells/gram of tissue in the liver, kidney, and lungs of *C. albicans*-infected mice untreated (control), or dosed daily for 14 days with AmB/deoxycholate (AmB/D), or AmB-cochleates with lipid to drug ratios of 5:1 (dialysis), 2:1 (dialysis), 1:1 (dialysis), or 2:1 (washing).

FIG. 15 is a chart of the average number of C. albicans cells/gram of tissue in the liver, kidney, and lungs of C. albicans-infected mice untreated (control), or dosed daily for 14 days with AmB/deoxycholate (AmB/D), or AmB-cochleates with lipid to drug ratios of 5:1 (dialysis), 2:1 (dialysis), 1:1 (dialysis), or 2:1 (washing).

Seventy percent of control (untreated) animals died and showed high tissue burdens, while all four cochleate formulations were effective in preventing mortality and reducing fungal cell burdens in target organs (kidneys, lungs and liver). The 5:1 (dialysis) formulation appeared more effective than the others in clearing the liver completely. The 2:1 (washed) and 2:1 (dialysis) formulations had nearly the same efficacy. All formulations (excepted for 1:1 (dialysis) formulation) reduced the fungal cell burden as well as or better than the AmB/deoxycholate formulation. Overall, the data are consistent with effective oral delivery of AmB from cochleates.

Example 8

Efficacy of Cochleates in Cells

The relative efficacy of the compositions of Example 6 were studied in J774A.1 macrophages to compare the relative efficacy of the cochleate compositions against Candida albicans.

Macrophages were seeded into a 96-well plate and incubated overnight as described above. Following incubation, the macrophages were infected with C. Albicans at a ratio of 1:200 with respect to the macrophages. The AmB-cochleate formulations were then added at the concentrations of 0.1, 0.01 and 0.001 µg/ml. Twenty-four hours later, the cell cultures were lysed, samples plated onto agar plates, and counted the following day.

Figure 16:
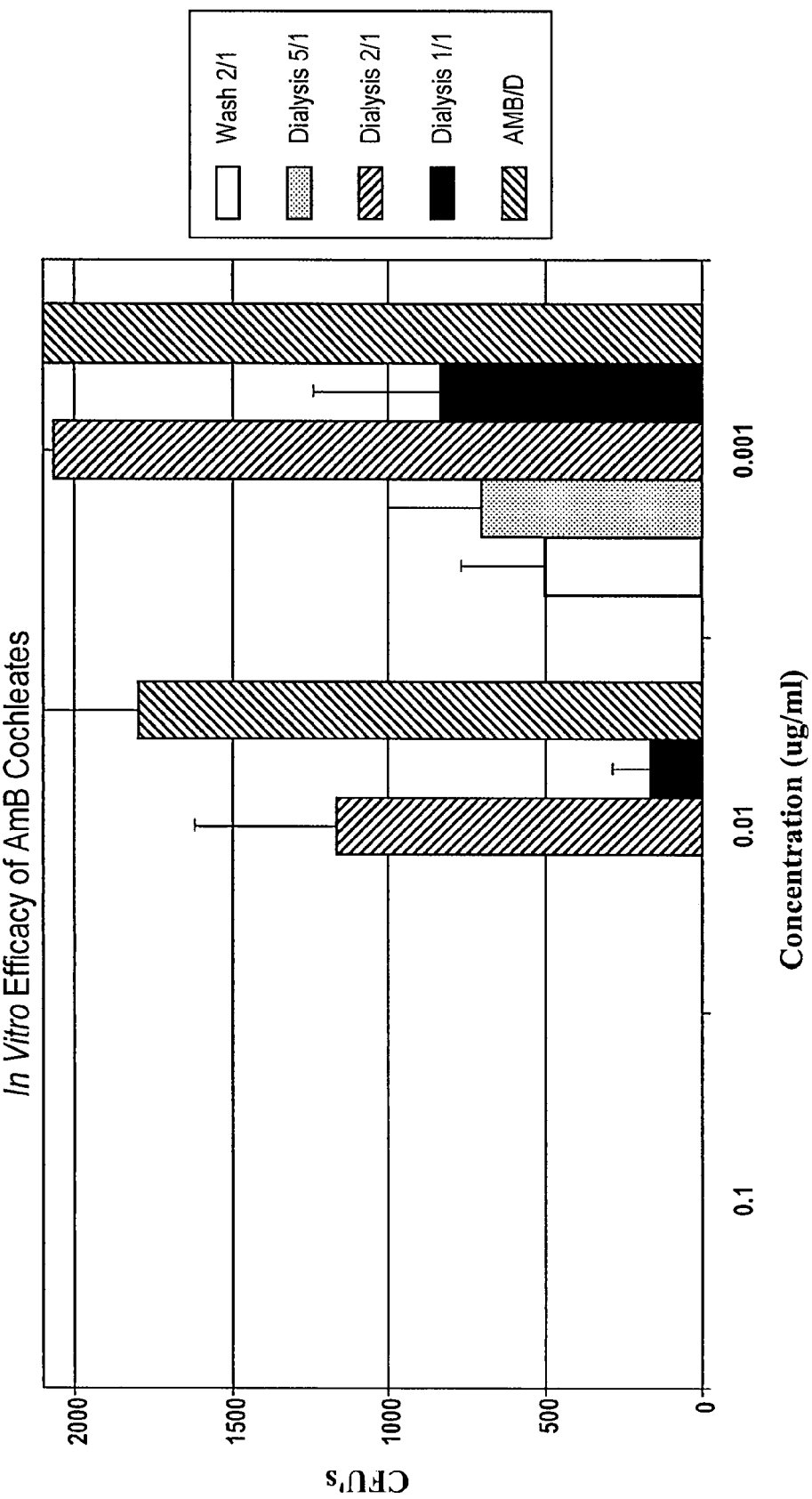
FIG. 16 is a graph depicting the number of colony forming units (CFUs) for *C. albicans*-infected macrophages dosed with varying concentrations (0.1, 0.01 and 0.001 μl/mg) of AmB-cochleate formulations having lipid to drug ratios of 5:1 (dialysis), 2:1 (dialysis), 1:1 (dialysis), and 2:1 (washing), or AmB/deoxycholate (AmB/D).

FIG. 16 is a graph depicting the number of colony forming units (CFUs) for C. albicans-infected macrophages dosed with varying concentrations (0.1, 0.01 and 0.001 µg/ml) of AmB-cochleate formulations having lipid to drug ratios of 5:1 (dialysis), 2:1 (dialysis), 1:1 (dialysis), and 2:1 (washing), or AmB/deoxycholate (AmB/D). The 2:1 (washing) and the 5:1 (dialysis) formulation were the most efficacious at killing the C. albicans at 0.001 µl/ml. In contrast, the AmB/deoxycholate CFU's were too numerous to count at this concentration.

Example 9

Amphotericin B Cochleates Prepared with DMSO and Lipid:AmB Ratio of 5:1 with and without Methylcellulose Amphotericin B cochleates were prepared using Soy PS and DMSO with Vitamin E, and a Lipid to AmB ratio of 5:1 as follows.

Preparation of Liposomes 20 ml of water was added to 200 mg of Soy-PS, vortexed for about 15 minutes to form a liposomal suspension, and filtered using a 0.45 µm filter. The suspension was sonicated for about 4 minutes and filtered again with a 0.22 µm filter.

Addition of Cargo Moiety and Antioxidant in Solvent 2 ml of DMSO solvent was added to 40 mg of Amphotericin B. To the AmB/DMSO mixture was added 2 mg of Vitamin E and the solution was vortexed for about 10 minutes. This solution was then added to the liposomal suspension by drop wise to addition while vortexing. The final mixture was vortexed for about 2 minutes.

Precipitation of Cochleates 2 ml of calcium (0.1 M) was added to the liposomal suspension at a rate of 10 µl/10 s while vortexing to form cochleates.

Solvent Removal/Washing

The mixture was vortexed for about 1-2 minutes, centrifuged for about 1 hour at 9000 rpm, and the supernatant was removed and replaced with fresh supernatant (water with 2 mM calcium). This washing step was repeated twice.

Inhibition of Aggregation 0.1%, 0.2%, 0.3%, 0.4%, or 0.5% (w/w) methylcellulose (MC) to inhibit aggregation and 0.2% (w/w) parabens to maintain sterility were added to the suspension, and it was lyophilized to form a powder.

Figure 58:
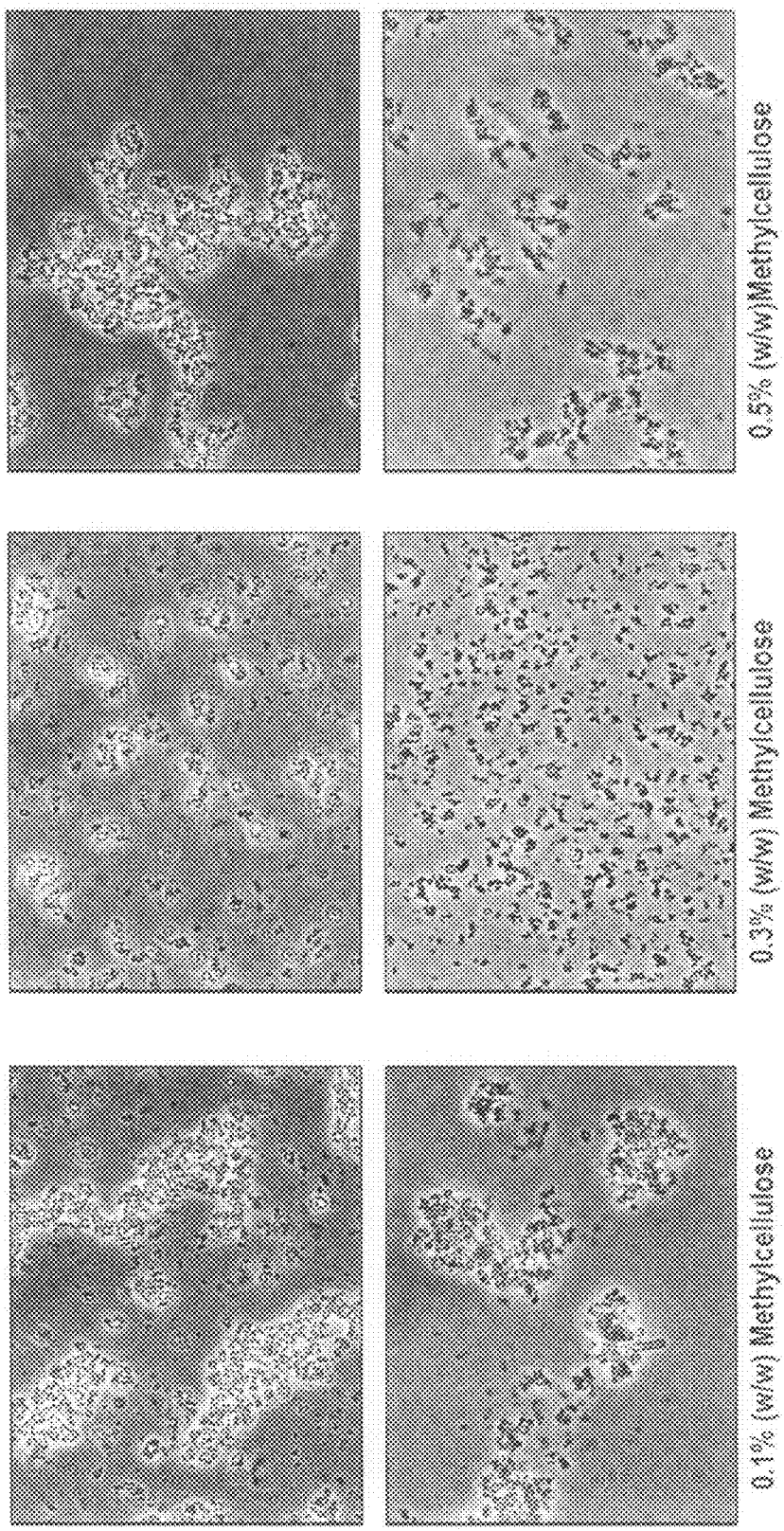
FIG. 58 is a series of images depicting Amphotericin B cochleates with a 5:1 lipid:drug ratio containing 0.2% parabens and varying amounts of methylcellulose.
Figure 59:
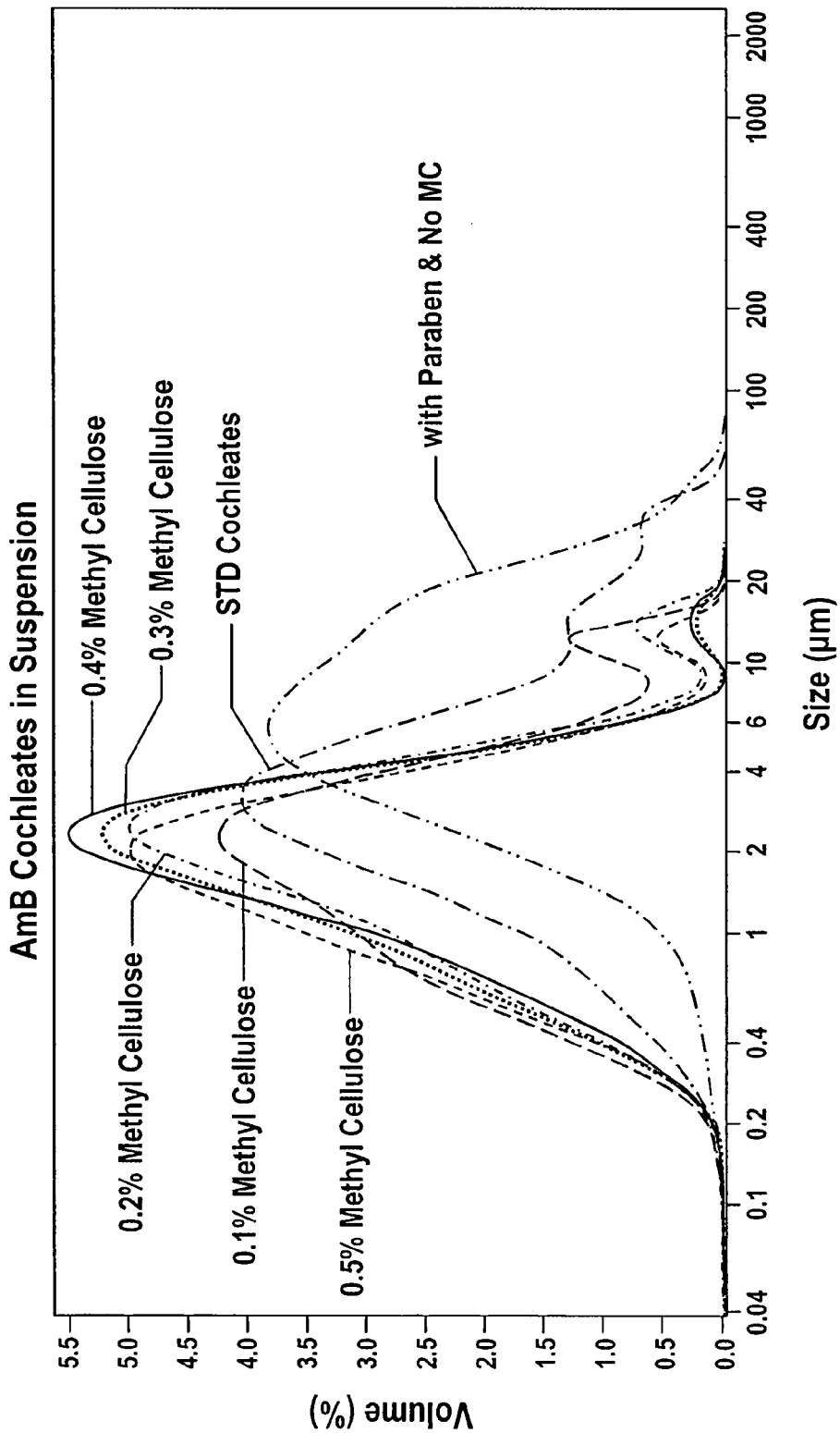
FIG. 59 is a graph depicting particle size distribution of Amphotericin B cochleates with a 5:1 lipid:drug ratio containing varying amounts of methylcellulose or 0.2% parabens.
Figure 60:
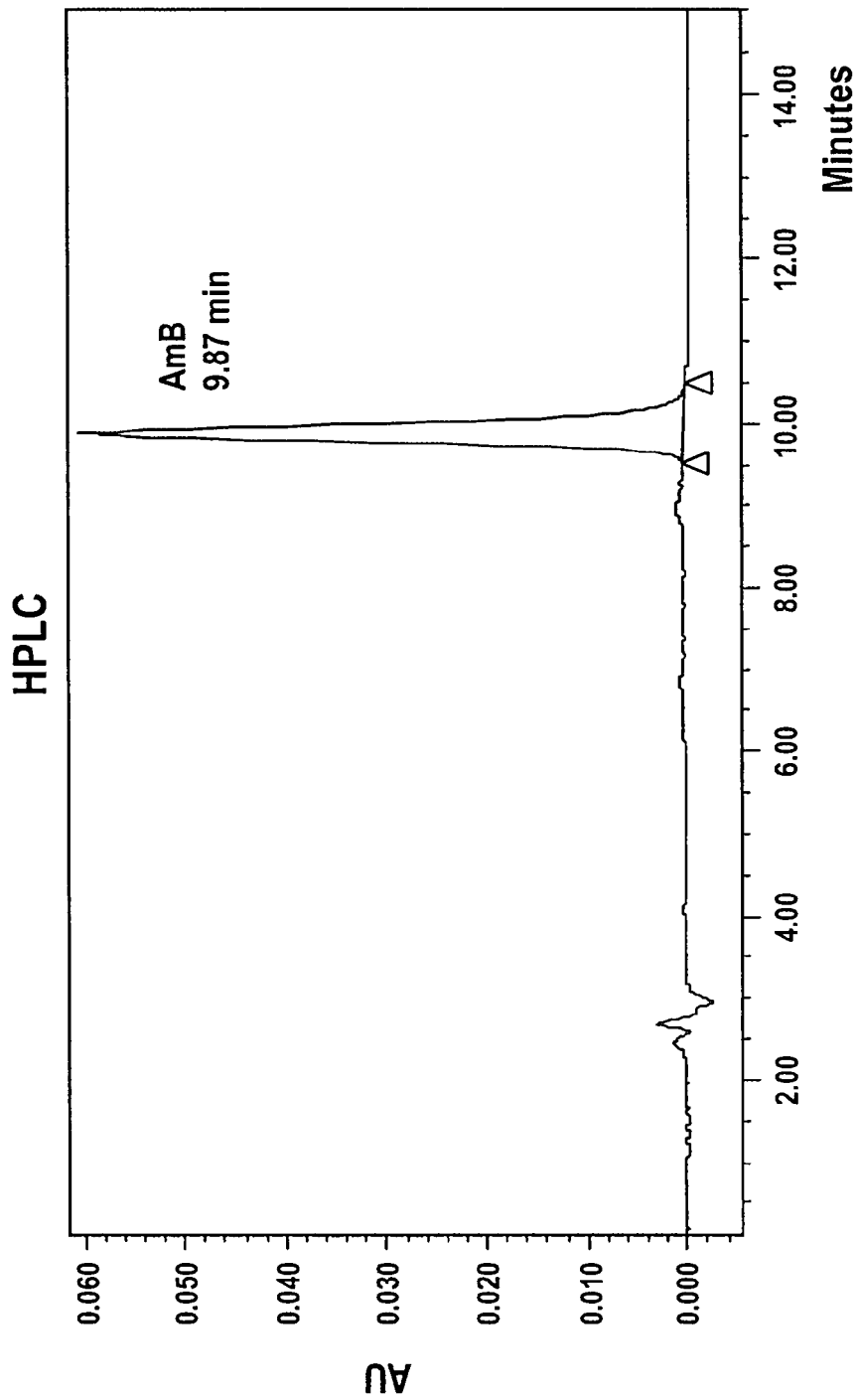
FIG. 60 is an HPLC spectrum depicting the contents of opened Amphotericin B cochleates formed using an exemplary method of the invention. Only Amphotericin B is present in the cochleate.

Images of cochleates containing 0.2%, 0.3% and 0.5% methylcellulose are given in FIG. 58. Particle size distributions in FIG. 59 show that the addition of methylcellulose decreases aggregation, and that the addition of paraben slightly increases aggregation. FIG. 60 is an HPLC analysis of the cochleate showing that amphotericin B is the only compound within the cochleate structure.

Example 10

Efficacy Studies in Mice

AmB/deoxycholate and 5:1 AmB cochleates (CAMB) formulated as described in Example 9 with and without 0.3% methylcellulose (MC) were administered to mice to study the efficacy of the formulations to protect mice from a lethal dose of *Candida albicans*, and to clear the organs of *C. albicans* in the surviving mice.

Six groups of 10 mice were studied. The mice were administered $5\times10^5$ cells *C. albicans* intravenously through the tail vein. Starting 24 hours post-infection, the following compositions were administered to each group once daily for 14 days in the dosage indicated, except for the control group which remained untreated.
 a. Control
 b. AmB/deoxycholate 2 mg/kg ip
 c. 5:1 CAMB (suspension) with 0.3% MC, 1 mg/kg AmB oral dosing
 d. 5:1 Lyophilized CAMB with 0.3% MC, 1 mg/kg AmB oral dosing
 e. 5:1 CAMB (suspension), 1 mg/kg AmB oral dosing
 f. 5:1 Lyophilized CAMB, 1 mg/kg AmB oral dosing Appearance and behavior was monitored each day of the study. On day 15, mice were sacrificed and tissue burden of *C. Albicans* was determined in kidney, liver and lungs for each animal. Organs were obtained and weighed, homogenized, diluted in buffer, and aliquots were plated onto plates; colony counts of fungus were taken several days later.

Figure 17:
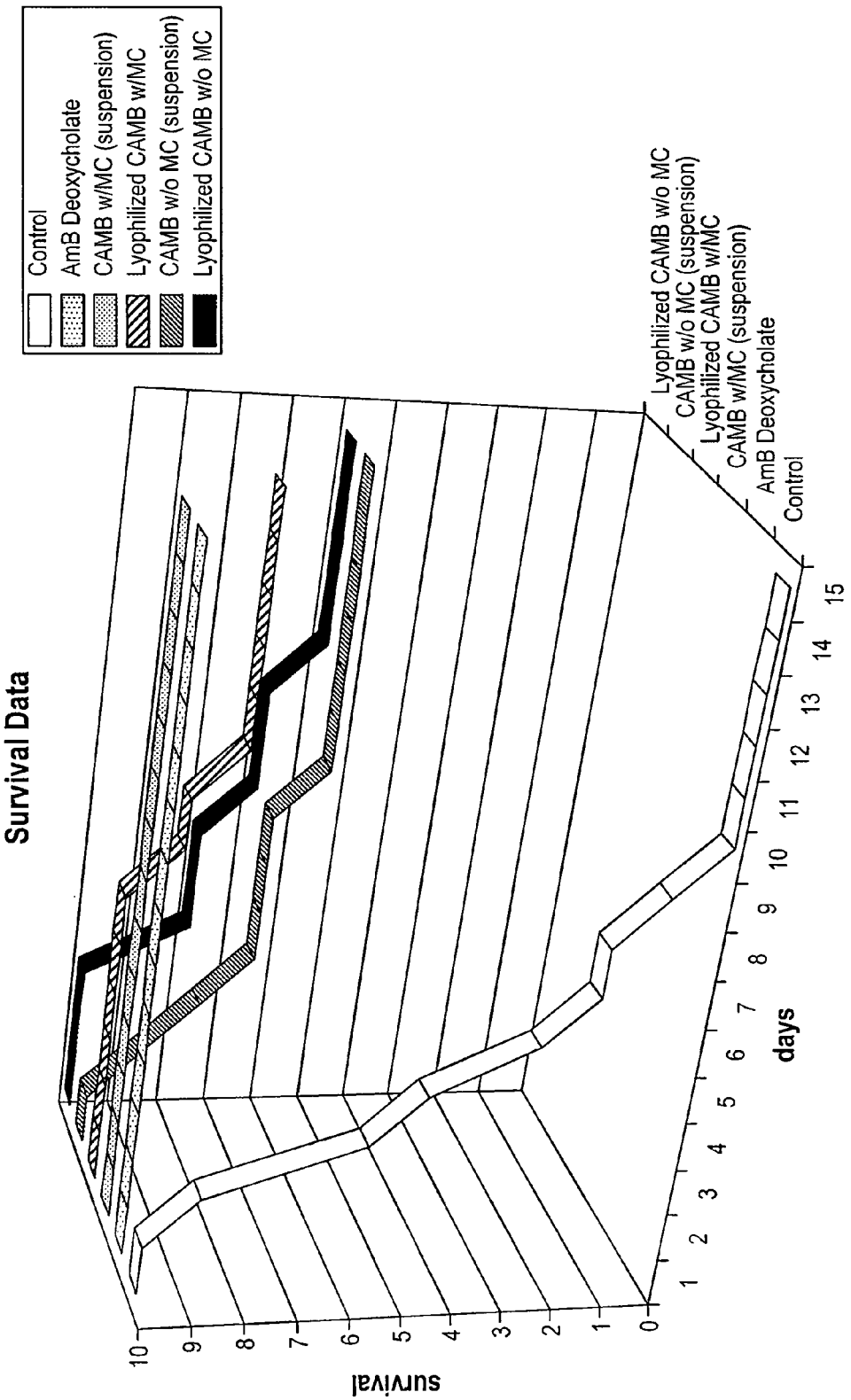
FIG. 17 is a graph of the survival data for *C. albicans*-infected mice untreated (control), or dosed daily for 14 days with AmB/deoxycholate or AmB-cochleates (CAMB) in suspension or lyophilized and formulated with or without methylcellulose (MC).

FIG. 17 is a graph of the survival data for the *C. albicans*-infected mice untreated or dosed daily for 14 days with AmB/deoxycholate (AmB/D), or AmB cochleates (CAMB) in suspension or lyophilized and formulated with or without methylcellulose (MC).

Figure 18:
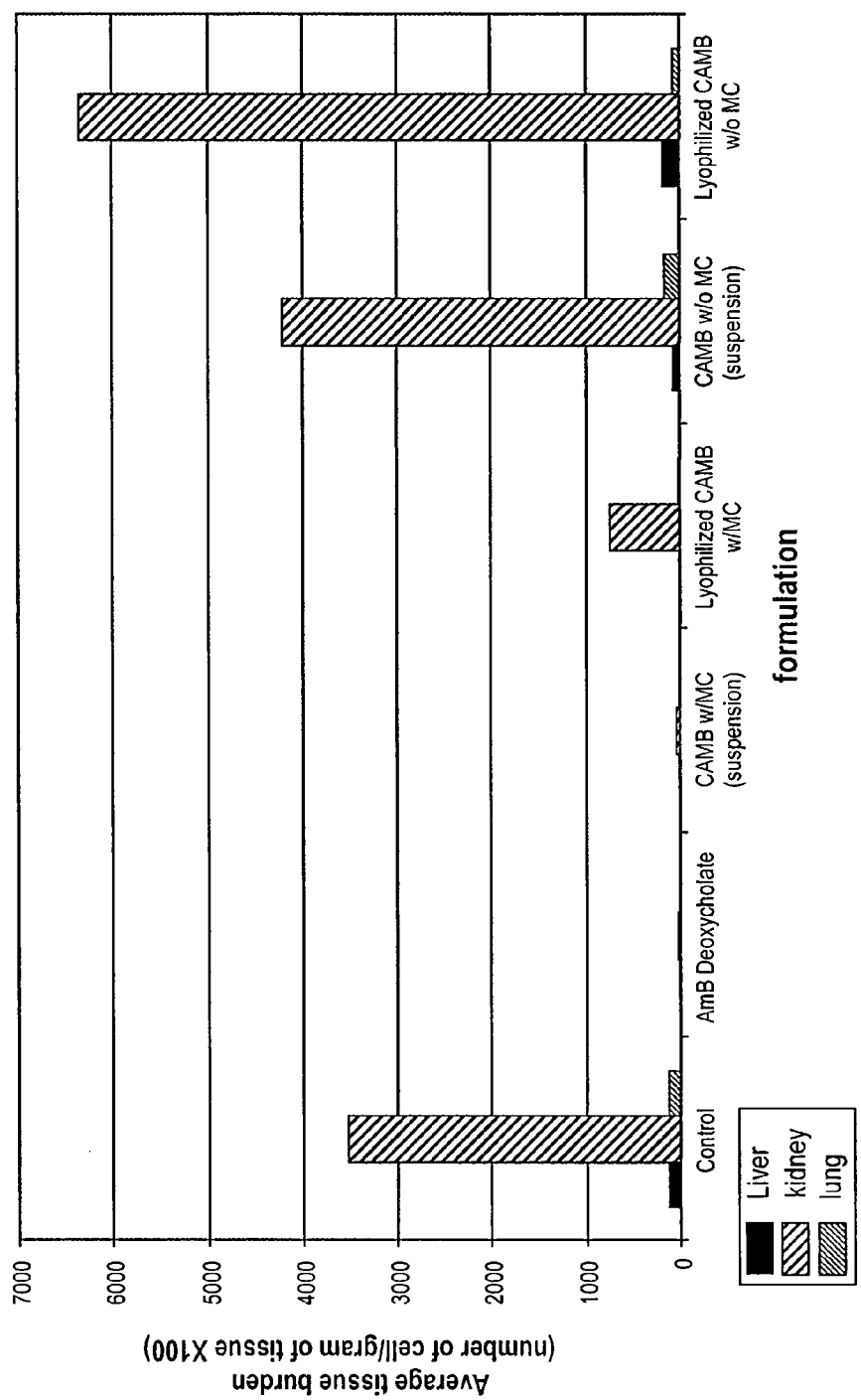
FIG. 18 is a chart of the average number of *C. albicans* cells/gram of tissue in the liver, kidney, and lungs of *C. albicans*-infected mice untreated and dosed daily for 14 days with AmB/deoxycholate or AmB-cochleates (CAMB) in suspension or lyophilized and formulated with or without methylcellulose (MC).

FIG. 18 is a chart of the average number of *C. albicans* cells/gram of tissue in the liver, kidney, and lungs of *C. albicans*-infected mice untreated (control), or dosed daily for 14 days with AmB/deoxycholate, or AmB-cochleates (CAMB) in suspension or lyophilized and formulated with or without methylcellulose (MC).

One hundred percent of control (untreated) animals died by day 10 and showed high tissue burdens. AmB/deoxycholate at 2 mg/kg resulted in 100% survival and completely cleared *Candida* from the liver and lungs and decreased the tissue burden in the kidney by 2-3 log units. Forty percent of the mice treated with CAMB without methylcellulose (both in suspension and lyophilized) died and both groups also showed substantial tissue burdens in target organs. However, CAMB with methylcellulose in suspension and lyophilized CAMB with methylcellulose afforded 100% and 80% survival, respectively, and showed several log order reductions in tissue burden relative to the other CAMB formulation. The antifungal properties of CAMB with methylcellulose in suspension at 1 mg/kg administered PO mimicked the behavior of AmB/deoxycholate at 2 mg/kg administered IP. Overall, cochleates with methylcellulose showed stronger antifungal properties than cochleates without methylcellulose.

Example 11

Efficacy Studies in Cells

The relative efficacy of the compositions of Example 9 were studied in J774A.1 macrophages to compare the relative efficacy of the cochleate compositions (with and without methylcellulose) against *Candida albicans*.

Macrophages were seeded into a 96-well plate and incubated overnight as described above. Following incubation, the macrophages were infected with *C. albicans* at a ratio of 1:200 with respect to the macrophages. The AmB-cochleates were then added at the concentrations of 5, 1, 0.1, 0.01 and 0.001 µg/ml. Twenty-four hours later the cell cultures were lysed, samples were plated onto agar plates, and colonies were counted the following day.

Figure 61:
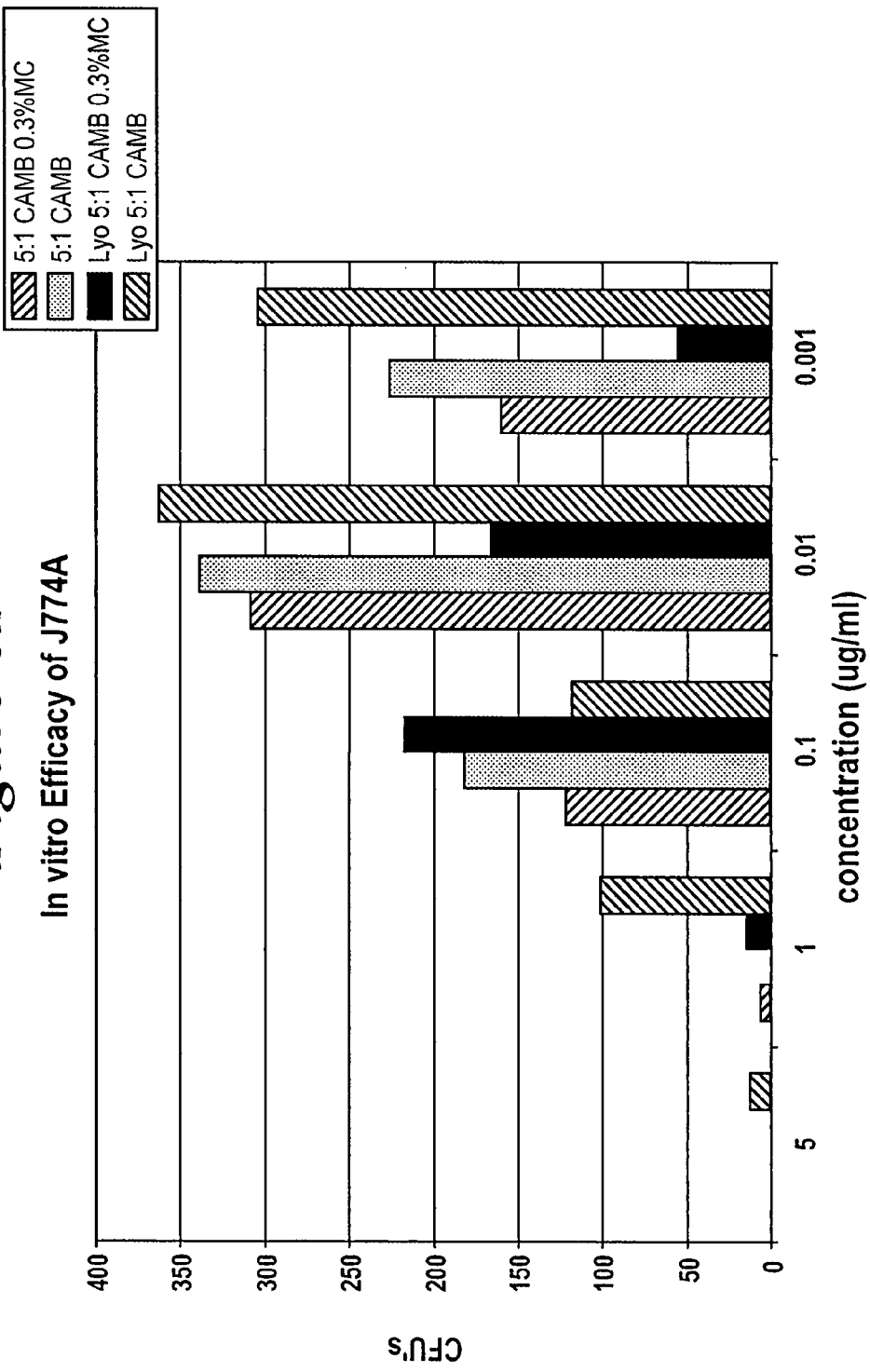
FIG. 61 is a graph depicting the number of colony forming units (CFUs) for *C. albicans*-infected macrophages dosed with varying concentrations (5, 1, 0.1, 0.01 and 0.001 µl/mg) of AmB-cochleate formulations having lipid to drug ratios of 5:1 with and without 0.3% methylcellulose in suspension and lyophilized to form a powder.

FIG. 61 is a graph of the number of colony forming units (CFU) for the *C. albicans*-infected macrophages dosed with AmB-cochleates in suspension and lyophilized with lipid to drug ratio 5:1, with and without methylcellulose. All cochleate formulations were efficacious at killing *C. albicans*.

Example 12

Scale Up

Figure 62:
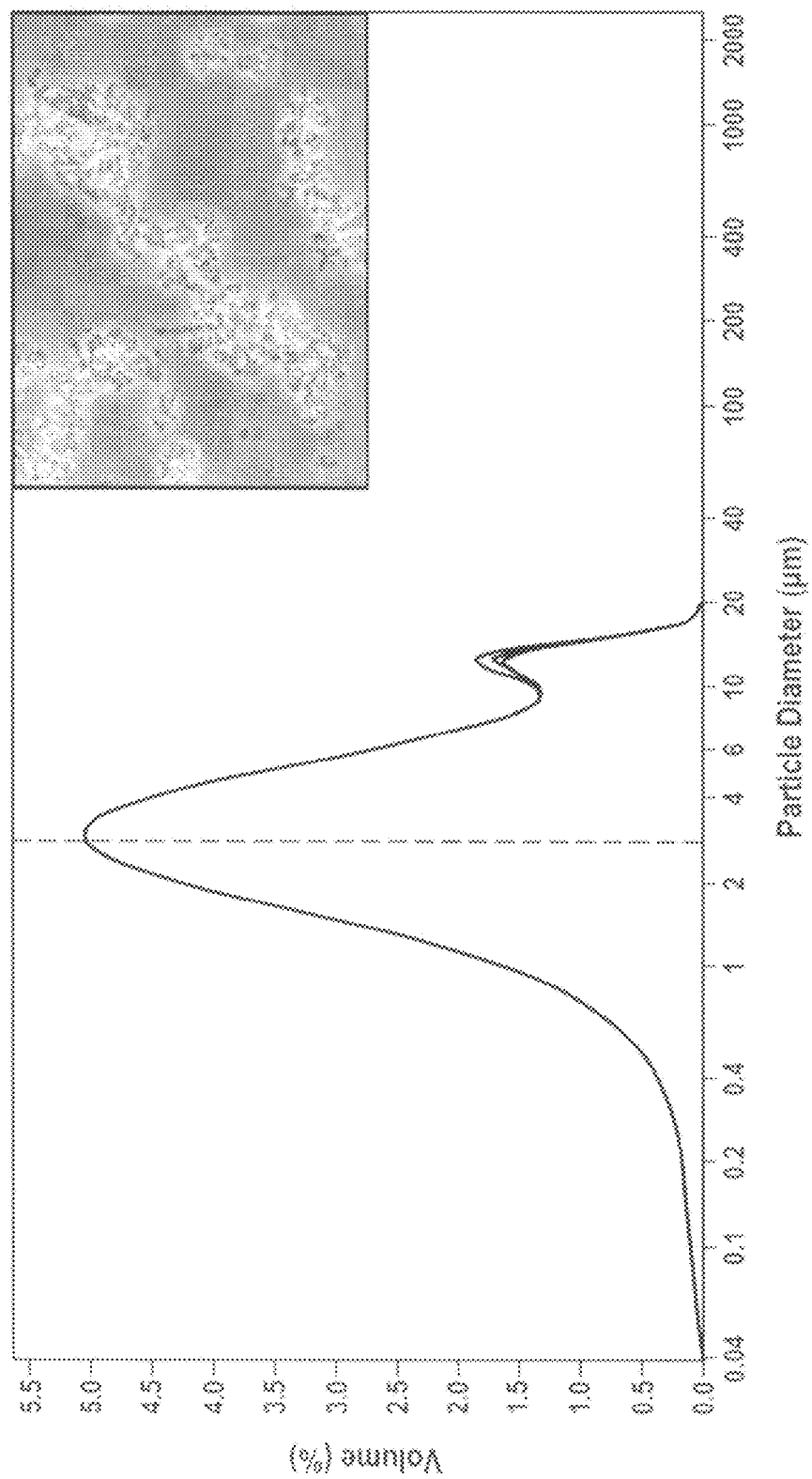
FIG. 62 is a graph depicting the particle size distribution of amphotericin B cochleates formulated in a large batch (>5 L) with an inset of the image of the amphotericin B cochleates.
Figure 63:
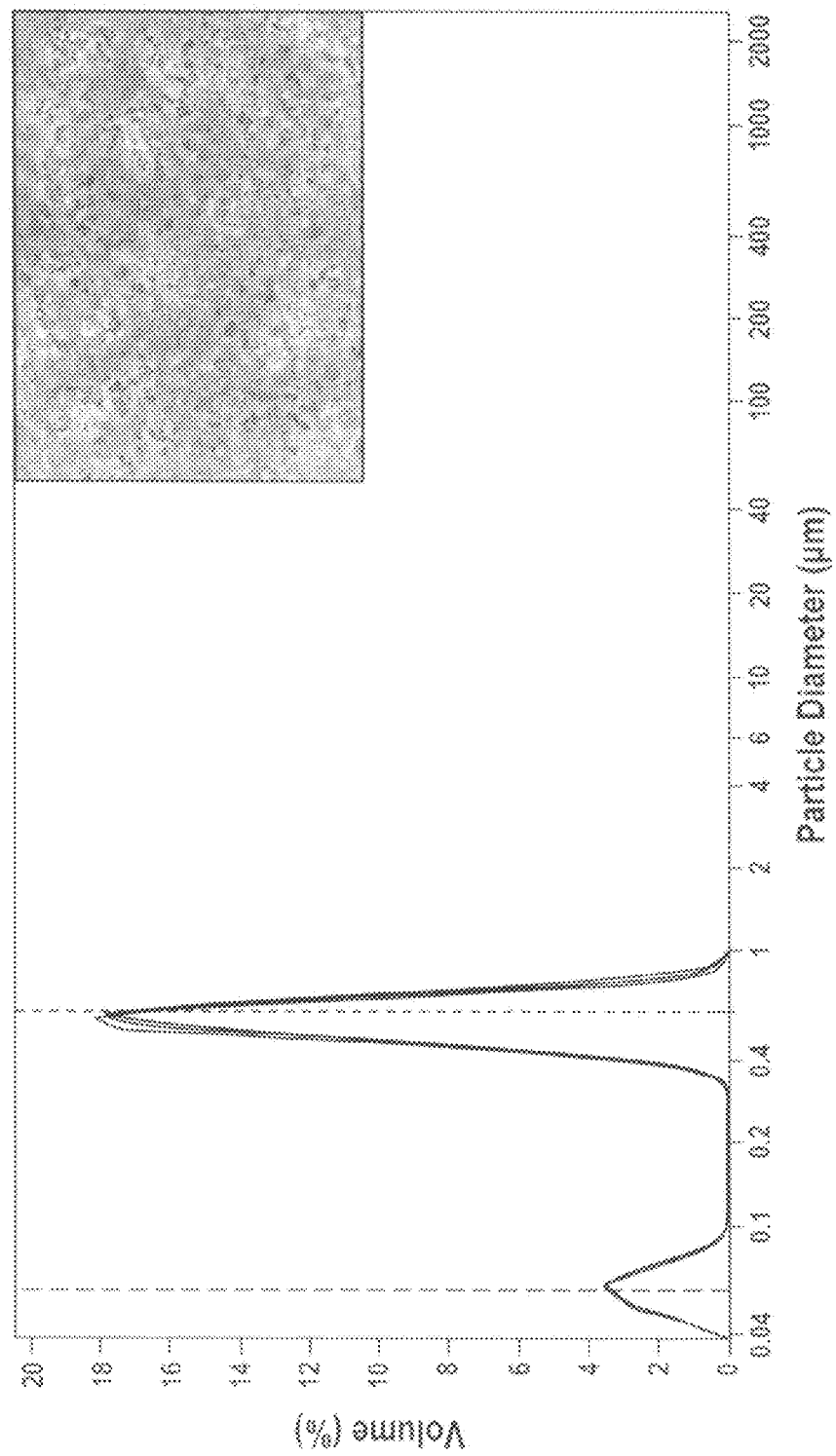
FIG. 63 is a graph depicting the particle size distribution of amphotericin B cochleates formulated in a large batch (>5 L) with additional rabbit serum albumin and passed through a homogenizer 2 times. The inset is an image of the amphotericin B cochleates after homogenization.
Figure 64:
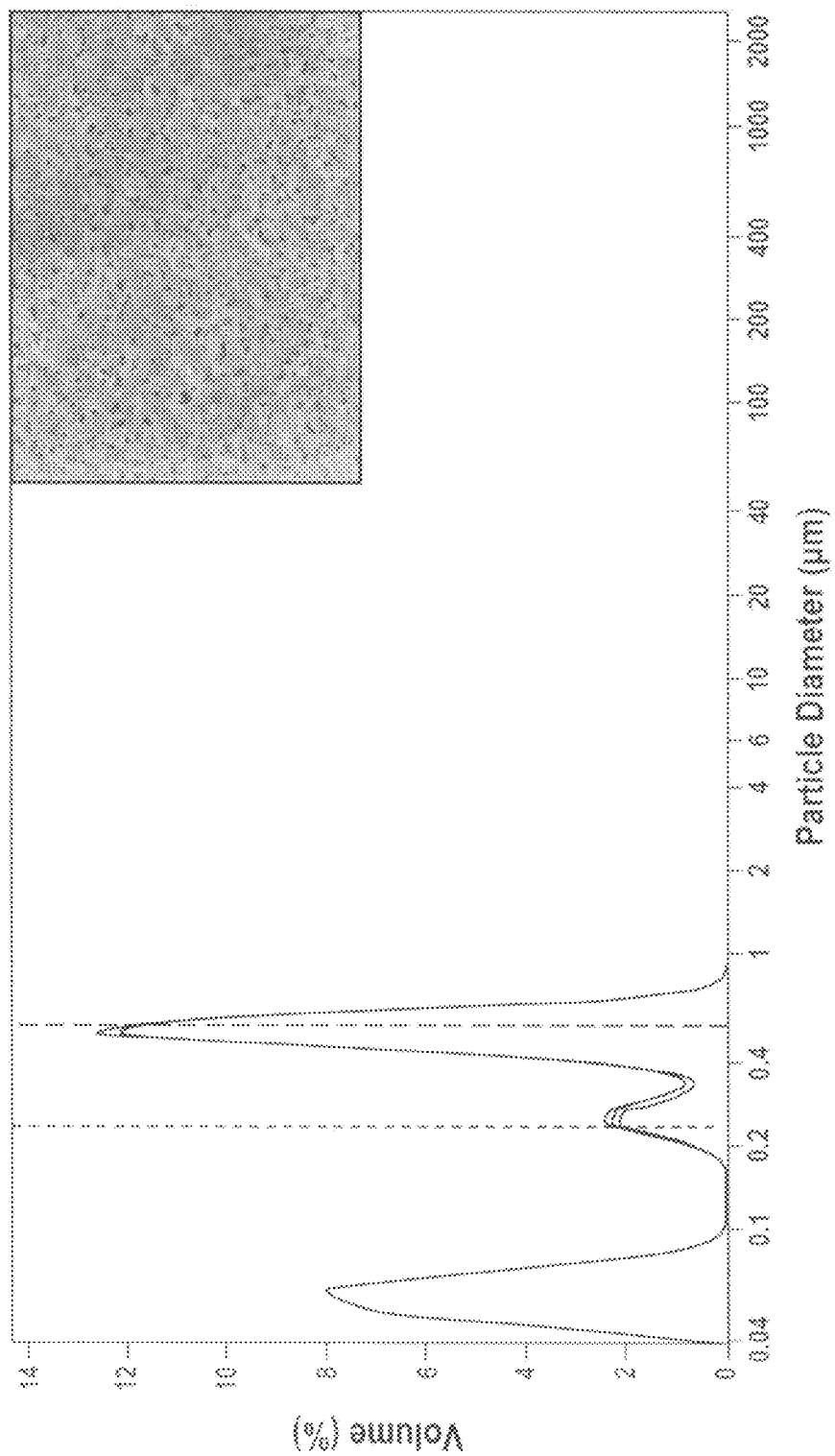
FIG. 64 is a graph depicting the particle size distribution of amphotericin B cochleates formulated in a large batch (>5 L) with additional rabbit serum albumin and passed through a homogenizer 7 times. The inset is an image of the amphotericin B cochleates after homogenization.

Amphotericin B cochleate preparation was scaled up to 5 liters using Soy PS and DMSO with Vitamin E, and a Lipid to AmB ratio of 5:1 as follows.
Preparation of Liposomes
 5.4 L of water was added to 50 g of Soy-PS, vortexed for about 15 minutes to form a liposomal suspension, and filtered using a 10 µm filter.
Addition of Cargo Moiety and Antioxidant in Solvent
 500 ml of DMSO solvent was added to 10 g of Amphotericin B. To the AmB/DMSO mixture was added 60 mg of Vitamin E and the solution was vortexed for about 10 minutes. This solution was then added to the liposomal suspension by drop wise addition using a separatory funnel while vortexing. The final mixture was vortexed for about 2 minutes.
Precipitation of Cochleates
 100 ml of calcium (0.5 M) was added to the liposomal suspension at a rate of 10 µl/10 s while vortexing to form cochleates.
Solvent Removal/Washing
 The mixture was vortexed for about 1-2 minutes, centrifuged for about 1 hour at 9000 rpm, and the supernatant was removed and replaced with fresh supernatant (water with 2 mM calcium). This washing step was repeated twice.
Optional Inhibition of Aggregation
 0.3% (w/w) methylcellulose (MC) to inhibit aggregation and 0.2% (w/w) parabens to maintain sterility were added to the suspension, and it was lyophilized to form a powder. Subsequently, the cochleates were treated with rabbit serum albumin and forced multiple times through a high pressure homogenizer such as the Avestin EmulsiFex-C5. Homogenization pressure was maintained around 15K to 20K psi. Particle size distributions of cochleates before treatment with albumin, after two passes through a homogenizer and after seven passes through a homogenizer are shown in FIGS. 62, 63 and 64, respectively.

Example 13

Geldanamycin Cochleates

Geldanamycin (GA)-cochleates were prepared as described in Example 1. The cochleates were observed macroscopically to have successfully encochleated GA, and also included crystals, possibly including unencochleated GA. When cochleates were centrifuged, about one third of the GA was present in the supernatant. Overall, the GA was successfully encochleated.

Example 14

Tyrphostin Cochleates

Tyrphostin AG-825 (TY)-cochleates were prepared using the solvent drip method described in Example 1. Good morphology of TY-cochleates was observed, in that it appeared that TY was successfully encochleated.

HPLC Analysis and Stability of TY-Cochleate Formulation

HPLC was used to study the stability of the TY in the cochleates, by measuring the concentration of TY in TY-cochleates as compared to free, i.e., unencochleated TY in solution.

Figure 19:
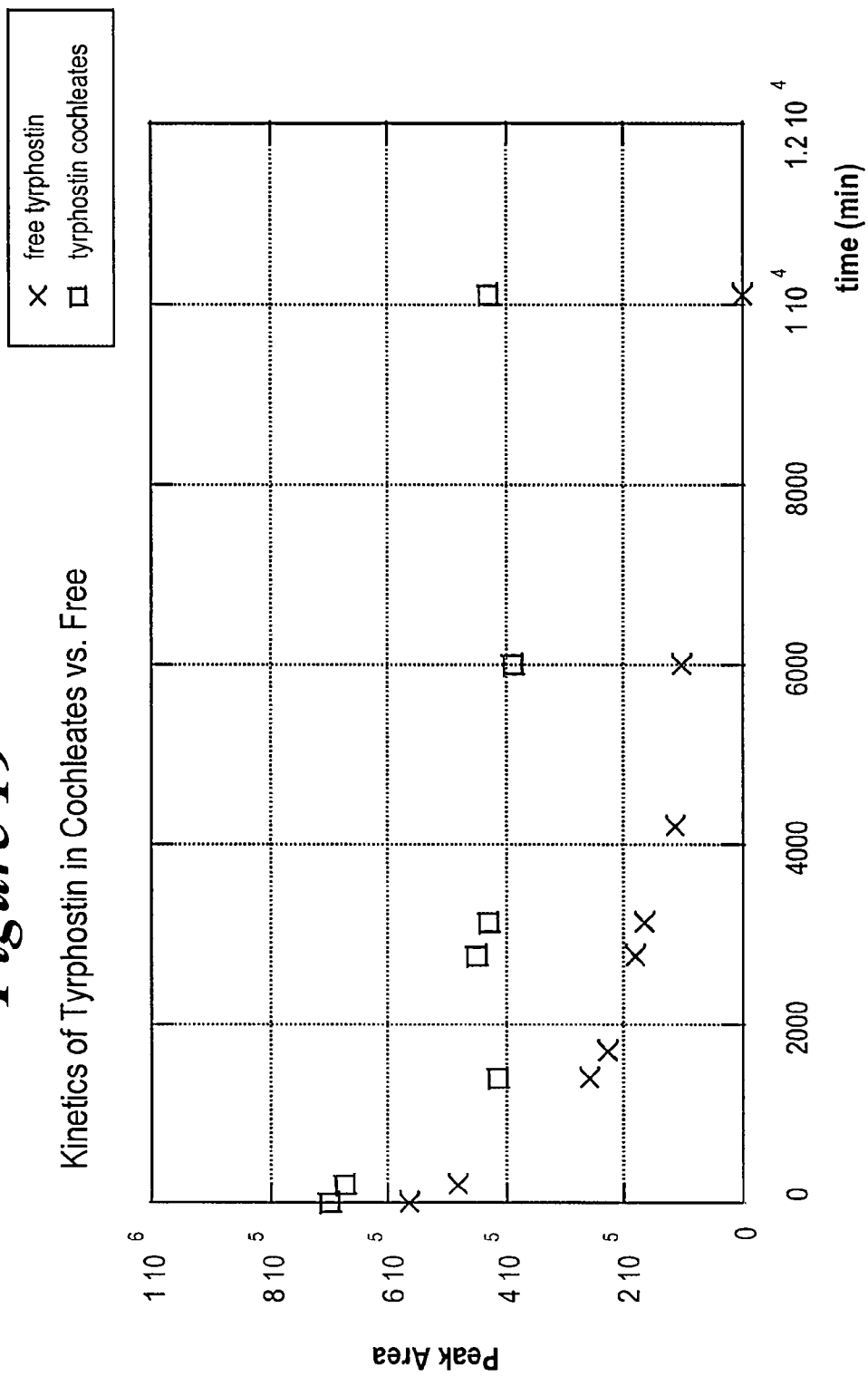
FIG. 19 is a graph of the concentration of TY-cochleate preparations versus free TY over time.

FIG. 19 is a graph of the concentration of TY-cochleate preparations versus free TY over time. As can the seen in FIG. 19, the free TY concentration decreased to zero over time. In contrast, the TY concentration initially dropped for the TY-cochleates (possibly due to the degradation of free TY in the cochleate formulation), and stabilized thereafter.

Figure 20:
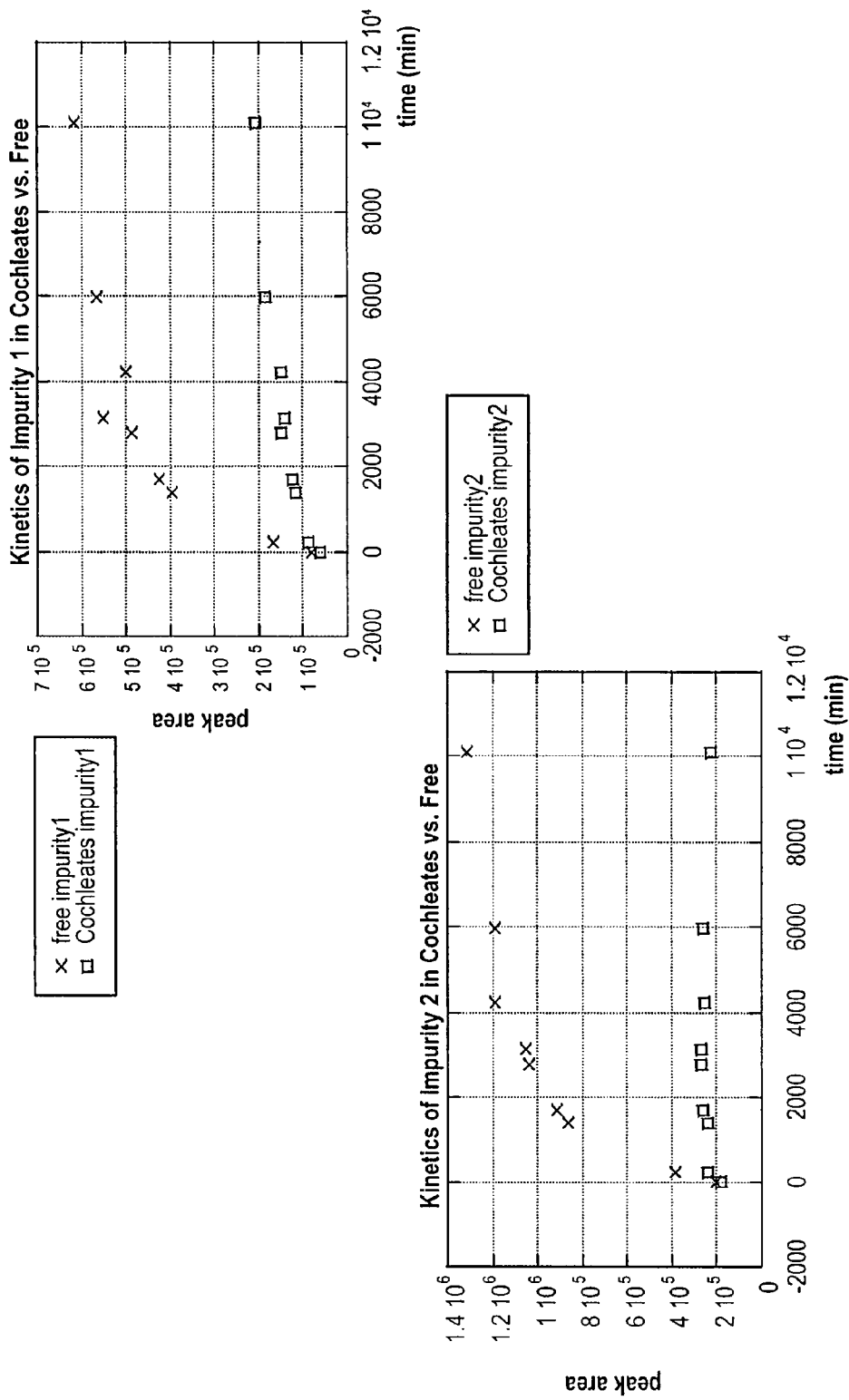
FIG. 20 is two graphs of the concentration of each impurity over time for both the free TY and TY-cochleates studied in FIG. 21.

TY degrades into two products (identified as impurity 1 and impurity 2 in FIG. 20). FIG. 20 is two graphs of the concentration of each impurity over time for both the free TY and TY-cochleates studied in FIG. 19. FIG. 20 confirms that the free TY degraded over time, whereas, after an initial degradation was observed, the concentration of degradation products remained fairly stable for the TY-cochleates.

Biological Evaluation of Tyrphostin AG-825 Cochleates

Figure 21:
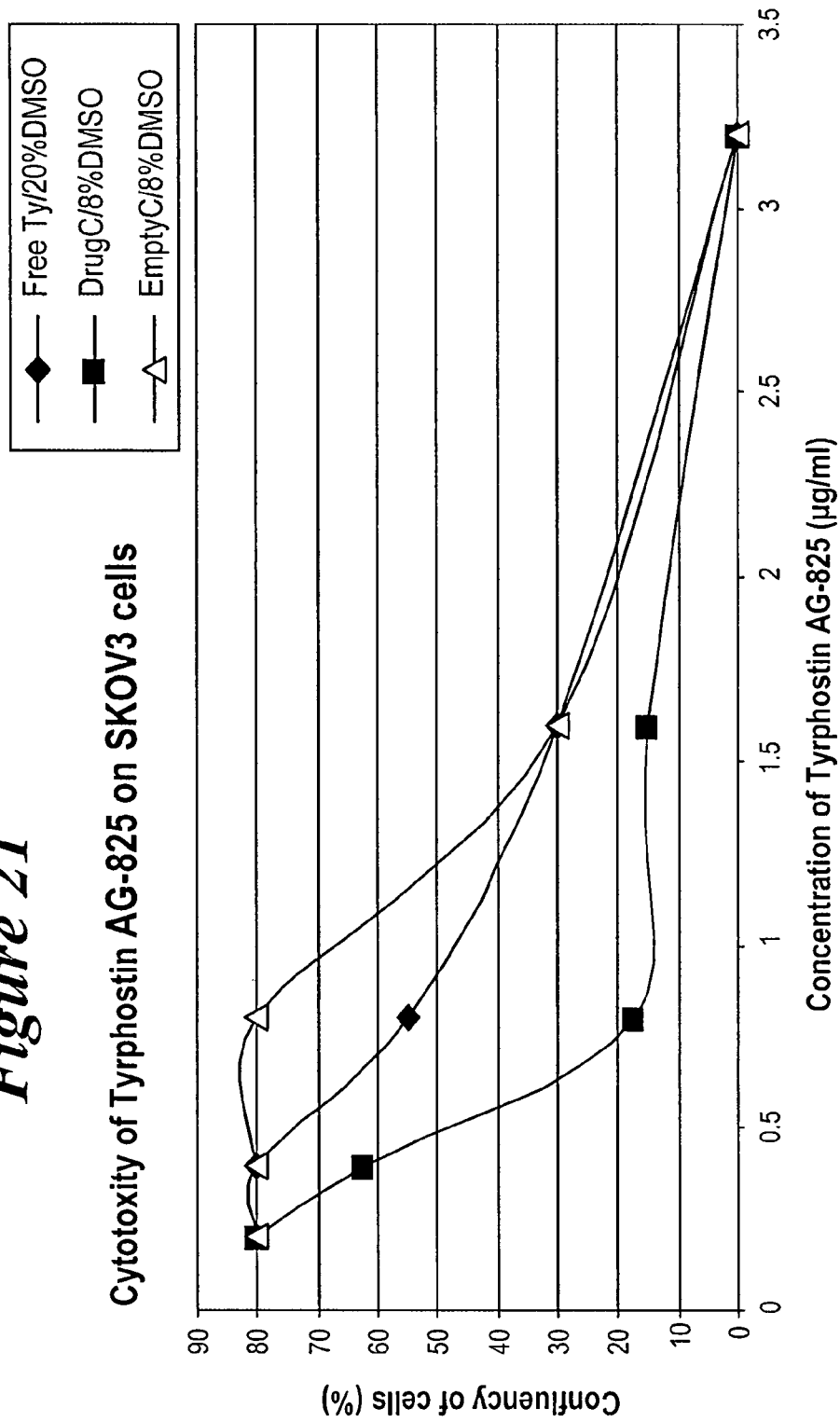
FIG. 21 is a graph comparing the cytotoxicity of TY-cochleates in a SKOV3 cell line.

Cytotoxicity of TY-cochleates was studied in a SKOV3 cell line (FIG. 21). The TY-cochleates showed slightly higher cytotoxicity against the cancer cell line than that from free TY. The data for empty (drug free) cochleates also is shown.

Results

Tyrphostin AG-825 was successfully formulated into cochleates using the method of the present invention. Stability tests demonstrated that TY-cochleates have a superior stability as compared to free TY in solution, and biological analysis of TY-cochleates indicated that it delivered similar cytotoxic effects on SKOV3 cell line to that of its free form in solution.

Porphyrin-cochleates also have been successfully made with ethanol, DMG and THF solvents.

Example 15

Porphyrin Cochleates

Porphyrin cochleates were prepared with Zinc Tetra-Phenyl Porphyrin (ZnTPP) and DMSO as described in Example 1, adjusted for a lipid to ZnTPP ratio of 20,000:1 w/w.

The particle size and fluorescence of: plain liposomes; liposomes with ZnTPP; and cochleates with ZnTPP, were evaluated and the following results were obtained.

TABLE 5

Particle Size and Fluorescence

| | Particle Size Mean (nm) | Particle Size StD (nm) | Fluorescence Max (nm) | Intensity (a.u.) |
|---|---|---|---|---|
| Liposomes | 300.1 | 132.4 | | |
| Liposomes + ZnTPP | 280.1 | 122.9 | 595.5 | 45338 |
| Cochleates + ZnTpp | <10 µm | | 596 | 43589 |

Figure 22:
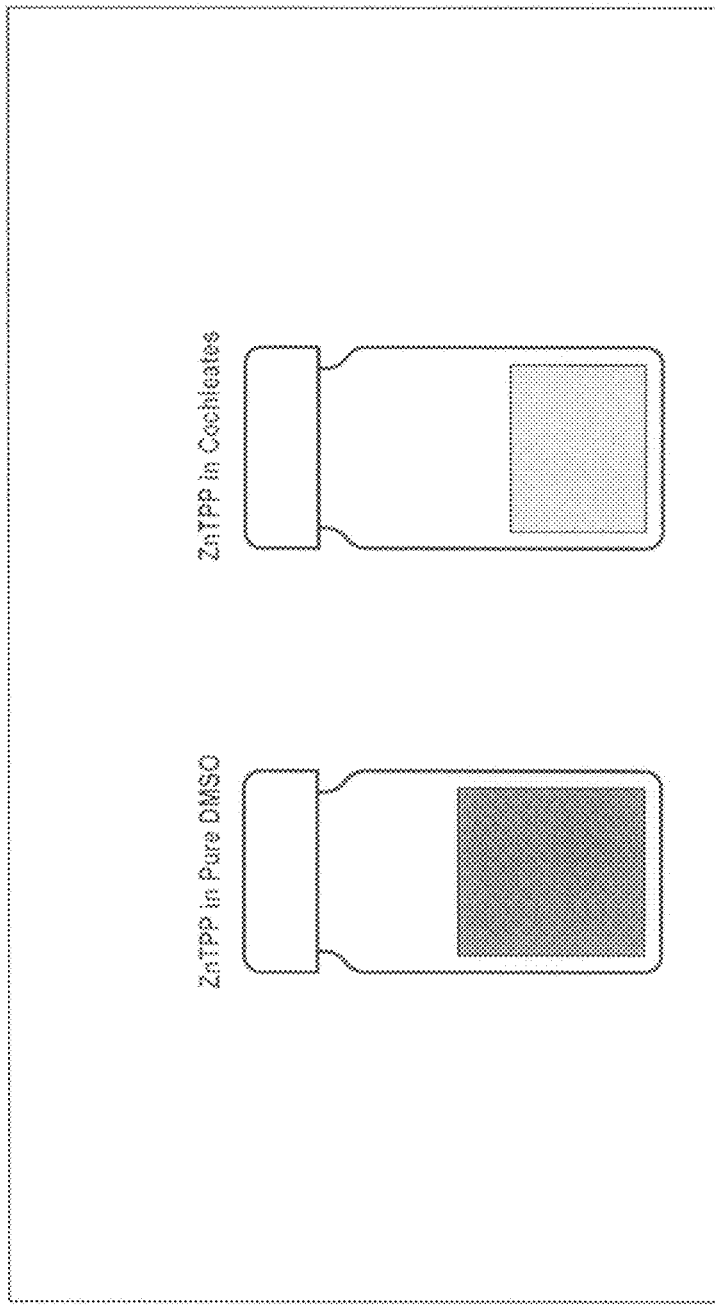
FIG. 22 is an image of ZnTPP in solution (100% DMSO), and ZnTPP-cochleates. The ZnTPP in solution was dark purple, and the cochleate formulation was only slightly colored (pink), indicating that the ZnTPP was successfully incorporated into the cochleates, which are white/yellowish.

FIG. 22 is an image of ZnTPP in solution (100% DMSO), and the ZnTPP-cochleates. The ZnTPP in solution was dark purple, and the cochleate formulation was only slightly colored (pink), indicating that the ZnTPP was successfully incorporated into the cochleates, which are white.

Figure 23:
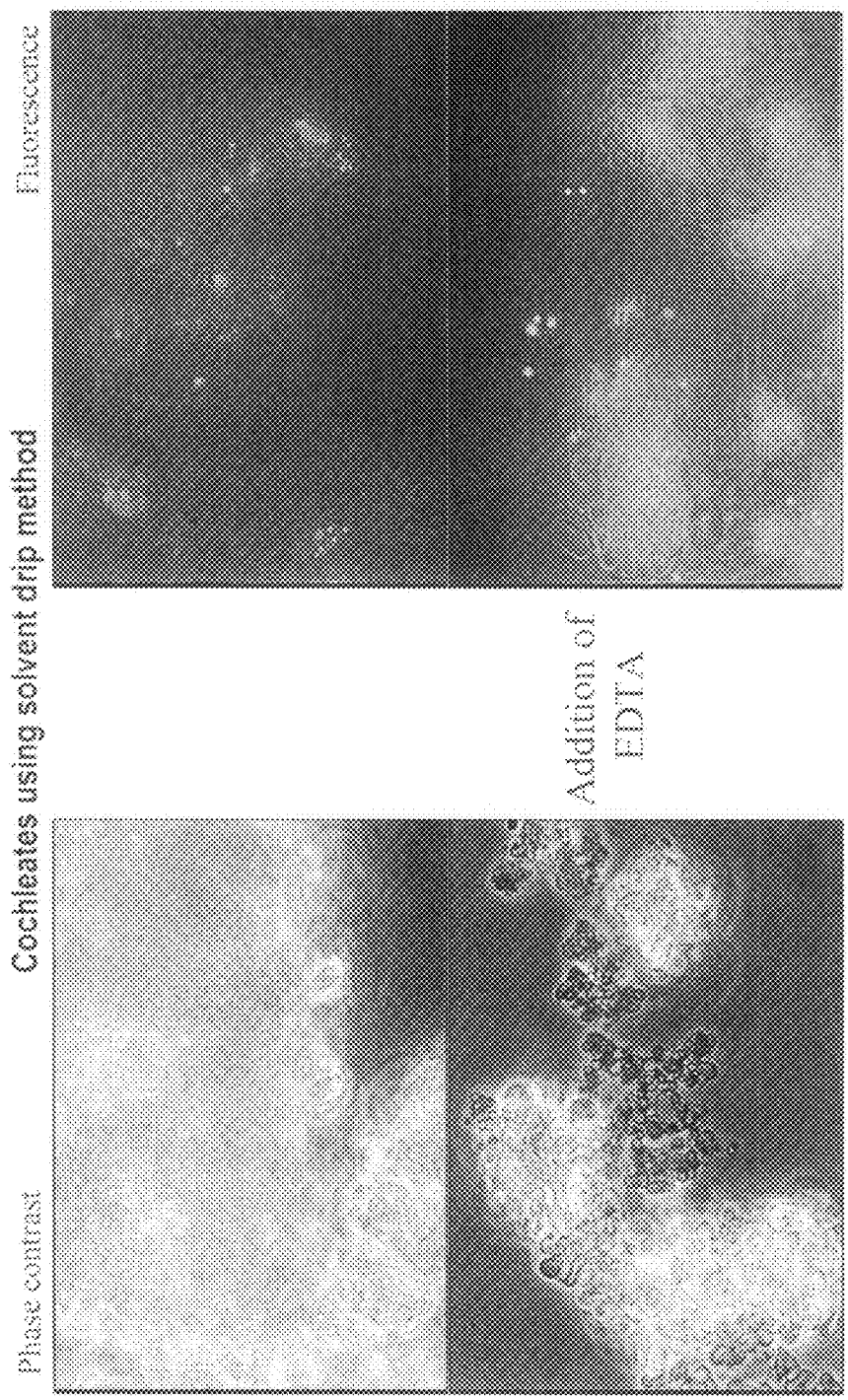
FIG. 23 is a series of phase contrast images (left panels) and fluorescence images (right panels), of the ZnTPP-cochleates (top panels) and ZnTPP-liposomes (bottom panels) formed. These images indicate that the ZnTPP was successfully associated with the liposomes and successfully encochleated.

FIG. 23 is a series of phase contrast images (left panels) and fluorescence images (right panels), of the ZnTPP-cochleates (top panels) and ZnTPP-liposomes (bottom panels) formed. These images indicate that the ZnTPP was successfully associated with the liposomes and successfully encochleated.

Comparison to Cochleates Formed without Solvent

Figure 24:
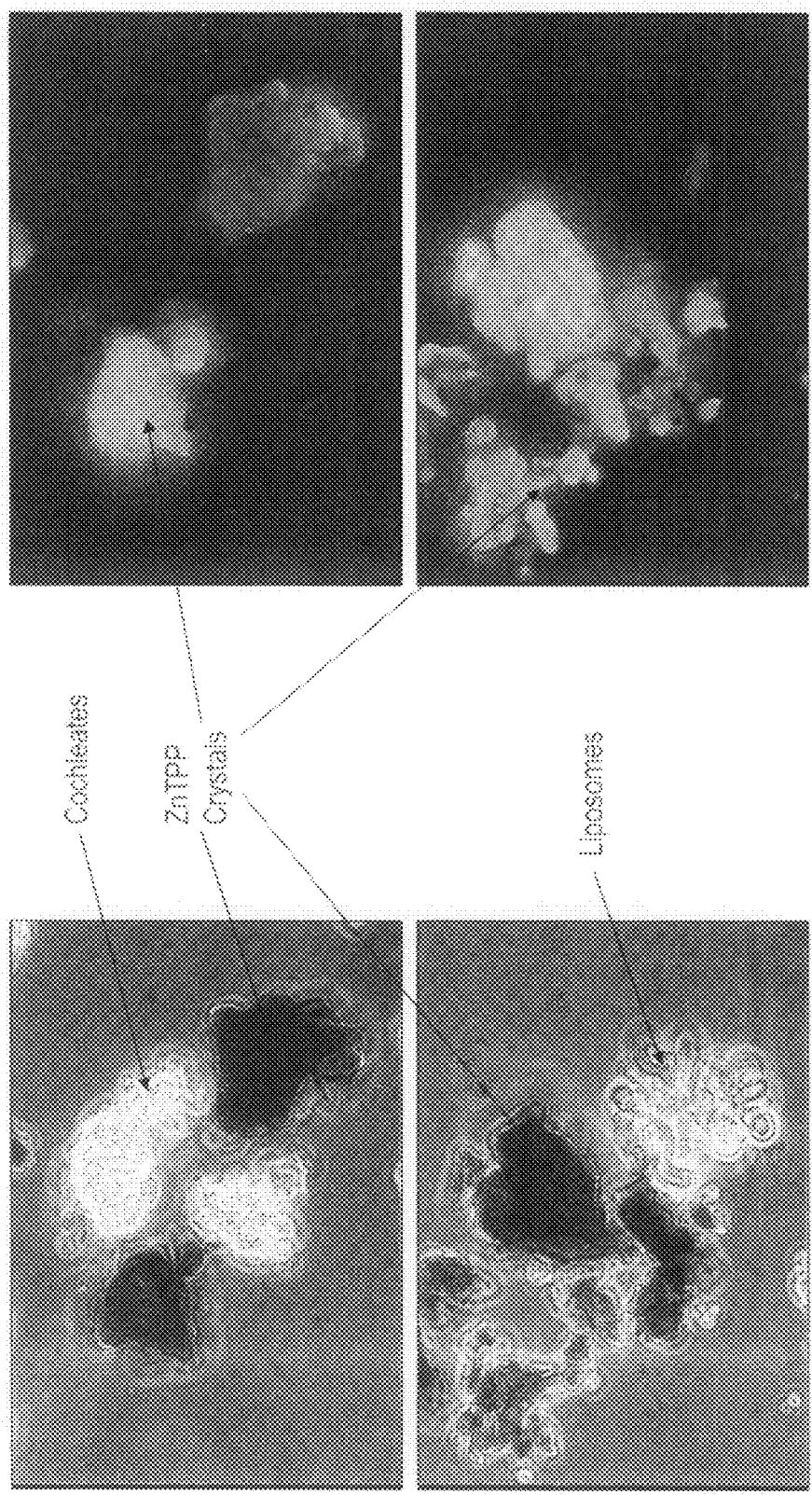
FIG. 24 is a series of phase contrast images (left panels) and fluorescence images (right panels), of ZnTPP-cochleates (top panels) and ZnTPP liposomes (bottom panels) formed without the presence of solvent.

FIG. 24 is a series of phase contrast images (left panels) and fluorescence images (right panels), of ZnTPP-cochleates (top panels) and ZnTPP-liposomes (bottom panels) formed without the presence of solvent. FIG. 24 indicates that the ZnTPP did not successfully associate with the liposomes or cochleates in the absence of solvent.

Interaction of ZnTPP-Cochleates with SKOV3 Cells

In order to study any interaction of the cochleates with cells, ZnTPP-cochleates and free ZnTPP (in solution with DMSO) were introduced to SKOV3 cell cultures, and imaged with fluorescence under a confocal microscope.

Figure 25:
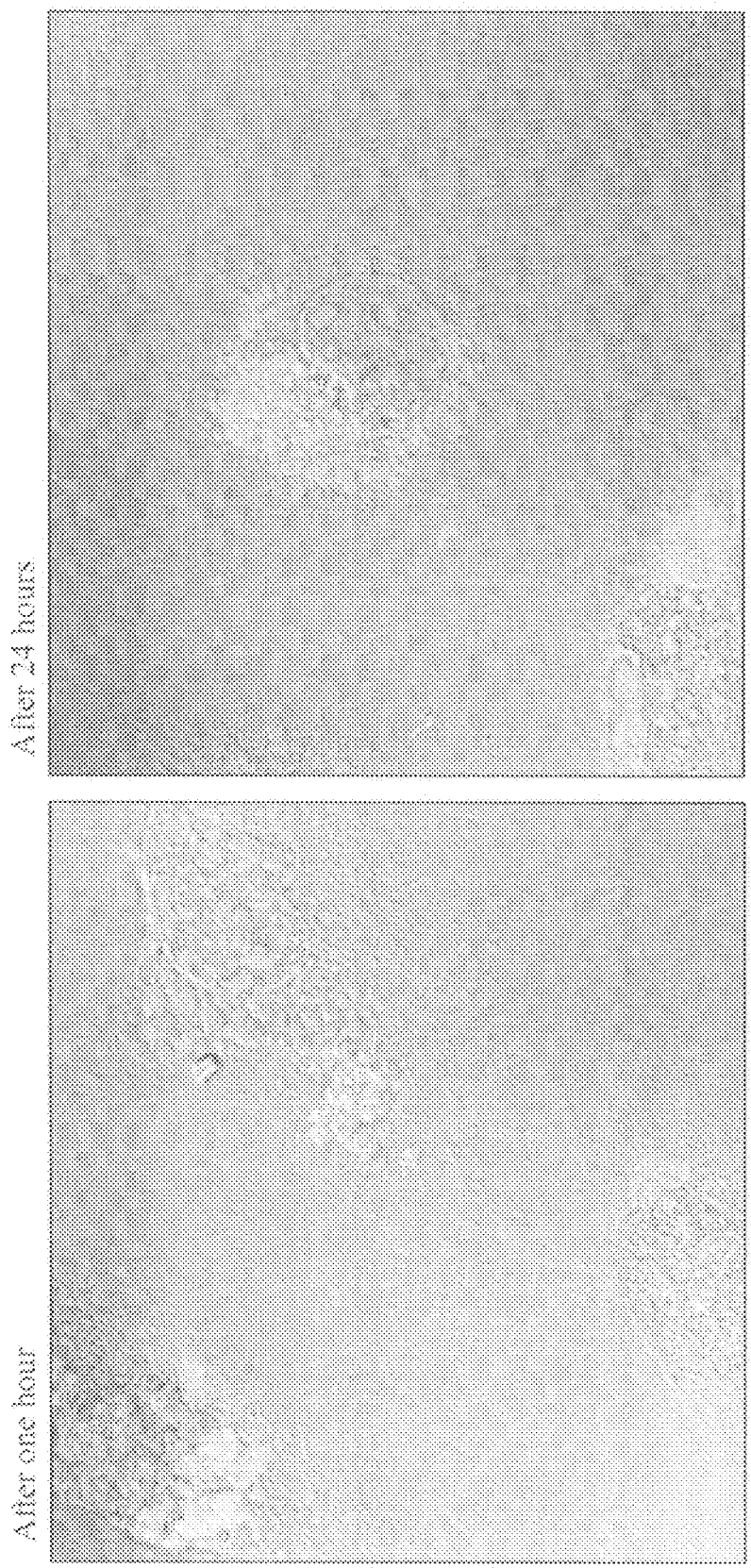
FIG. 25 is a series of images of the SKOV3 cell culture with the ZnTPP cochleates at 1 hour and 24 hours.

FIG. 25 is a series of images of the SKOV3 cell culture with the ZnTPP cochleates at 1 hour and 24 hours. The images demonstrate uptake of the ZnTPP-cochleates into the perinuclear region, and that the ZnTPP had not significantly degraded at 24 hours.

Figure 26:
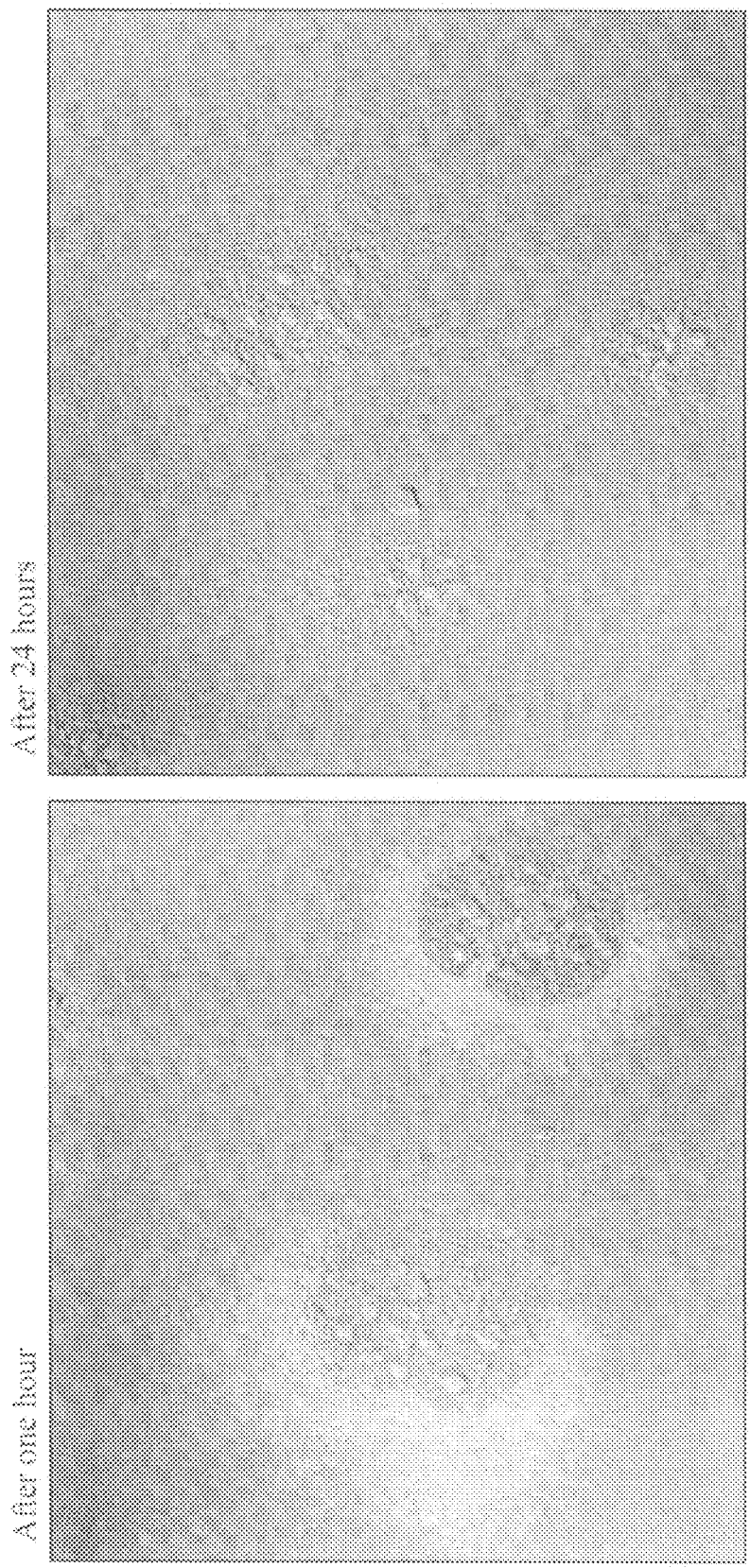
FIG. 26 is a series of images of the SKOV3 cell culture with the free ZnTPP (in DMSO) at 1 hour and 24 hours.

FIG. 26 is a series of images of the SKOV3 cell culture with the free ZnTPP (in DMSO) at 1 hour and 24 hours. The images indicate high uptake of the ZnTPP solution at one hour, but significant degradation at 24 hours. The appearance and distribution of ZnTPP is different than that observed with the ZnTPP cochleates of FIG. 25.

Study of ZnTPP-Cochleates Using a Lipid Imaging Agent

Cochleates were prepared with and without ZnTPP as described above, except that prior to introduction of the ZnTPP/solvent, liposomes were formed with 1% diolyl phosphatidylethanolamine (DOPE) liganded to pyrene (purchased Avanti). The DOPE was incorporated into the soy PS liposomes by dissolving both DOPE and lipid in solvent, drying the solvent to a film, and using an aqueous solution to form liposomes. Confocal images were taken at 1 and 24 hours after introduction to SKOV3 cells to study the uptake and any difference in the cellular distribution of cochleate/lipid and the ZnTPP. The study of distribution was possible because DOPE-pyrene fluoresces blue, and ZnTPP fluoresces red. ZnTPP in the cochleates/liposomes appears pink.

Figure 27:
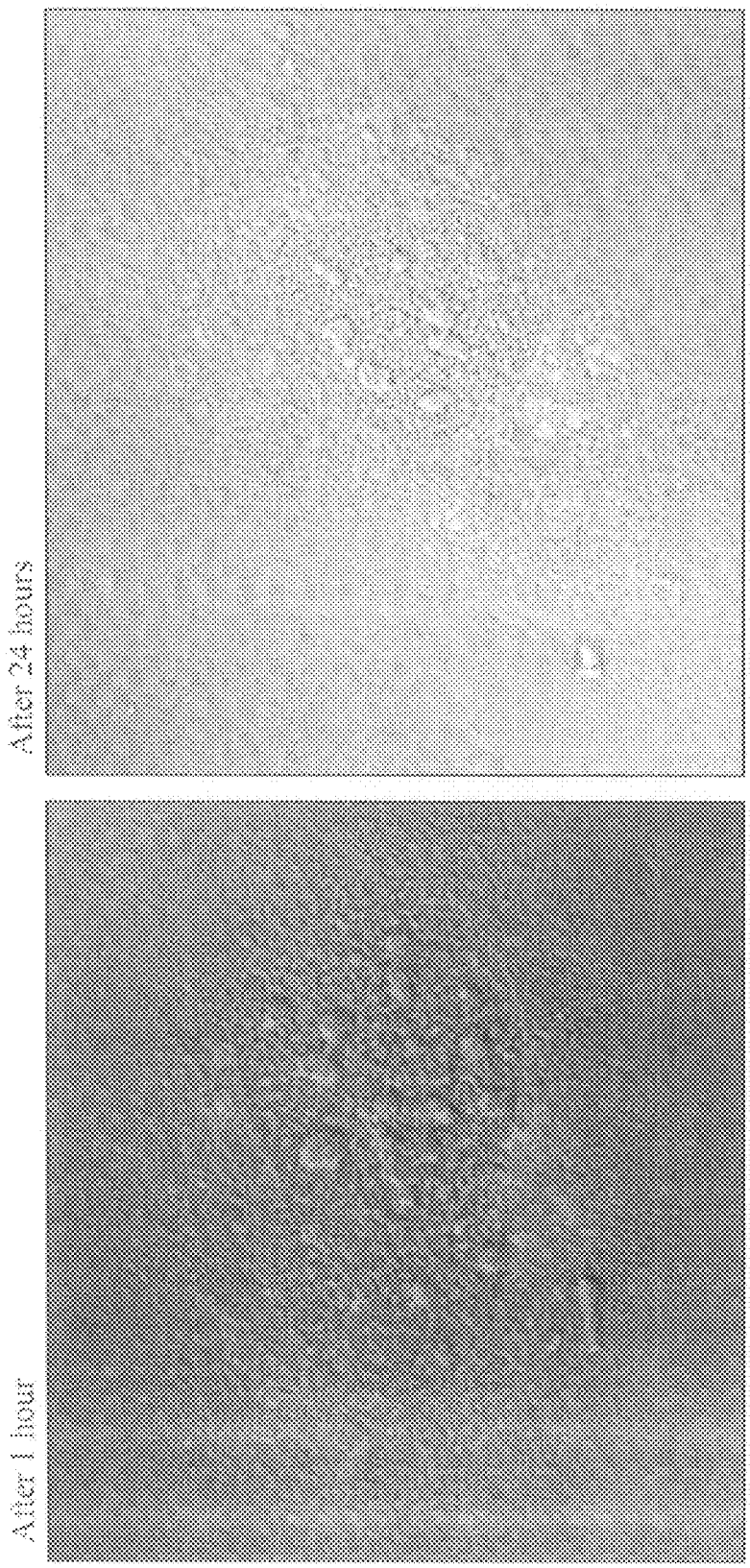
FIG. 27 is a series of images of the SKOV3 cell culture with the empty cochleates (including DOPE-pyrene lipid) at 1 hour and 24 hours.

FIG. 27 is a series of images of the SKOV3 cell culture with the empty cochleates (including DOPE-pyrene lipid) at 1 hour and 24 hours. These images indicate uptake of the empty cochleates by the cells.

Figure 28:
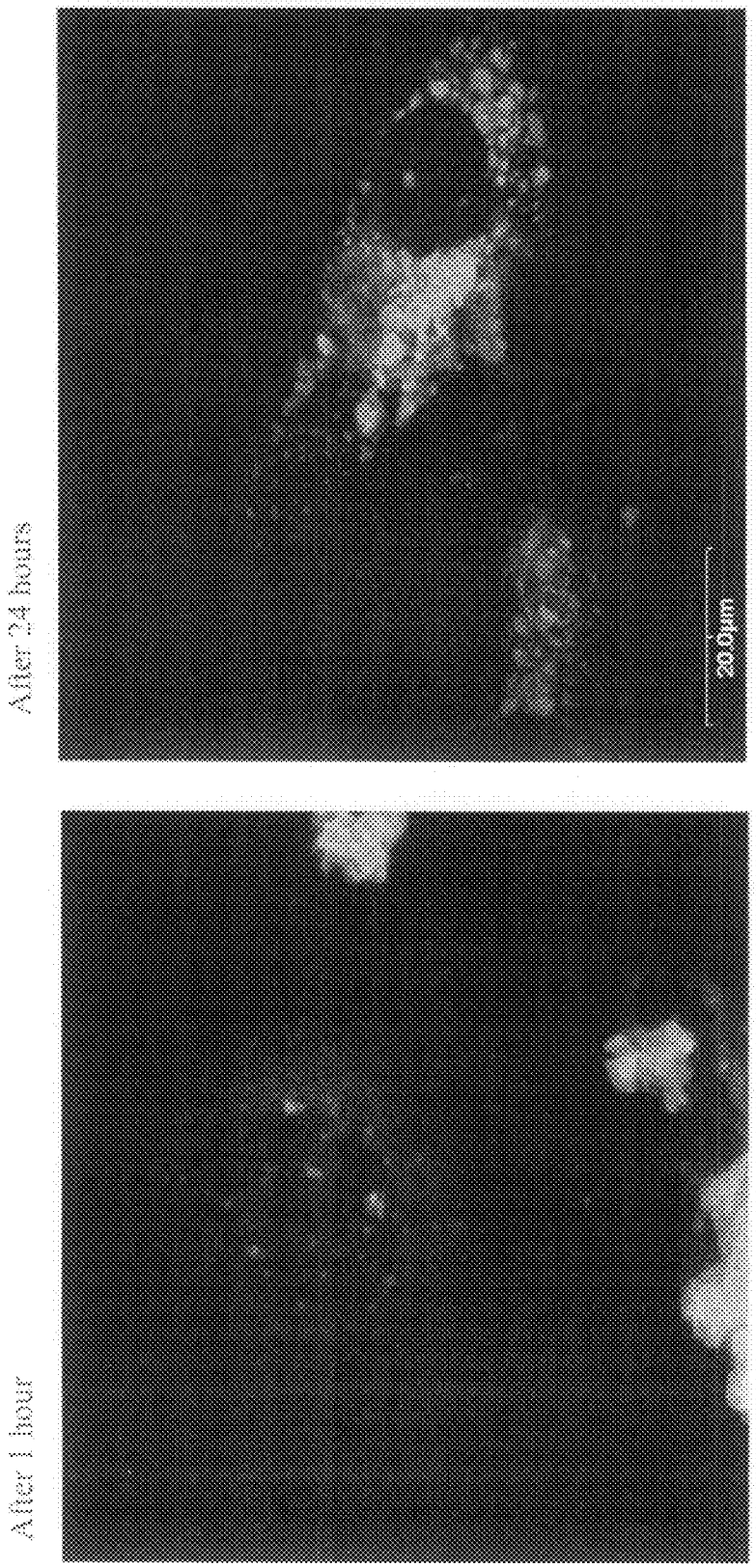
FIG. 28 is a series of images of the SKOV3 cell culture with the ZnTPP-cochleates (including DOPE-pyrene lipid) at 1 hour and 24 hours.

FIG. 28 is a series of images of the SKOV3 cell culture with the ZnTPP-cochleates (including DOPE-pyrene lipid) at 1 hour and 24 hours. These images indicate uptake of the cochleates by the cells at both 1 and 24 hours. The images also indicate a redistribution of lipid and ZnTPP in the cells at 24 hours versus 1 hour. It appears that a portion of the ZnTPP has separated from the cochleates at 24 hours.

Together, FIGS. 27 and 28 indicate high uptake of cochleates by the cell, and subsequent release of porphyrins from the cochleates in the cell. The Figures also indicate that, once inside the cell, the porphyrin is more stable in the cochleate than free.

Example 16

Preparation of NSAID Cochleates

Acetaminophen Cochleate Preparation

Acetaminophen and DOPS were mixed in a sterile, polypropylene tube with a rubber policeman. TES buffer was added to the tube to disperse the mixture in a ratio of 10 mg lipid/ml. The cochleates were formed by the slow addition (10 μL) of calcium chloride (0.1M) to the suspension of liposomes at a molar ratio of lipid to calcium of 2:1 with an external excess of 6 mM calcium and then stored at 4° C. in the absence of light.

Acetaminophen cochleates were formulated with and without aggregation inhibitor, casein, which was added to the buffer solution prior to the addition of calcium chloride in a casein to lipid ratio of 1:1 by weight.

Images were taken of the cochleates formed with (FIG. 37A, left panel) and without (FIG. 37A, right panel) the aggregation inhibitor. As demonstrated by the images, cochleates formed in the presence of casein did not aggregate as did the cochleates formed without the aggregation inhibitor.

Aspirin Cochleate Preparation

Aspirin and DOPS were solublized in chloroform in a lipid/aspirin molar ratio of 10:1 in a sterile glass tube. The sample was blown down with nitrogen to form a film. The sample was then resuspended in TES buffer, pH 7.4, at a ratio of 10 mg lipid/ml. The cochleates were formed by the slow addition (10 μL) of calcium chloride (0.1M) to the suspension of liposomes at a molar ratio of lipid to calcium of 2:1 with an external excess of 6 mM calcium and then stored at 4° C. in the absence of light.

Aspirin cochleates were formulated with and without an aggregation inhibitor, casein, which was added to the buffer solution prior to the addition of calcium chloride in a casein to lipid ratio of 1:1 by weight.

Figure 37B:
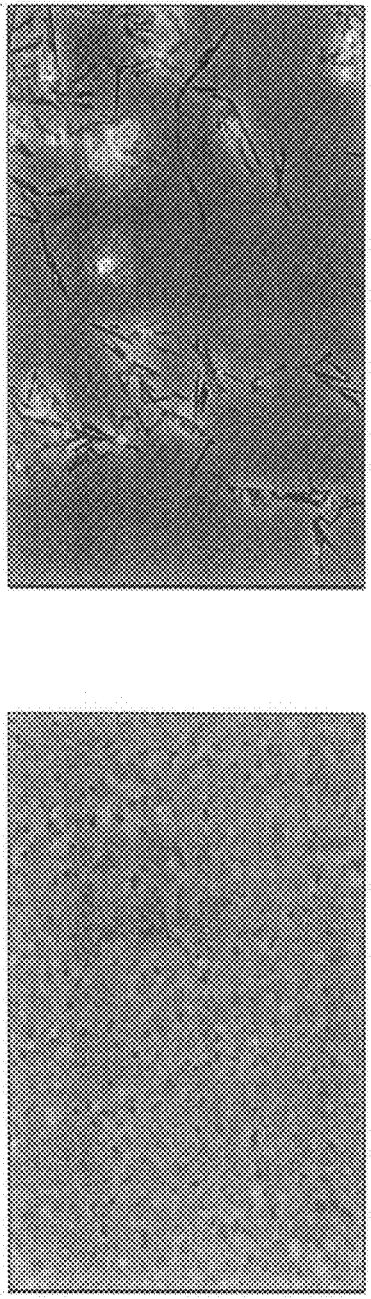
FIG. 37B is two images comparing aspirin cochleates with and without an aggregation inhibitor (casein).

Images were taken of the cochleates formed with (FIG. 37B, left panel) and without (FIG. 37B, right panel) the aggregation inhibitor. As demonstrated by the images, cochleates formed with the aggregation inhibitor did not aggregate as did the cochleates without the aggregation inhibitor, which formed needle-like structures.

SUMMARY

The introduction of an aggregation inhibitor to the cochleates loaded with a variety of cargo moieties inhibited cochleate aggregation. All cochleate formulations with casein were significantly smaller than cochleates made without casein, and these cochleates were stable for at least two months with no noticeable aggregation. Cochleates formed without casein aggregated over time.

Addition of Methylcellulose

Aspirin or acetaminophen cochleates with and without casein were prepared as described above, except that liposomes were filtered through a 0.45 μm filter followed by a 0.22 μm filter, which resulted in unilamellar liposomes which contained the drug. Calcium chloride was added to the liposomes as also described above. Methylcellulose in suspension (0.5% of entire formulation) was added and the sample was vortexed.

The addition of methylcellulose at this particular concentration did not reverse aggregation, but rather inhibited further aggregation of cochleates. The size of cochleates subsequent to addition of methylcellulose was observed to remain stable.

Example 17

Inhibition of Edema in Rat Paw

A carrageenan model was employed to study the effect of anti-inflammatory cochleates on edema in rat paws. Various aspirin cochleates of the invention were used to treat carrageenan-induced rat paw edema. These results were compared to free aspirin and indomethacin and empty cochleates to determine the efficacy of encochleated anti-inflammatory drugs. Additionally, rats in all groups were examined for gastric irritation.

Samples Tested
1. Control (no treatment)
2. Indomethacin, 6 mg/kg
3. Aspirin control, 150 mg/kg
4. Large, empty cochleates
5. Small, casein cochleates
6. Large aspirin cochleates, 45 mg/kg
7. Large aspirin cochleates, 150 mg/kg
8. Small, casein aspirin cochleates, 45 mg/kg
9. Small, casein aspirin cochleates, 140 mg/kg
10. Large casein aspirin cochleates with 0.1% Vit E, 45 mg/kg
11. Large casein cochleates with 0.1% Vit E Samples 6-10 were prepared in accordance with Example 16, except that the lipid:aspirin molar ratio was 5:1 and soy PS was used instead of DOPS. Samples 4, 5, and 11 were prepared in a similar manner in the absence of a cargo moiety. In all cases, water was used in lieu of TES buffer. All samples were given by oral gavage at 1 hour prior to injection of carrageenan on Day 0 in a volume of 3 mL of 0.5% methylcellulose. Methylcellulose at this concentration served to stabilize the cochleates but did not significantly affect the size or distribution of the standard or casein cochleates. Volumes of rat paw (in ml) were measured prior to carrageenan injection using a semi-automated plethysmograph (Buxco). At 0 time, 0.1 ml of 1% carrageenan in 0.9% pyrogen free saline was injected into the right hind paw of the rat. The paw volumes (in ml) were measured again 3 hours post carrageenan injection to determine inhibition of paw edema. Four rats from each of groups 2, 3, 6, 7, 8, 9 and 10 and one rat from each of groups 1, 4, 5 and 11 were bled (intravenously, jugular vein, approximately 1 ml blood) at 30 minutes and 4 hours post drug administration. Blood was collected in heparinized vacutainers. 4 hours post carrageenan injection, the stomachs of rats from all test groups were removed after euthanasia by $CO_2$ asphyxiation to observe for gastric irritation (i.e. bleeding and ulcerations).

Inhibition of rat paw edema for all-samples is presented in FIG. 38. In general, the control group and the groups given cochleates not containing aspirin show no decrease in the level of edema in the rat paw. Large aspirin cochleates (cochleates not made with an aggregation inhibitor) show a decrease in edema only slightly larger than that of free aspirin or indomethacin. Small cochleates (with an aggregation inhibitor), however, show a significant decrease in edema in comparison to both free aspirin and indomethacin and large aspirin cochleates. Additionally, large aspirin cochleates with vitamin E show more of a decrease in edema when compared to plain large aspirin cochleates.

Figure 39:
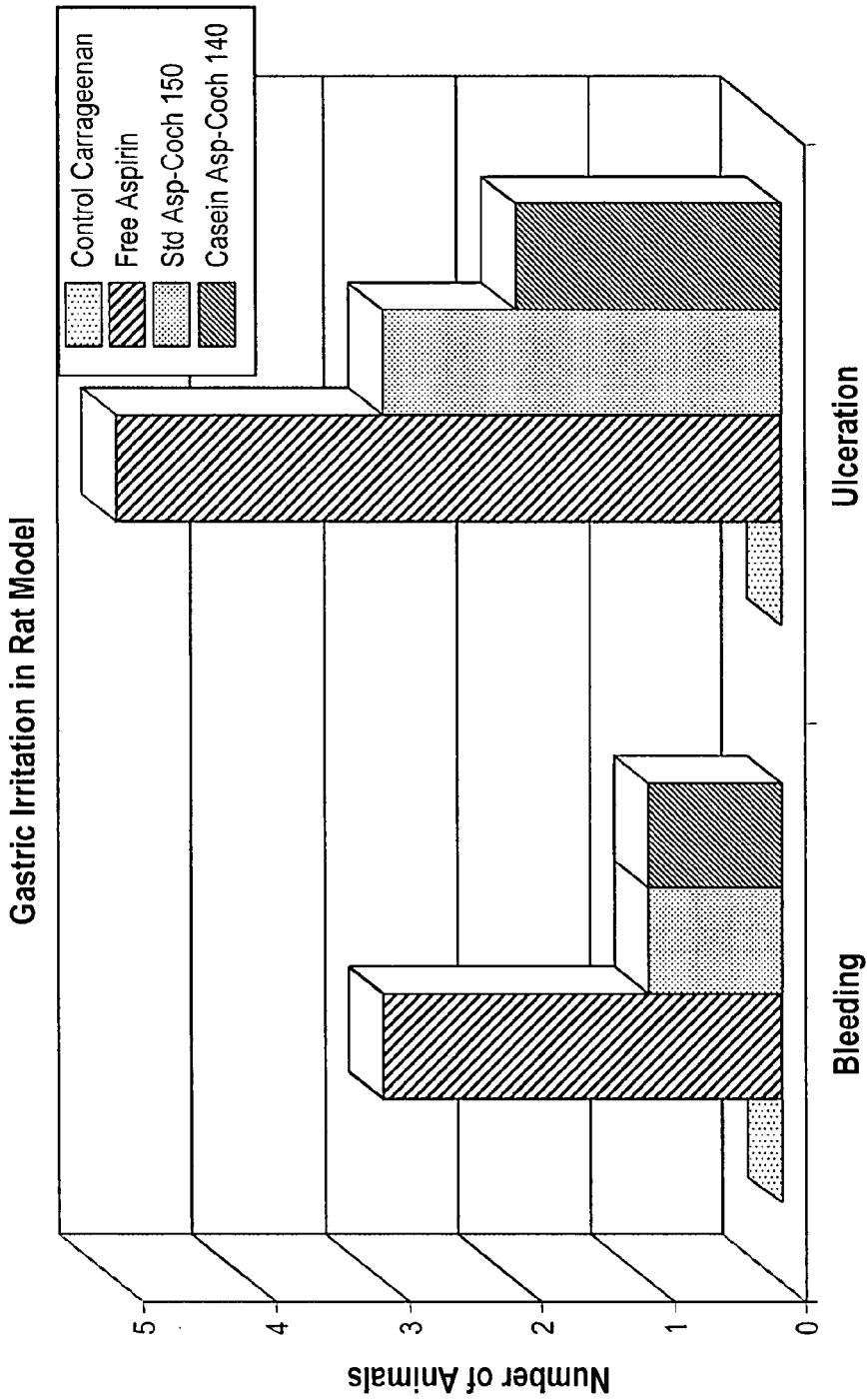
FIG. 39 is a graph showing the extent of ulceration and bleeding in rats treated with free indomethacin, free aspirin, standard aspirin cochleates, and aspirin cochleates with an aggregation inhibitor versus an untreated control.

FIG. 39 shows the incidence and level of severity of gastric irritation produced by samples 2, 3, 7 and 9. In general, indomethacin produced the greatest gastric irritation, followed by unencochleated aspirin. Aspirin cochleate formulations produced less incidence of irritation when compared to both aspirin and indomethacin.

Example 18

Activation of Macrophages by Anti-Inflammatory Cochleates

To examine the effects of cochleates on lipopolysaccharide (LPS) plus IFN-γ induced NO production, J774A.1 macrophages were treated with LPS plus IFN-γ in the presence and absence of empty cochleates. Macrophages were also treated with and without empty cochleates in the absence of LPS plus IFN-γ.

Since NO production requires the enzymatic activity of NOS, its activity was measured by NO secretion using the method of Griess (nitrite). Briefly, 100 μl of sample was reacted with the Griess reagent at room temperature for 10 minutes. Amount of $NO_2$ was then determined by measuring the absorbance at 540 nm in a microplate reader. The standard curve was obtained using the known concentration of sodium nitrite. In all experiments, $NO_2$ concentration in wells containing medium only was also measured as a blank control.

FIG. 40 indicates that empty cochleates (EC) are immunologically inert. That is, they neither enhance nor inhibit NO production induced by LPS plus IFN-γ at all concentrations assayed. In contrast, the addition of LPS plus IFN-γ to the macrophages with and without empty cochleates resulted in a dramatic increase in iNOS production. In addition, all concentrations of the empty cochleates showed no sign of cellular toxicity as was observed under phase contrast microscopy.

In order to determine the in vitro efficacy of anti-inflammatory cochleates of the invention, J774A.1 mouse macrophages were incubated with LPS (1 μg/ml) plus IFN-γ (10 μg/ml) in the presence or absence of standard aspirin cochleates and acetaminophen cochleates prepared as described in Example 16, free aspirin, free acetaminophen and empty cochleates (control) for 15 hrs.

As shown in FIG. 41, standard cochleates containing aspirin and acetaminophen exhibited greater in vitro efficacy than free aspirin and acetaminophen at inhibiting NO production.

Example 19

Particle Size Analysis of Cochleates of the Invention

Figure 34A:
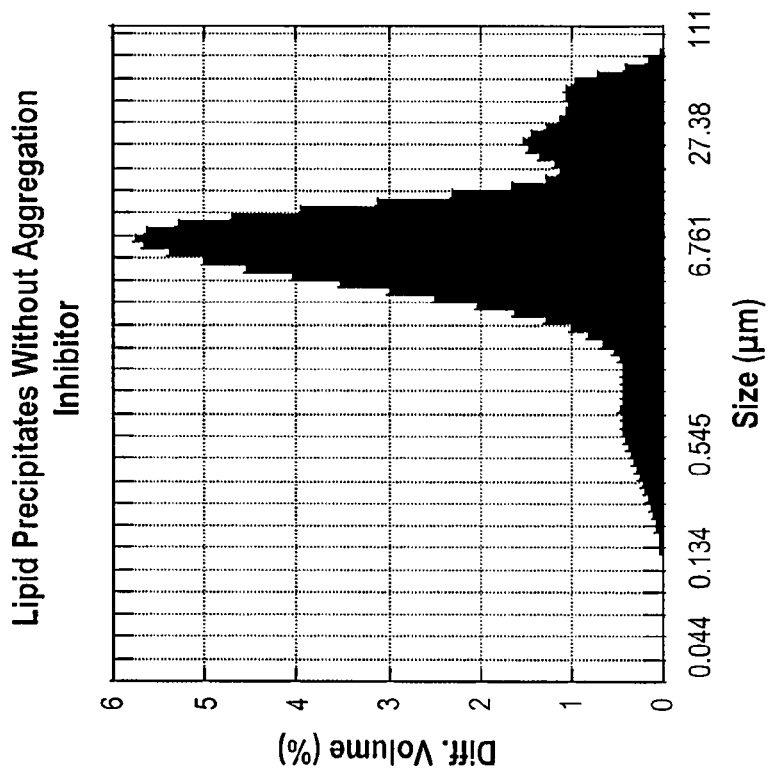
FIGS. 34A and 34B are two graphs depicting the size distribution of cochleates of the invention and standard cochleate aggregates.

Cochleates stabilized with 1% casein were evaluated with the N4 plus from Coulter. Briefly, 20 μl of the suspension of empty cochleates prepared in accordance with Example 17 (without NSAIDs) were added to 2.5 ml of D.D. $H_2O$. The samples were equilibrated over 20 minutes. The samples were then analyzed for 2 minutes at a 90° angle. Two different populations of cochleates were observed, one centered at 25 nm, and the other one at 350 nm (FIG. 34A). The population centered at about 25 nm likely consists of casein micelles and not cochleates. Any such micelles can be removed, e.g., by centrifugation.

Figure 34B:
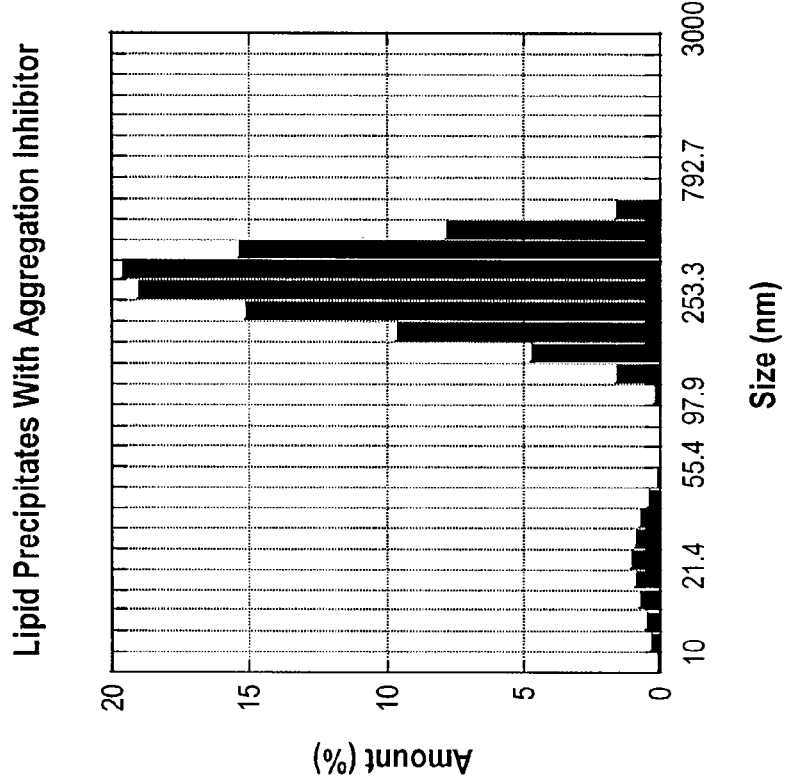

The particle size of aggregated, standard cochleates was also evaluated using the LS230 from Coulter. 100 μl to 200 μl of the sample was added to 250 ml of washing buffer in the vessel until the PIDS (Polarization Intensity Differential Scattering) reached 45%. The duration time for a run was 120 s and the number of cycles was 3. Four different populations, one centered at approximately 1 μm, one at approximately 10 μm, one at approximately 30 μm and the last one at approximately 50 μm were observed. (FIG. 34B)

Example 20

Preparation of Cochleates with Various Aggregation Inhibitors

Rhodamine labeled phosphatidyl ethanolamine (Rho-PE) liposomes were prepared by adding di-oleoyl-PS (DOPS) and Rho-PS to chloroform at a ratio of 10 mg lipid/ml solvent. The DOPS was present at 0.1% or 0.01% of the total lipid. The sample was blown down under nitrogen to form a film. Once dry, the sample was resuspended in a TES buffer at a ratio of 10 mg lipid/ml buffer. The liposomes were then passed through a 0.22 μL filter. The homogeneous population of Rhodamine labeled liposomes were stored at 4° C. in the absence of light under nitrogen.

Sterile glass tubes, each containing 100 μl fluorescent Rhodamine cochleates in TES buffer were prepared Cochleates were formed by the addition of 10 μl aliquots of 0.1M calcium chloride until a molar ratio of lipid to calcium of 2:1 and an external excess of 6 mM calcium was reached. 10 μl Half and Half was added to one tube and vortexed for 4 minutes. Whole milk, at a 1:1 ratio of whole milk to lipid, was added to a second tube and vortexed for one minute. Evaporated fat free milk, at a 1:2 weight ratio of evaporated milk to lipid was added to a third tube and vortexed for 4 minutes. A fourth tube was used as the control, and as such, no aggregation inhibitor was added.

FIGS. 35A-D are four fluorescent images of the Rhodamine-labeled cochleates obtained. The Figures demonstrate the effect of formulating cochleates, in the presence of various aggregation inhibitors: half and half (FIG. 35A), whole milk (FIG. 35B), and fat-free milk (FIG. 35C). FIG. 35D is an image of the control composition of cochleates that do not include an aggregation inhibitor.

FIG. 36 depicts the aggregated cochleates prior to the addition of milk (left image) and after the addition of milk (right image). These images indicate that milk caused aggregation to reverse.

Example 21

Uptake of Cochleates by Macrophages

Rhodamine labeled phosphatidyl ethanolamine (Rho-PE) cochleates were prepared as described in Example 20, except that casein was added to the formulation prior to the addition of calcium in a casein to lipid ratio of 1:1. Additionally, no milk products were added to the casein-coated Rho-PE cochleates.

Sterile cover slips were placed in the wells of 24-well plates. J774.1 macrophages were harvested as described above, counted using a hemacytometer and seeded at a concentration of $1 \times 10^5$, and allowed to incubate overnight to ensure adherence. Rhodamine-PE cochleates were then added at a final concentration of 50 μg lipid/ml and 5 μg lipid/ml.

Figure 33A:
FIG. 33A is two fluorescent images demonstrating the uptake of standard cochleates by cultured cells.
Figure 33B:
FIG. 33B is two fluorescent images demonstrating the uptake of cochleates of the invention by cultured cells.

The cover slips were removed at the desired time point, generally about one hour, rinsed in DMEM to remove any free cochleates, placed inverted on microscope slides and observed for uptake using phase contrast and fluorescence microscopy. Standard cochleate formulations were observed to remain within the macrophage for several days and slowly transfer the fluorescent lipid from endocytic vesicles throughout the rest of the macrophage. In contrast, the nanocochleates were only observed up to 36-hours after administration. Due to their size and/or altered surface characteristics, the cochleates with casein were taken up more aggressively than standard cochleates (without casein) by cultured cells. Nearly every cell incubated with the cochleate composition prepared with casein showed intracellular fluorescence, indicating that the cochleates were rapidly taken up by the macrophages (FIG. 33B). In contrast, standard cochleates were not taken up as aggressively by the macrophages as is shown by intracellular fluorescence (FIG. 33A).

Example 22

Cochleates Formed with Protonized Vancomycin

Cochleates Formed with and without Calcium

Vancomycin cochleates are expected to increase the oral bioavailability of vancomycin while limiting its side effects. Vancomycin cochleates were formed with and without calcium.

14.6 mg of Dioleoyl Phosphatidylserine (DOPS, Avanti, Ala.) was used as the starting lipid material for each cochleate formulation. The phospholipid powder and 7.6 mg protonized Vancomycin (Vanco) powder were mixed in a molar ratio of 4.3:1.1 mL of modified TES buffer (2 mM TES, 150 mM NaCl, 2 mM L-Histidine), adjusted at pH 3 was added to each mixture. To one formulation, calcium also was added. The mixture was vortexed for 2 minutes.

Figure 43:
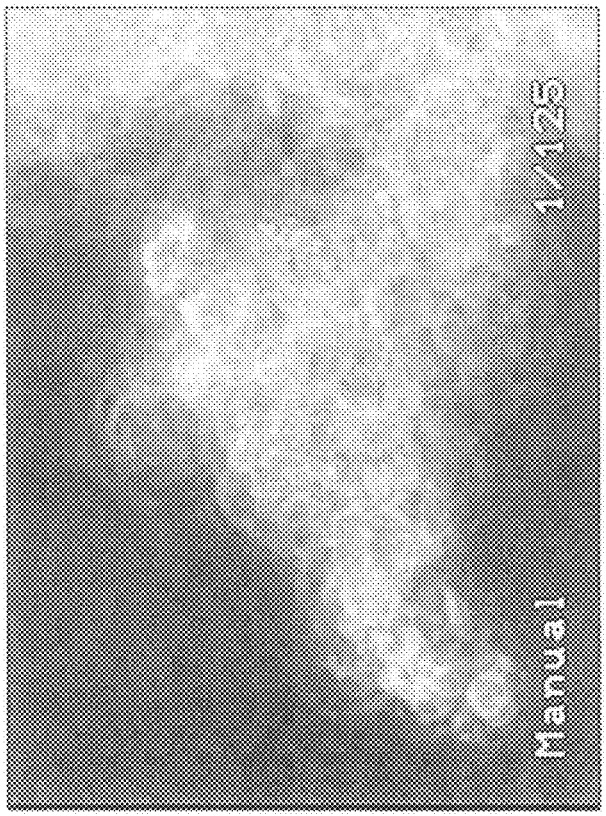
FIG. 43 is an image of a cochleate prepared in the presence of calcium.
Figure 42:
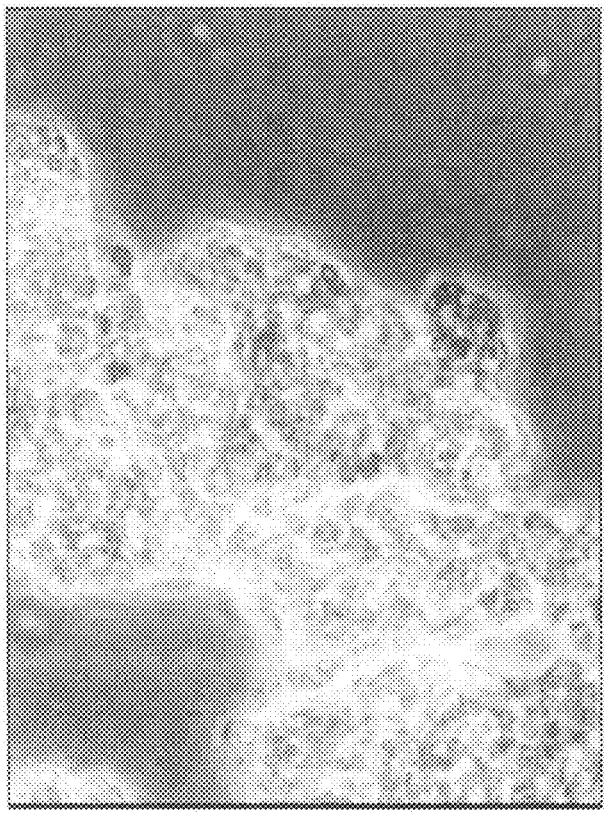
FIG. 42 is an image of a cochleate prepared in the absence of calcium.

Optical microscopy, using phase contrast technique, revealed the presence of cochleates in both the formulation without calcium (FIG. 42), and the formulation with calcium (FIG. 43). The cochleates were centrifuged at 3000 rpm at 4° C. for 20 min. The content of Vanco in the aggregates was assessed by OD absorption at 282 nm with a spectrophotometer. Results showed that the lipid associated with the Vanco such that the vancomycin comprised about 40% of the precipitate by weight for the formulation without calcium and about 70% of the precipitate for the formulation with calcium.

Figure 44:
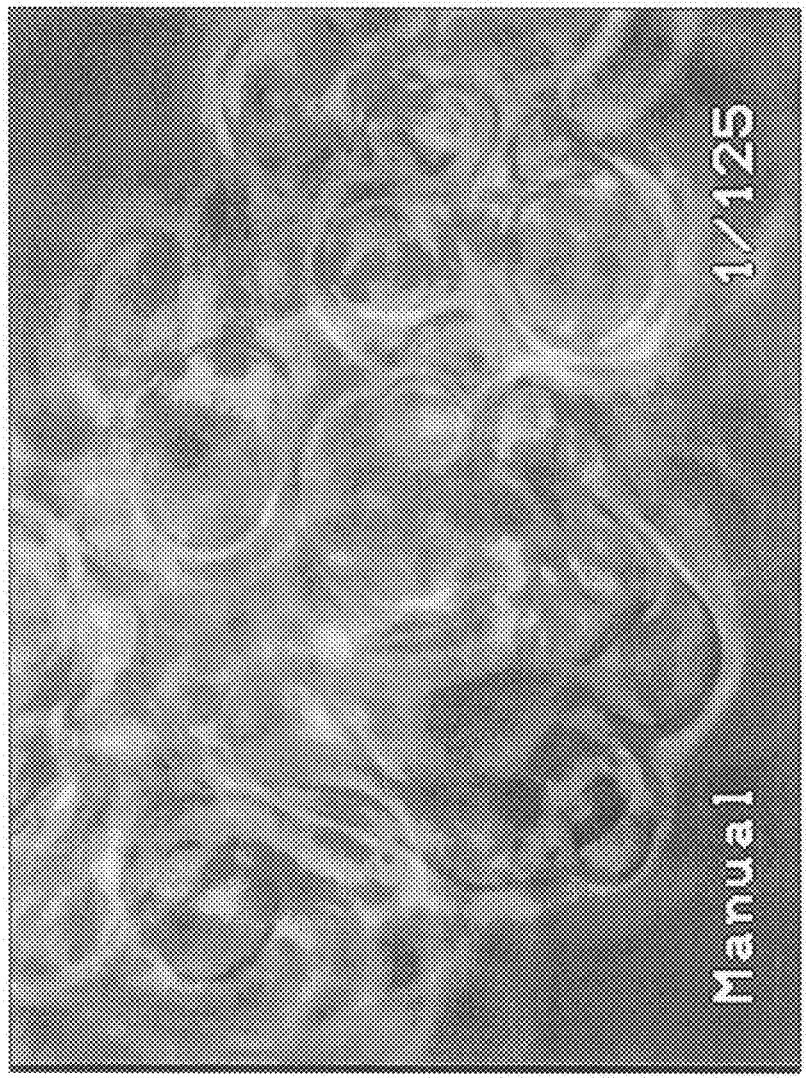
FIG. 44 is an image of a cochleate prepared in the presence of calcium and subsequently treated with a molar excess of chelating agent (EDTA).

Addition of EDTA chelating agent to the formulation with calcium resulted in a rapid transformation of the cochleate into opened structure (FIG. 44), suggesting that the cochleates included stacked sheets of lipid bilayer and cationic drug.

Cochleates Formed with Alternative Acidification Step

Figure 45:
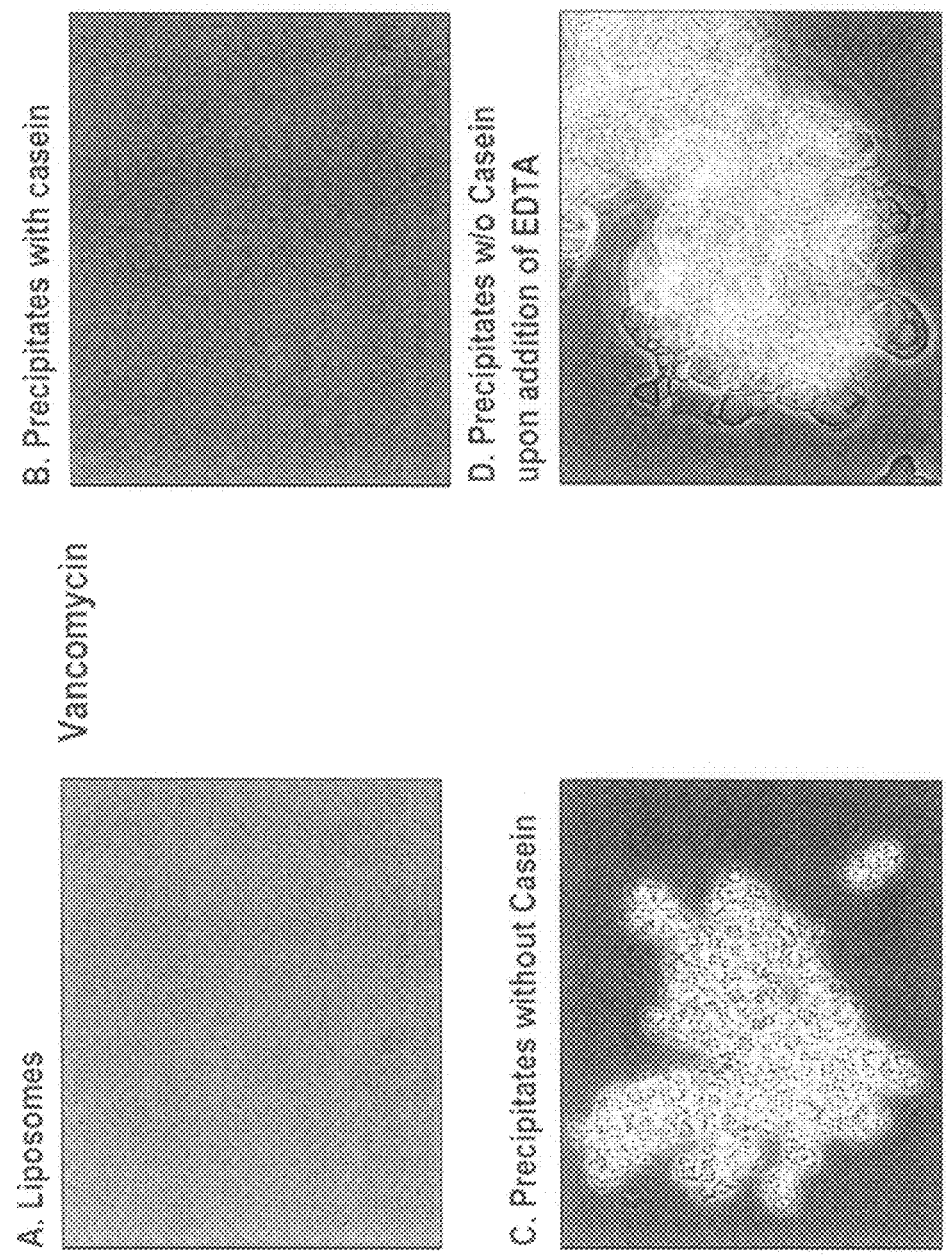
FIGS. 45A-D are images depicting vancomycin-lipid formulations.

Vanco crystals were added to preformed DOPS liposomes (FIG. 45A). The vanco was solubilized as TES buffer (pH 7.4) was added to disperse the mixture in a ratio of 10 mg lipid/ml. HCl (0.1N) was used to bring the pH to 5.0 or 6.5, at which point an association of the Vanco with the lipid were visible under the microscope. The protonized Vanco was observed to associate with the negatively charged bilayer surface. 10 μL of calcium chloride (0.1M) then was slowly added to the suspension of liposomes at a molar ratio of lipid to calcium of 2:1 with an external excess of 6 mM calcium and then stored at 4° C. in the absence of light.

Cochleates Formed with and without an Aggregation Inhibitor

Vancomycin cochleates were formulated with an acidification step as described above with and without an aggregation inhibitor (casein), which was added to the buffer solution prior to the addition of calcium chloride in a casein to lipid ratio of 1:1 by weight.

Images were taken of the cochleates formed with (FIG. 45B) and without (FIG. 45C) casein. When EDTA was added to the cochleates, they were opened to form liposomes as shown in FIG. 45D. The efficacy of the cochleates against *Staph. aureus* was studied in vitro as described in Example 24, below.

Example 23

Cochleates Formed with Tobramycin

Cochleates Formed with Acidification Step

Figure 48:
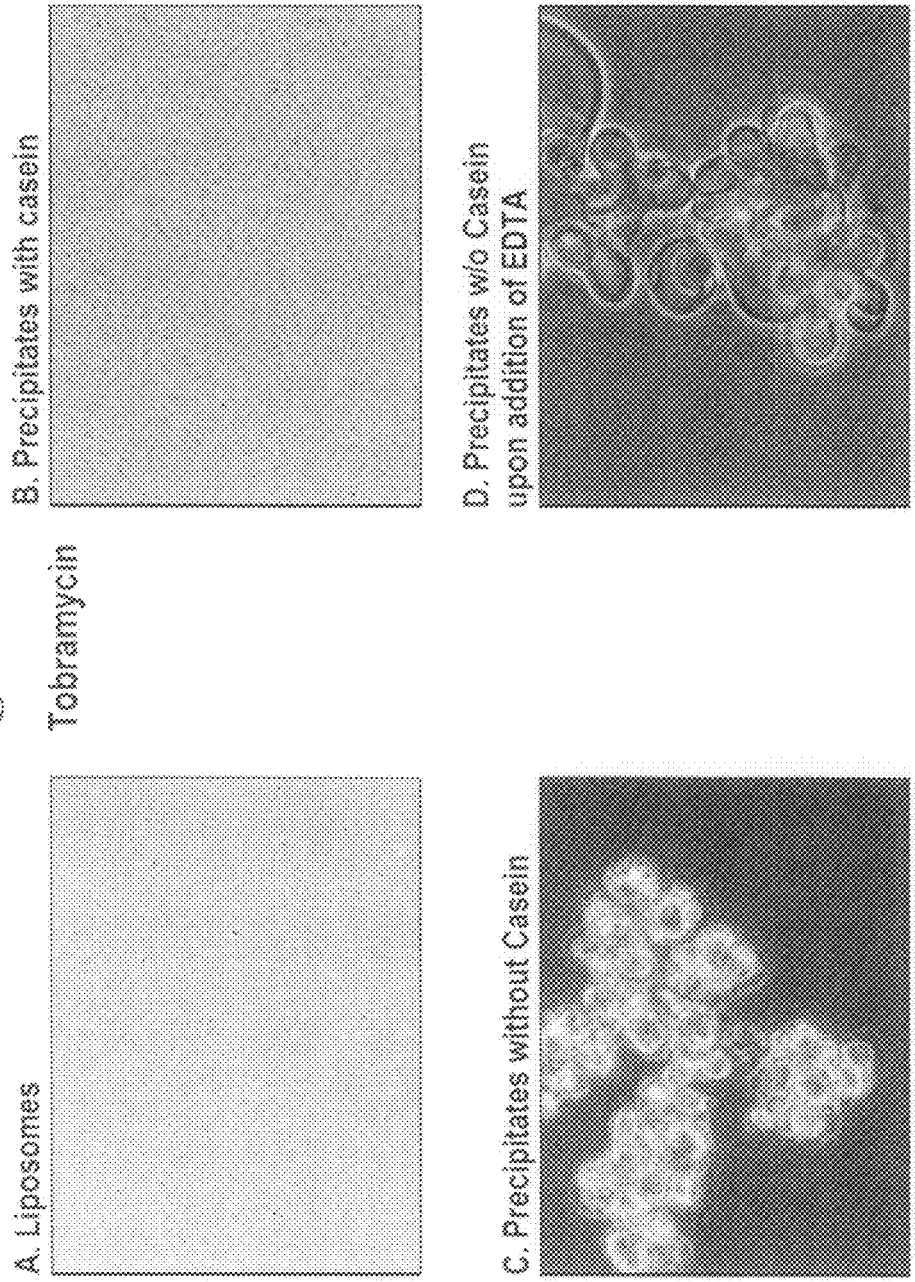
FIG. 48 are images depicting tobramycin-lipid formulations.

Tobramycin crystals were added to pre-formed liposomes (FIG. 48A). Tobramycin was solubilized as TES buffer (pH 7.4) was added to disperse the mixture in a ratio of 10 mg lipid/ml. HCl (0.1N) was used to bring the pH to 5.5, at which point an association of the tobramycin with the lipid were visible under the microscope. The protonized tobramycin was observed to associate with the negatively charged bilayer surface. 10 μL of calcium chloride (0.1M) was slowly added to the suspension at a molar ratio of lipid to calcium of 2:1 with an external excess of 6 mM calcium and then stored at 4° C. in the absence of light.

Cochleates Formed with and without an Aggregation Inhibitor

Tobramycin cochleates were formulated with and without an aggregation inhibitor (casein), which was added to the buffer solution prior to the addition of calcium chloride in a casein to lipid ratio of 1:1 by weight.

Images were taken of the cochleates formed with (FIG. 48B) and without (FIG. 48C) casein. EDTA was added to the cochleates of FIG. 48C and the cochleates were observed to open as shown in FIG. 48D. The efficacy of the cochleates against *Staph. aureus* was studied in vitro as described in Example 24, below.

Example 24

Bactericidal Activity of Cochleates

J774A.1 is a well characterized murine macrophage-like cell line that has been extensively used to study *Staphylococcal aureus*-macrophage interactions. The J774A.1 cells were maintained at −80° C. prior to use and were prepared for the phagocytosis assays as described above.

J774A.1 macrophages were counted using a hemacytometer, seeded into 96-well plates and incubated overnight. Following incubation, the macrophages were infected with *Staphylococcal aureus* or *Pseudomonas aeruginosa* at a ratio of 1:200 with respect to the macrophages.

Free Vanco and Vanco cochleates prepared with and without casein as described in Example 22, were added to the macrophages infected with *Staph. A.* at concentrations of 1, 5, 10, and 25 μg/ml.

Free tobramycin and tobramycin cochleates prepared as described in Example 23 with and without casein were added to the macrophages infected with *P. aeruginosa* and *P. aeruginosa* alone at concentrations of 1, 5, 10, and 25 μg/ml.

Following incubation for 3 and 6 hours, the plates were removed and observed. Medium was removed and replaced with 100 μl cold sterile water. The plates were incubated 10 minutes, at which point the 100 μl cold sterile water was pipetted vigorously to disrupt the cellular membrane. 25 μl of this suspension was placed onto Sabouraud Dextrose Agar plates, and placed in a dry incubator overnight at 37° C. *Staphylococcal aureus* or *Pseudomonas aeruginosa* colony forming units (CFU's) were counted the to following day.

Figure 46:
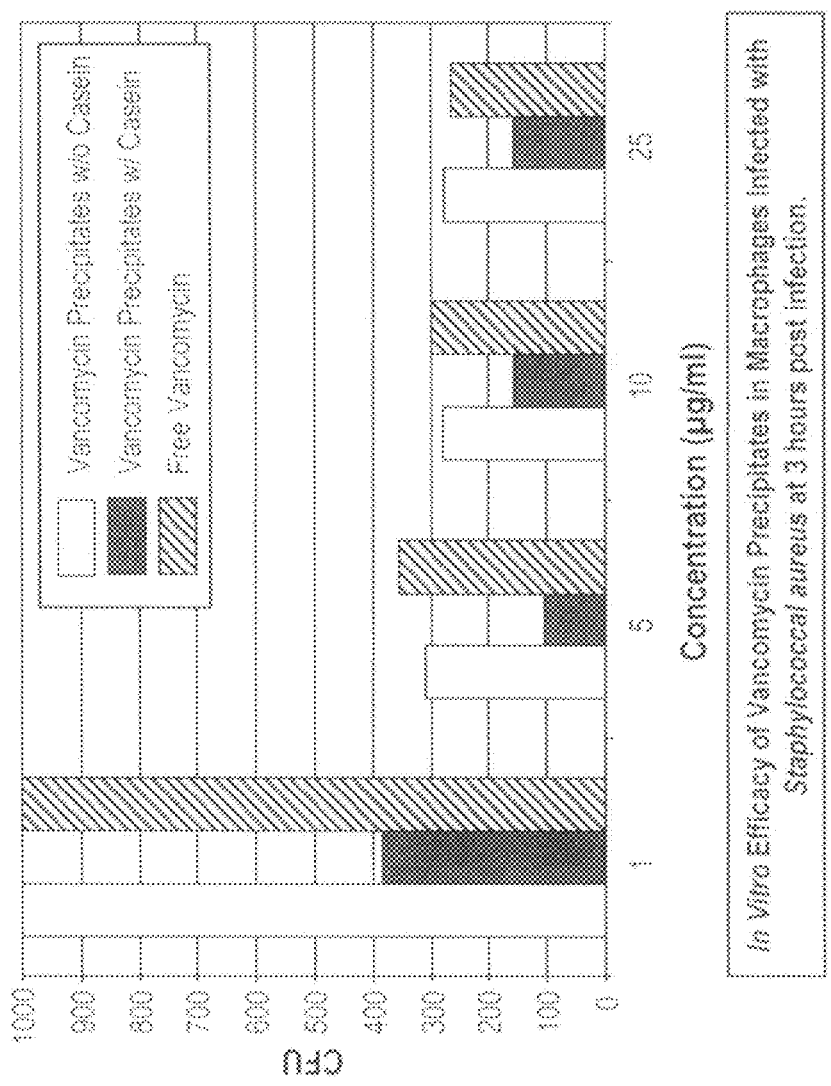
FIG. 46 is a graph summarizing efficacy data for free vancomycin, and vancomycin cochleates with and without casein on *S. aureus* at 3 hours.
Figure 47:
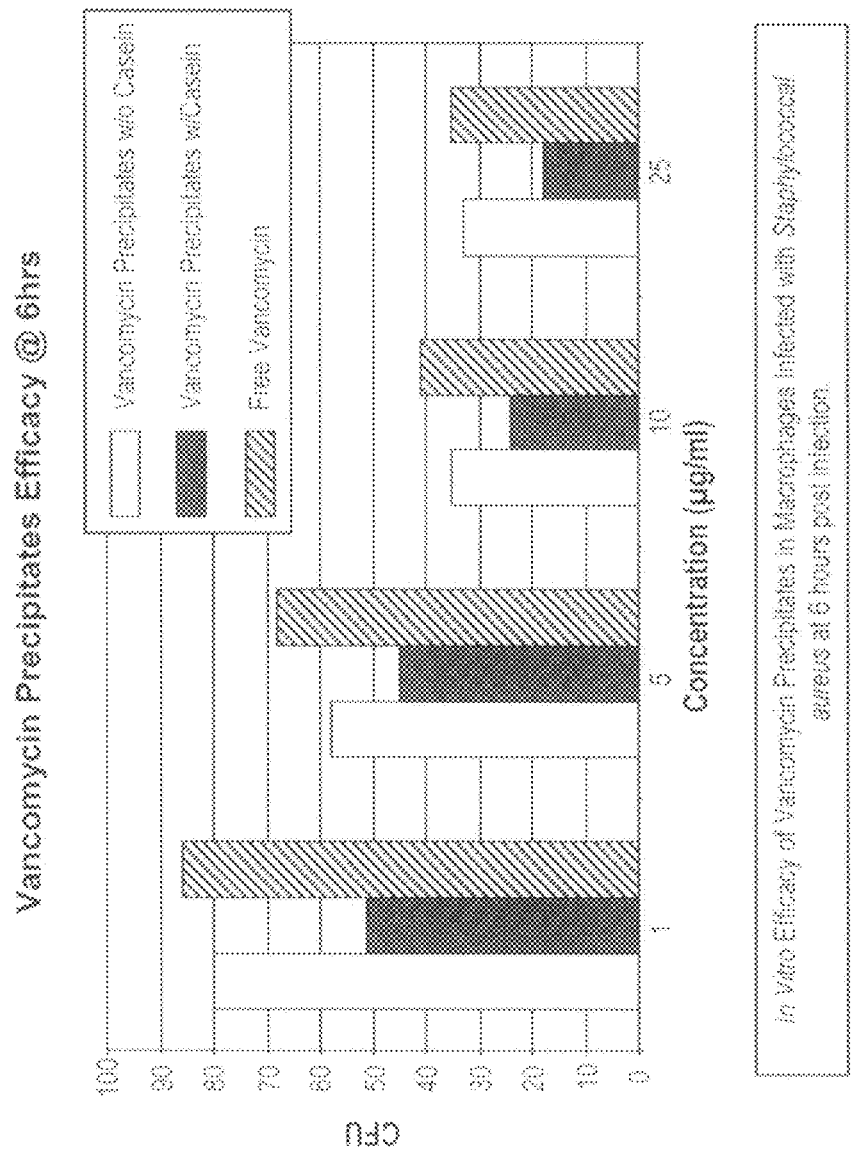
FIG. 47 is a graph summarizing efficacy data for free vancomycin, and vancomycin cochleates with and without casein on *S. aureus* at 6 hours.

FIGS. 46 and 47 are graphs demonstrating the efficacy data for the Vanco cochleates (with and without casein) against Staphylococcal aureus versus free vancomycin at 3 and 6 hours after administration, respectively.

Figure 49:
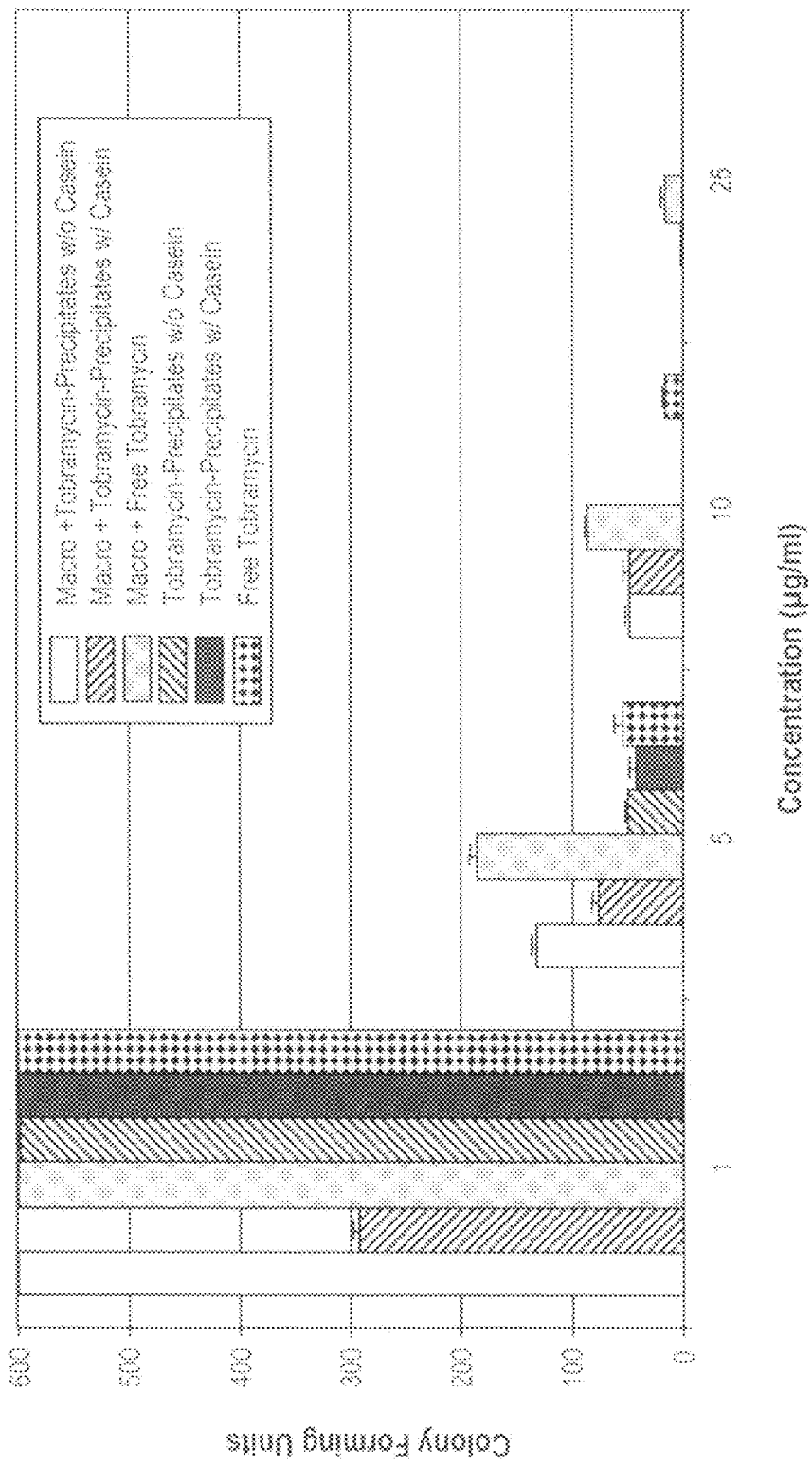
FIG. 49 is a graph summarizing efficacy data for free tobramycin and tobramycin cochleates with and without casein on *P. aeruginosa* alone and cultured in macrophages at 3 hours.
Figure 50:
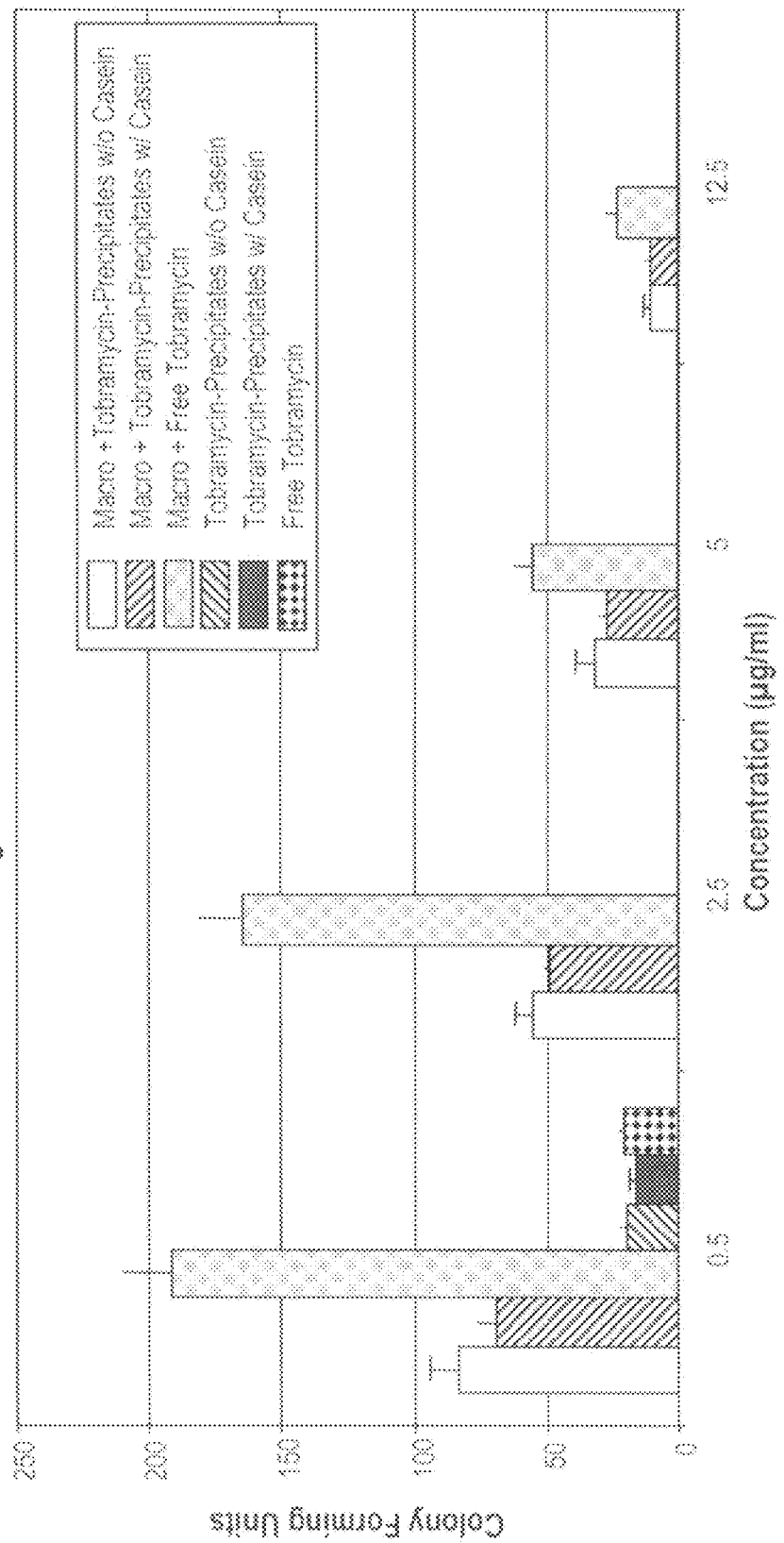
FIG. 50 is a graph summarizing efficacy data for free tobramycin, and tobramycin cochleates with and without casein on *P. aeruginosa* alone and cultured in macrophages at 6 hours.

FIGS. 49 and 50 are graphs demonstrating the efficacy of the tobramycin cochleates of the invention (with and without casein) against Pseudomonas aeruginosa, versus free tobramycin at 3 and 6 hours after administration, respectively.

As FIGS. 46, 47, 49 and 50 indicate, the cochleates of the invention increase the effectiveness of the cargo molecule against bacteria in cells. Additionally, vancomycin and tobramycin cochleates including an aggregation inhibitor show a significant increase in efficacy in relation to both free drug and cochleates formed without aggregation inhibitor.

Example 25

Caspofungin Cochleates

Cochleates Formed with Calcium—Solvent Drip Method

Soy phosphatidylserine (Soy PS, Degussa) was used as the starting lipid material for each cochleate formulation. 100 mg soy PS was mixed with 10 mL water or saline, and the mixture was vortexed, forming liposomes. 10 mg of protonized caspofungin (5 mg for 20:1 cochleates or 20 mg for 5:1 cochleates) was then dissolved in 1 mL DMSO. The DMSO solution was slowly added to the liposomal solution. After the caspofungin/soy PS liposomal solution was mixed, 1.5 mL of 0.1M calcium chloride solution was added at a rate of 10 µl/10 s in order to precipitate a solid. Resulting formulations, along with observations about cochleate morphology are presented in Table 1, below.

Cochleates Formed with Calcium—Aqueous Method

Numerous formulations using the aqueous drip method were prepared using varying combinations of starting materials. Soy phosphatidylserine (Soy PS, Degussa) and DOPS were both used as the starting lipid material for cochleate formulations using the aqueous drip method. Soy PS or DOPS (100 mg) was mixed with 5 mL water, saline, or buffer and the mixture was vortexed until liposomes formed. Protonized caspofungin (10 mg for 10:1 cochleates, 20 mg for 5:1 cochleates) was then dissolved in 5 mL water, saline, or buffer. The caspofungin solution was added slowly to the liposomal solution. After mixing, 1.5 mL of a 0.1 M calcium chloride solution was added to the caspofungin/soy PS liposomal solution at a rate of 10 µl/10 s in order to precipitate a solid caspofungin cochleate. Resultant formulations, along with observations about cochleate morphology and measurements of "free" caspofungin are presented in Table 1, below.

TABLE 1

Caspofungin cochleate formulations

| Method | PS:caspo (w/w) | PS source | Buffer/saline/ water | Morphology (+/−EDTA) | "free" caspofungin |
|---|---|---|---|---|---|
| DMSO drip | 20:1 | soy PS | water or saline | OK | ND |
| | 10:1 | soy PS | water or saline | OK | ND |
| | 5:1 | soy PS | water or saline | OK | ND |
| aqueous drip | 10:1 | DOPS | water | OK | 15% |
| | 10:1 | DOPS | saline | OK | 4% |
| | 10:1 | soy PS | water | OK | 2% |
| | 10:1 | soy PS | TES buffer | OK | 2% |
| | 10:1 | soy PS | saline | OK | 0.1% |
| | 5:1 | soy PS | saline | OK | 1% |

*"free" caspo indicates caspofungin which did not precipitate with the soy PS.

Briefly, the morphology of formulations made with both the solvent drip method and the aqueous drip method were indicative of cochleate structures. That is, they both demonstrated an opening to liposomes upon addition of EDTA. Additionally, it appears that the use of saline diminished the amount of free caspofungin in comparison to the use of water when cochleates were formulated using the aqueous drip method.

Cochleates Formed with Additional Acidification Step 100 mg soy PS was combined with 5 mL saline, and the mixture was vortexed until liposomes formed. 50 mg protonized caspofungin was then combined with 5 mL saline buffer at pH 5.5. This pH ensured that the caspofungin remained protonized and multivalent. The caspofungin solution was slowly added to the soy PS liposomes. Cochleates began to form immediately upon addition of caspofungin because of the high valency of the protonized moiety.

Figure 56:
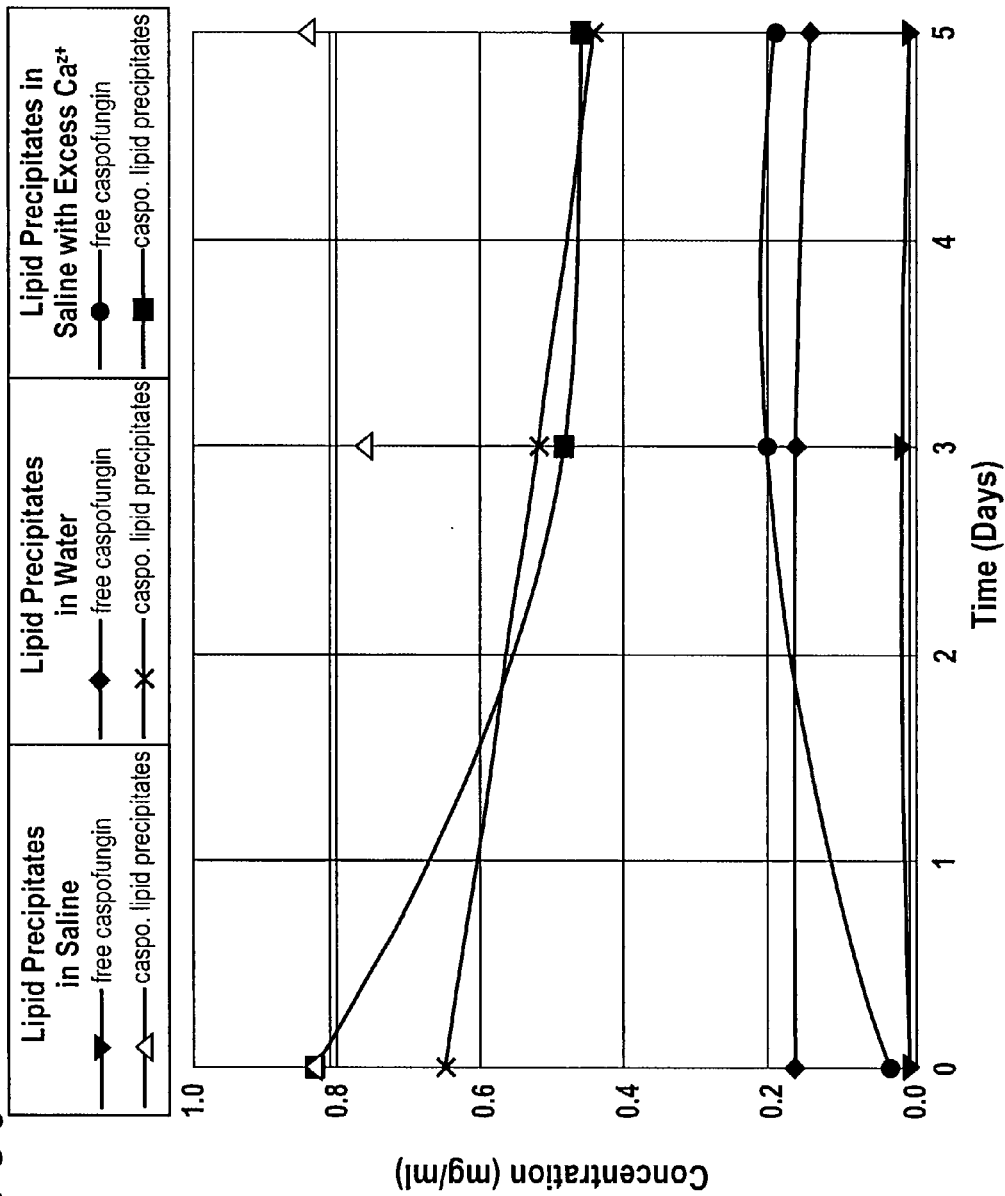
FIG. 56 is a graph depicting the stability of caspofungin cochleates formulated in water, in saline and in saline with additional calcium.

These cochleates were also formed with additional calcium, and with sterile water instead of saline. These three formulations were then maintained at 4° C. for five days in order to test the stability of the resultant cochleates. HPLC analysis of the cochleates and the supernatant was completed to measure concentration of caspofungin in both, and is summarized in FIG. 56. It is shown that in sterile water, the concentration of caspofungin in the cochleate gradually decreases, while the concentration of caspofungin not associated with a cochleate ("free caspofungin") increases. This decrease of caspofungin in the cochleates and increase in free caspofungin can also be observed for the saline formulation with excess calcium. The formulation with saline only, however, remained stable over the five day period.

Acidification of Solution Subsequent to Cochleate Formation

Figure 57:
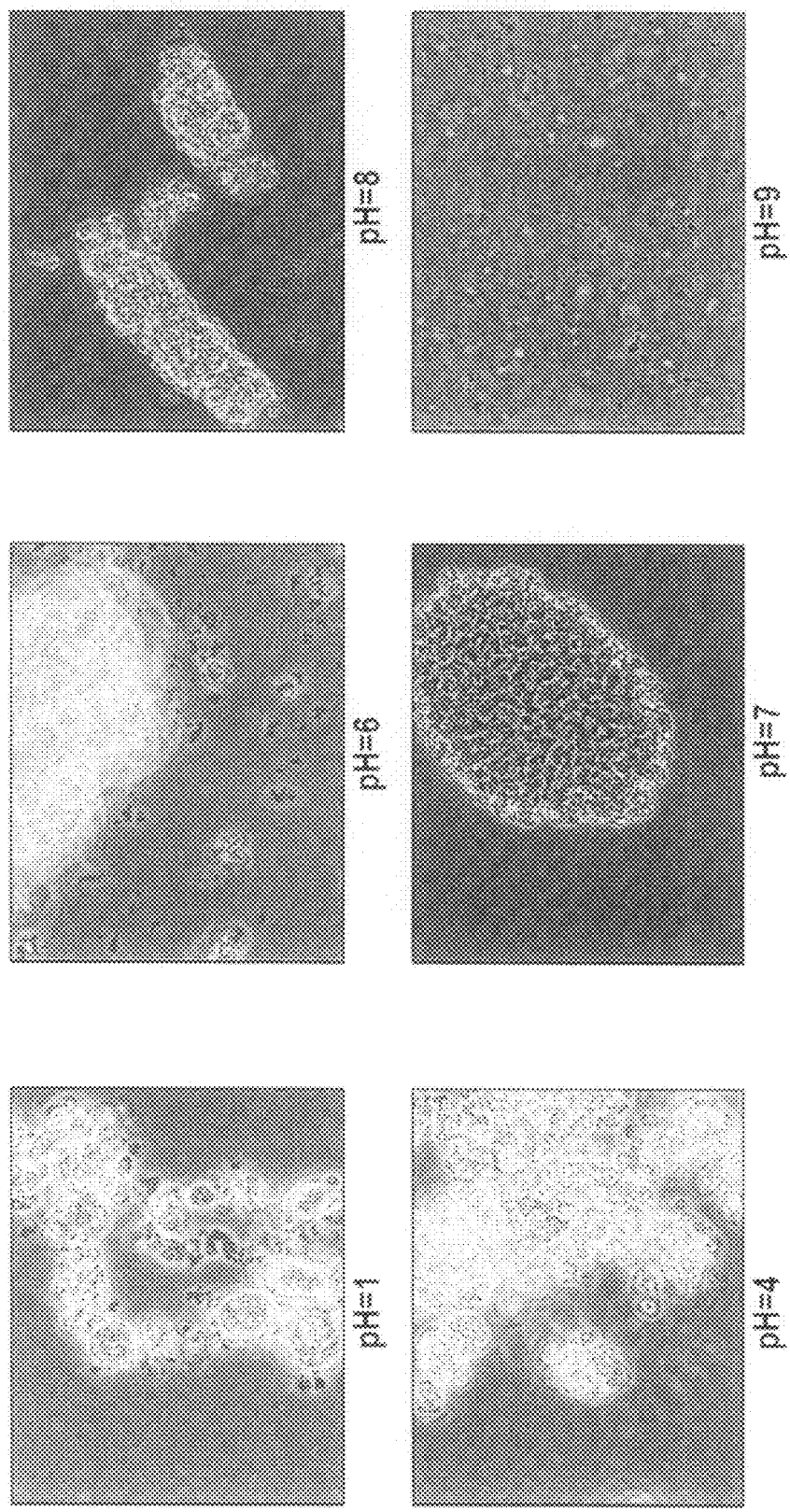
FIG. 57 is a series of images depicting caspofungin cochleates at varying pH. Caspofungin cochleates appear most stable at a pH range of about 4-6.

Caspofungin cochleates formed with an alternative acidification step (pH 5.5) as described above were subsequently treated with varying amounts of sodium hydroxide and hydrochloric acid in order to vary the pH from 1 to 9 (pH tested with litmus paper). Phase contrast micrographs at pH 1, 4, 6, 7, 8, and 9 are depicted in FIG. 57. It appears that the formulations at pH 4 and pH 6 are cochleates, but open to form liposomes when the pH is raised to 9.

Addition of Bovine Serum Albumen to Caspofungin Cochleates

Figure 53:
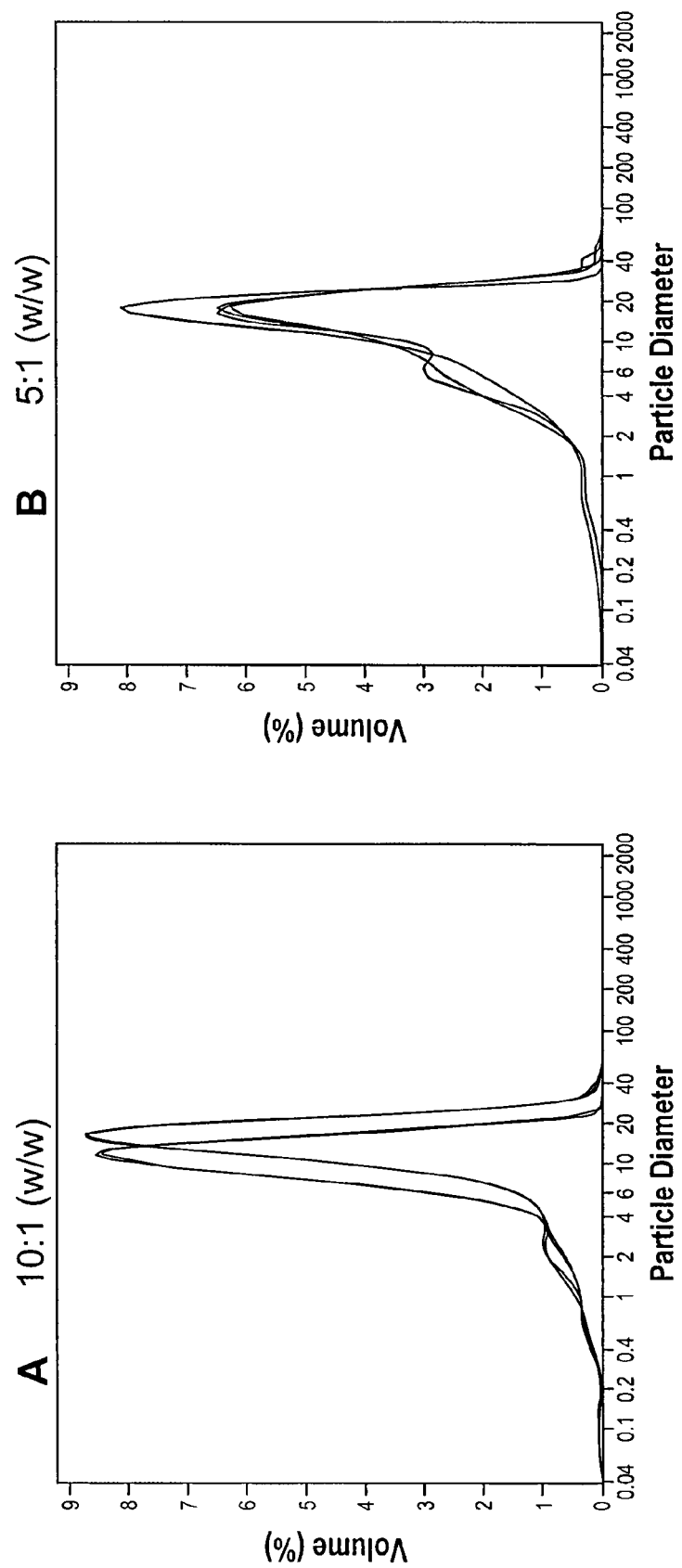
FIGS. 53A and 53B are two graphs demonstrating the size distribution of 10:1 soy PS:caspofungin (FIG. 53A) and 5:1 soy PS:caspofungin (FIG. 53B) cochleates.

The particle size distribution of 10:1 and 5:1 PS:caspofungin cochleates was measured using diffraction-based light-scattering from 0.5 to 500 microns with Beckman-Coulter LS230. FIGS. 53A and 53B (Vanco) are two graphs depicting the particle size distributions of 10:1 PS:caspofumgin cochleates and 5:1 PS:caspofungin cochleates, respectively. The 10:1 PS:caspofungin formulation was then treated with bovine serum albumin (BSA), followed by C-5 homogenization in order to reduce the mean particle size of the cochleates. Once again, the particle size distribution of the caspofungin cochleates was measured. FIG. 54 depicts the particle size distribution of the caspofungin cochleates, and demonstrates the decrease in particle size upon homogenization and addition of the BSA.

Example 26

Characterization of Caspofungin Cochleates

Caspofungin cochleates with a lipid:caspo ratio of 10:1 and 5:1 formulated as described in Example 25, using saline (0.9% NaCl), with additional Vitamin E (1% w/w, Roche) added at the liposomal stage, were characterized physically and chemically.

Morphology

Figure 51:
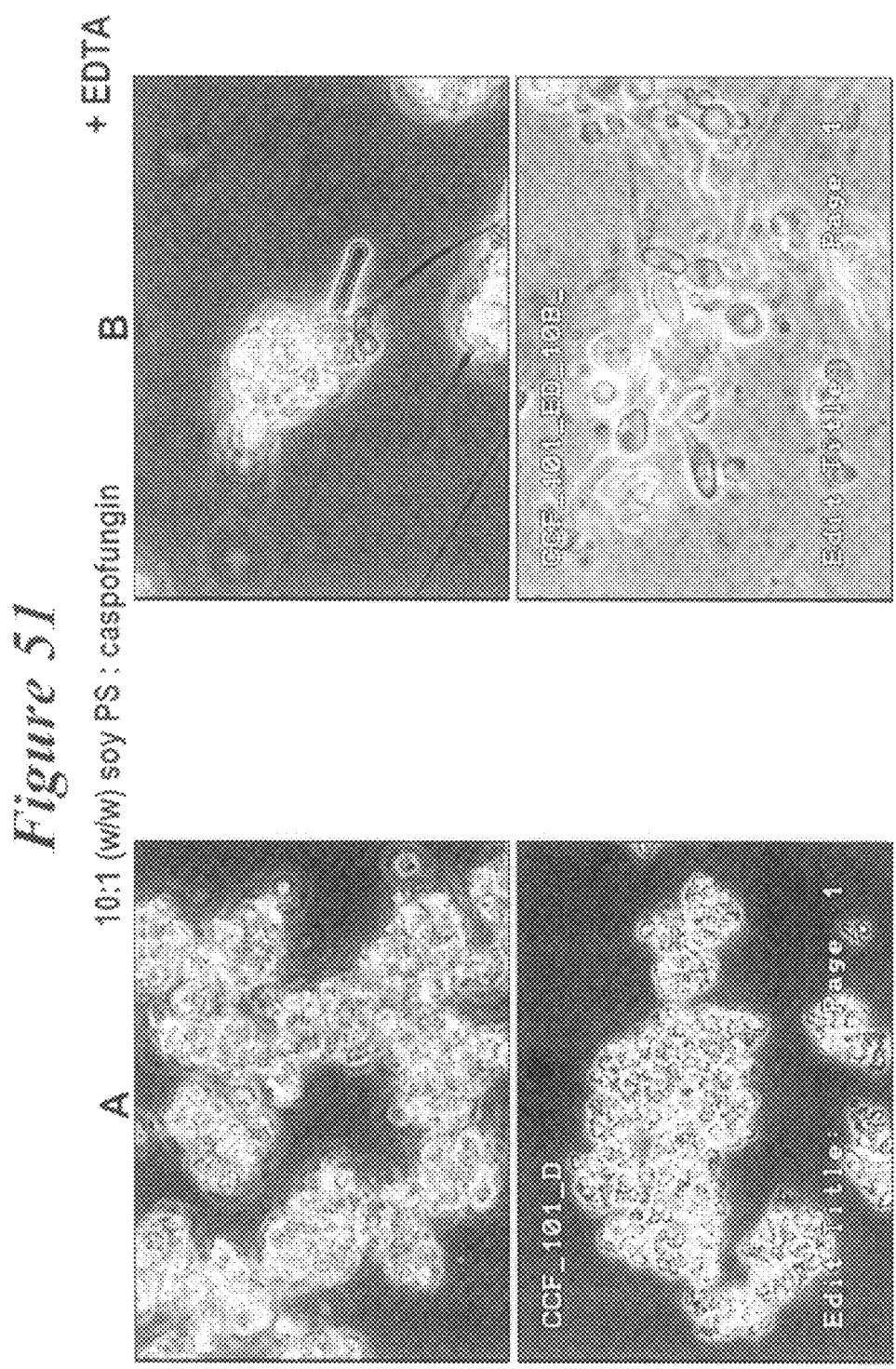
FIG. 51 is a series of images of 10:1 soy PS:caspofungin cochleates before (FIG. 51A) and after (FIG. 51B) addition of EDTA.
Figure 52:
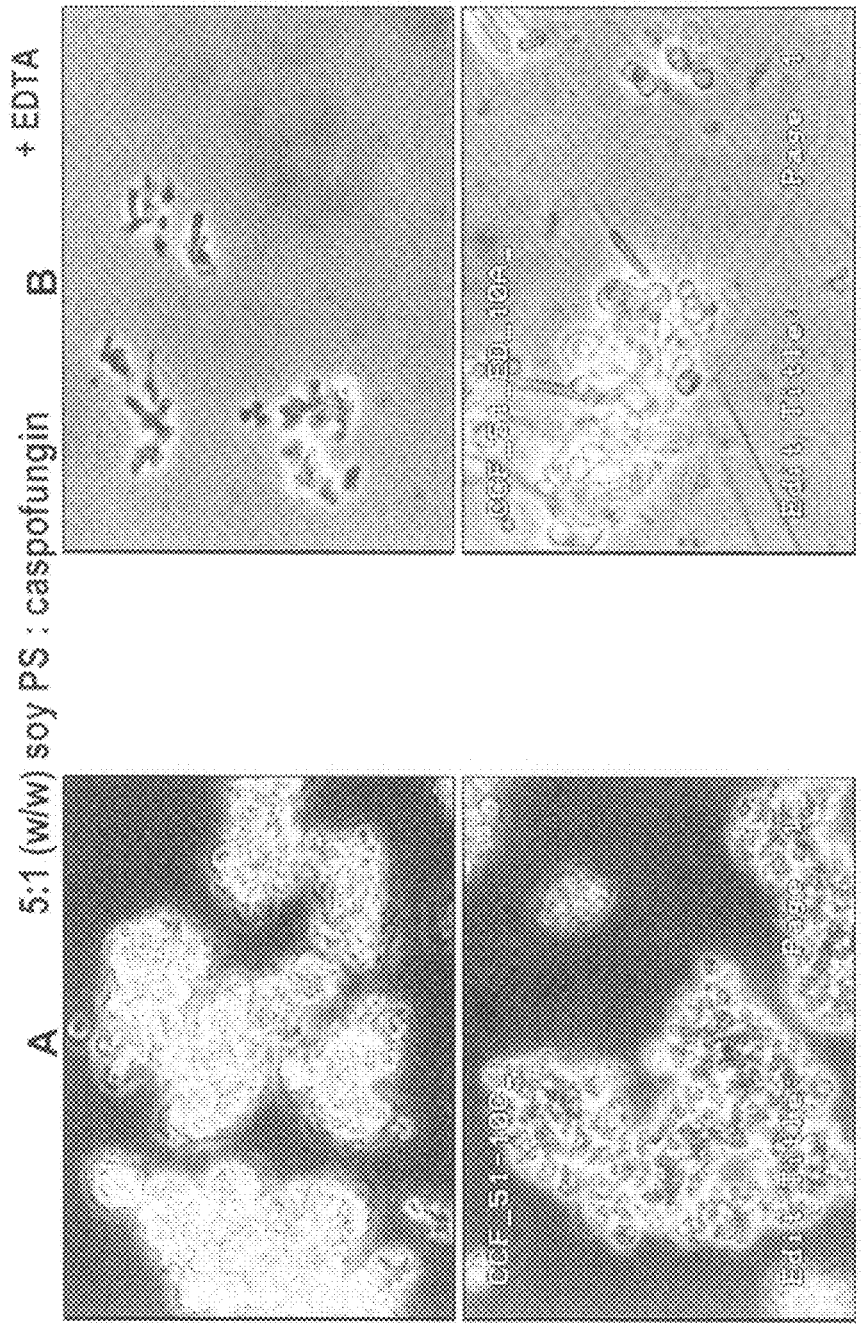
FIG. 52 is a series of images of 5:1 soy PS:caspofungin cochleates before (FIG. 52A) and after (FIG. 52B) addition of EDTA.

The morphology of 10:1 and 5:1 caspofungin cochleates was observed using phase contrast microscopy and are shown in FIGS. 51A and 52A, respectively. EDTA was also added to the caspofungin cochleates of the same formulations in order to observe the opening of the cochleate structures. Phase contrast micrographs are given in FIGS. 51B and 52B, and show the cochleates opening to form liposomes.

Chemical Characterization

Figure 55:
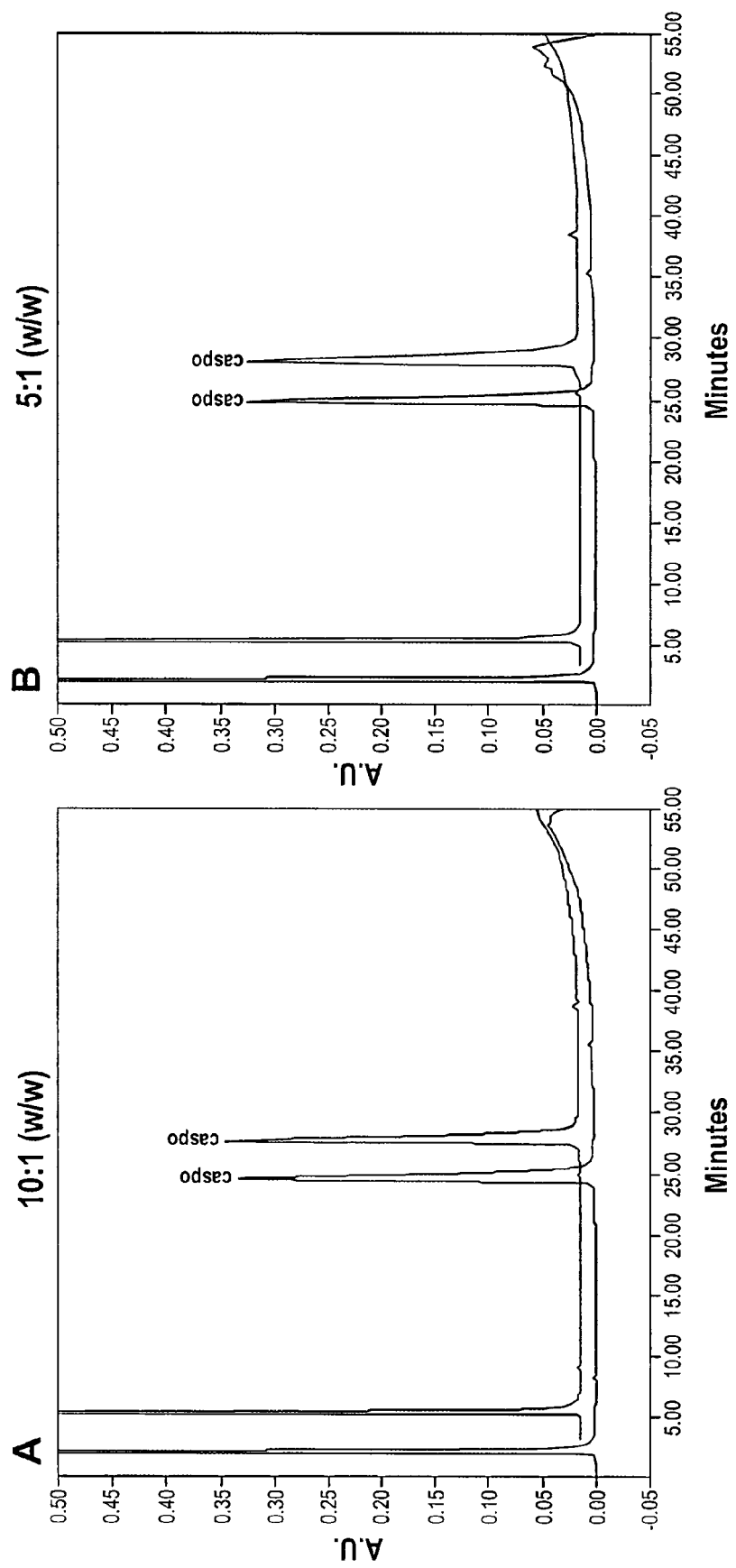
FIGS. 55A and 55B are two HPLC spectra depicting the contents of opened caspofungin cochleates. In all formulations only caspofungin is evident.

Concentrations of caspofungin in both the supernatant (to determine "free" caspofungin) and in the pellet (encochleated caspofungin) were measured using HPLC (FIG. 55), and the concentration of soy PS was determined using a modified Bartlett $P_i$ assay. The PS:caspofungin ratio in the cochleates was determined using these values. The concentration of free caspofungin in both the 10:1 formulations and the 5:1 formulations ranged from approximately 0.7% to approximately 8.2% of total caspofungin. A sterility test for bacterial growth on agar plates was also investigated, and it was determined that all formulations passed.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A cochleate composition comprising:
   Amphotericin B;
   a plurality of cochleates comprising soy phosphatidyl serine; and
   0.2%-0.4% (w/w) methylcellulose; and
   wherein the weight ratio of soy phosphatidyl serine to Amphotericin B is about 5:1.

2. The composition of claim 1, wherein the plurality of cochleates has a mean diameter of less than about 600 nm.

3. The composition of claim 1, wherein the plurality of cochleates has a mean diameter of less than about 500 nm.

4. The composition of claim 1, wherein the size distribution of the plurality of cochleates is less than about 700 nm.

5. The composition of claim 1, wherein the size distribution of the plurality of cochleates is less than about 550 nm.

6. The composition of claim 1, wherein the composition is in the form of a nasal spray.

7. A pharmaceutical composition comprising a therapeutically effective amount of the cochleate composition of claim 1 and a pharmaceutically acceptable carrier.

8. A method of treating a subject that can benefit from the administration of Amphotericin B, comprising the step of:
   administering the pharmaceutical composition of claim 7 to said subject, such that the subject is benefited.

9. The method of treatment according to claim 8, wherein the administration is by a mucosal or a systemic route.

10. The method of treatment according to claim 8, wherein the administration is a mucosal route selected from the group consisting of oral, intranasal, intraocular, intrarectal, intravaginal, topical, buccal and intrapulmonary.

11. The method of treatment according to claim 8, wherein the administration is intranasal.

12. The method of treatment according to claim 11, wherein the pharmaceutical composition is delivered in a form selected from the group consisting of a spray, a nebulae, a mist, an atomized vapor, an irrigant, an aerosol, a wash, and an inhalant.

13. The method of claim 8, wherein the pharmaceutical composition is used to treat rhinosinusitis.

14. The method of treatment according to claim 8, wherein the administration is by a systemic route selected from the group consisting of intravenous, intramuscular, intrathecal, subcutaneous, transdermal and intradermal.

15. The method of claim 8, Amphotericin B is administered to treat-parasitic disorders.

16. The method of claim 8, wherein the pharmaceutical composition is administered to treat asthma.

17. The method of claim 8, wherein the pharmaceutical composition is administered to treat at least one disorder selected from the group of consisting of asthma, chronic rhinosinusitis, allergic fungal sinusitis, sinus mycetoma, non-invasive fungus induced mucositis, and non-invasive fungus induced intestinal mucositis.

\* \* \* \* \*